US012559477B2

(12) United States Patent
Lee et al.

(10) Patent No.: US 12,559,477 B2
(45) Date of Patent: Feb. 24, 2026

(54) LIGHT-EMITTING DEVICE INCLUDING HETEROCYCLIC COMPOUND AND ELECTRONIC APPARATUS INCLUDING THE LIGHT-EMITTING DEVICE

(71) Applicant: Samsung Display Co., Ltd., Yongin-si (KR)

(72) Inventors: Hyunwoo Lee, Yongin-si (KR); Jungsub Lee, Yongin-si (KR); Hyojeong Kim, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 975 days.

(21) Appl. No.: 17/660,006

(22) Filed: Apr. 20, 2022

(65) Prior Publication Data

US 2022/0388989 A1 Dec. 8, 2022

(30) Foreign Application Priority Data

May 14, 2021 (KR) ........................ 10-2021-0062759

(51) Int. Cl.
*C07D 403/10* (2006.01)
*C07D 405/14* (2006.01)
(Continued)

(52) U.S. Cl.
CPC ......... *C07D 403/10* (2013.01); *C07D 405/14* (2013.01); *C07D 409/14* (2013.01); (Continued)

(58) Field of Classification Search
None
See application file for complete search history.

(56) References Cited

U.S. PATENT DOCUMENTS

| | | | |
|---|---|---|---|
| 9,947,876 B2 | 4/2018 | Kawamura et al. |
| 11,031,560 B2 | 6/2021 | Cha et al. |

(Continued)

FOREIGN PATENT DOCUMENTS

| | | | |
|---|---|---|---|
| CN | 110964019 A | | 4/2020 |
| JP | 2004-273190 | * | 9/2004 |

(Continued)

OTHER PUBLICATIONS

Korean Notice of Allowance for Patent Application No. 10-2021-0062759, dated Sep. 18, 2025, 2 pages.

*Primary Examiner* — Tae H Yoon

(74) *Attorney, Agent, or Firm* — Womble Bond Dickinson (US) LLP

(57) ABSTRACT

A light-emitting device and an electronic apparatus (including the light-emitting device) are provided. The light-emitting device includes a first compound represented by Formula 1 and a second compound represented by Formula 2:

Formula 1

(Continued)

10

-continued

Formula 2

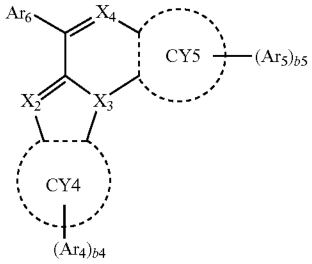

wherein detailed descriptions of Formula 1 and Formula 2 are the same as described in the present specification.

20 Claims, 3 Drawing Sheets

(51) Int. Cl.

| | |
|---|---|
| ***C07D 409/14*** | (2006.01) |
| ***C07D 487/04*** | (2006.01) |
| ***C07F 7/08*** | (2006.01) |
| ***H01L 51/00*** | (2006.01) |
| ***H10K 85/40*** | (2023.01) |
| ***H10K 85/60*** | (2023.01) |
| *H10K 50/11* | (2023.01) |
| *H10K 50/12* | (2023.01) |
| *H10K 101/10* | (2023.01) |

(52) U.S. Cl.

CPC .......... *C07D 487/04* (2013.01); *C07F 7/0812* (2013.01); *H10K 85/40* (2023.02); *H10K 85/654* (2023.02); *H10K 85/6572* (2023.02); *H10K 85/6574* (2023.02); *H10K 85/6576* (2023.02); *C07B 2200/05* (2013.01); *H10K 50/11* (2023.02); *H10K 50/12* (2023.02); *H10K 2101/10* (2023.02)

(56) References Cited

U.S. PATENT DOCUMENTS

| | | | | |
|---|---|---|---|---|
| 11,271,165 | B2 | 3/2022 | Lee et al. | |
| 2015/0221872 | A1* | 8/2015 | Hwang ................ | H10K 50/828 257/40 |
| 2017/0117488 | A1 | 4/2017 | Ahn et al. | |

FOREIGN PATENT DOCUMENTS

| | | | |
|---|---|---|---|
| JP | 2004288439 | A * | 10/2004 |
| KR | 10-2011-0134581 | A | 12/2011 |
| KR | 10-2012-0061056 | A | 6/2012 |
| KR | 10-2016-0143558 | A | 12/2016 |
| KR | 10-2017-0083960 | A | 7/2017 |
| KR | 10-2018-0008291 | A | 1/2018 |
| KR | 10-1835750 | B1 | 3/2018 |
| KR | 10-2019-0063806 | A | 6/2019 |
| KR | 10-2019-0079975 | A | 7/2019 |
| KR | 10-2019-0088624 | A | 7/2019 |

* cited by examiner

LIGHT-EMITTING DEVICE INCLUDING HETEROCYCLIC COMPOUND AND ELECTRONIC APPARATUS INCLUDING THE LIGHT-EMITTING DEVICE

CROSS-REFERENCE TO RELATED APPLICATION

This application claims priority to and the benefit of Korean Patent Application No. 10-2021-0062759, filed on May 14, 2021, in the Korean Intellectual Property Office, the disclosure of which is incorporated by reference herein in its entirety.

BACKGROUND

1. Field

One or more embodiments relate to a light-emitting device including a heterocyclic compound and an electronic apparatus including the light-emitting device.

2. Description of the Related Art

From among light-emitting devices, self-emissive devices have wide viewing angles, high contrast ratios, short response times, and/or suitable (e.g., excellent) characteristics in terms of luminance, driving voltage, and/or response speed.

In a light-emitting device, a first electrode is located on a substrate, and a hole transport region, an emission layer, an electron transport region, and a second electrode are sequentially arranged on the first electrode. Holes provided from the first electrode move toward the emission layer through the hole transport region, and electrons provided from the second electrode move toward the emission layer through the electron transport region. Carriers, such as holes and electrons, recombine in the emission layer to produce excitons. These excitons transition from an excited state to a ground state to thereby generate light.

SUMMARY

Aspects according to one or more embodiments are directed toward a light-emitting device including two or more heterocyclic compounds and an electronic apparatus including the light-emitting device.

Additional aspects will be set forth in part in the description, which follows and, in part, will be apparent from the description, or may be learned by practice of the presented embodiments of the disclosure.

According to one or more embodiments, provided is a light-emitting device including a first electrode, a second electrode facing the first electrode, an interlayer between the first electrode and the second electrode and including an emission layer, a first compound represented by Formula 1, and a second compound represented by Formula 2.

Formula 1

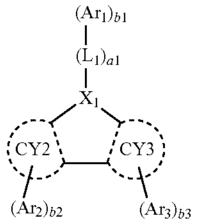

Formula 2

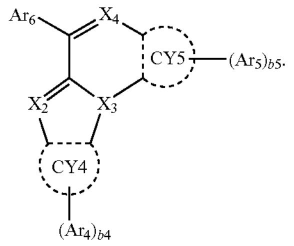

In Formulae 1 and 2, $X_1$ may be N, B, P(=O), or P(=S), $X_2$ may be N, B, P(=O), or P(=S), $X_3$ may be N, B, P(=O), or P(=S), $X_4$ may be N, B, P(=O), or P(=S), $L_1$ may be a single bond, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$, a1 may be an integer from 0 to 3, ring CY2 to ring CY5 may each independently be a $C_3$-$C_{60}$ carbocyclic group or a $C_1$-$C_{60}$ heterocyclic group, $Ar_1$ to $Ar_6$ may each independently be selected from hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, and —$P(=O)(Q_1)(Q_2)$, b1 to b5 may each independently be an integer from 0 to 10, and $R_{10a}$ may be deuterium (-D), —F, —Cl, —Br, —I, a hydroxyl group, a cyano group, or a nitro group, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof, a $C_3$-$C_{60}$ carbocyclic group, a $C_1$-$C_6$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof, or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, and wherein $Q_1$ to $Q_3$, $Q_{11}$ to $Q_{13}$, $Q_{21}$ to $Q_{23}$, and $Q_{31}$ to $Q_{33}$ may each independently be hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_6$ alkoxy group, a phenyl group, a biphenyl group, or any combination thereof; a $C_7$-$C_{60}$ aryl alkyl group; or a $C_2$-$C_{60}$ heteroaryl alkyl group.

According to one or more embodiments, provided is an electronic apparatus including the light-emitting device.

BRIEF DESCRIPTION OF THE DRAWINGS

The above and other aspects, features, and enhancements of certain embodiments of the disclosure will be more apparent from the following description taken in conjunction with the accompanying drawings, in which.

DETAILED DESCRIPTION

Figure 1:
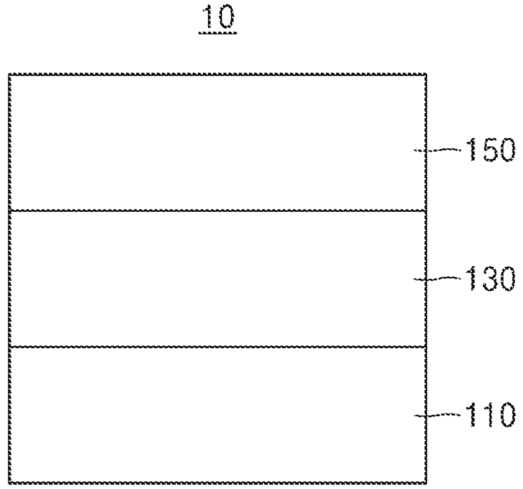
FIG. 1 is a schematic cross-sectional view of a light-emitting device according to an embodiment.

Reference will now be made in more detail to embodiments, examples of which are illustrated in the accompanying drawings, wherein like reference numerals refer to like elements throughout the specification. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Throughout the disclosure, the expression "at least one of a, b or c" indicates only a, only b, only c, both a and b, both a and c, both b and c, all of a, b, and c, or variations thereof.

A light-emitting device according to an embodiment of the present disclosure may include: a first electrode; a second electrode facing the first electrode; an interlayer located between the first electrode and the second electrode and including an emission layer; and a first compound represented by Formula 1 and a second compound represented by Formula 2:

Formula 1

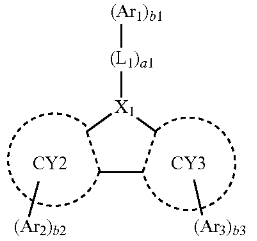

Formula 2

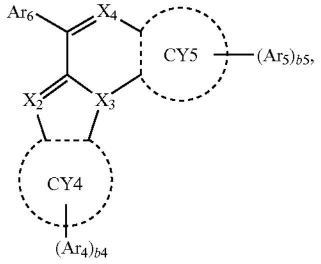

wherein, in Formulae 1 and 2, $X_1$ may be N, B, P(=O), or P(=S), $X_2$ may be N, B, P(=O), or P(=S), $X_3$ may be N, B, P(=O), or P(=S), and $X_4$ may be N, B, P(=O), or P(=S).

In an embodiment, in Formulae 1 and 2, $X_1$ may be N, P(=O), or P(=S), $X_2$ may be N, P(=O), or P(=S), $X_3$ may be N, P(=O), or P(=S), and $X_4$ may be N, P(=O), or P(=S).

In one or more embodiments, each of $X_1$ to $X_4$ in Formulae 1 and 2 may be N.

$L_1$ in Formula 1 may be a single bond, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$.

In an embodiment, $L_1$ may be: a single bond; or a methylene group, an ethylene group, a cyclopentane group, a cyclohexane group, a cycloheptane group, a cyclopentene group, a cyclohexene group, a cycloheptene group, an adamantane group, a norbornane group, a norbornene group, a bicyclo[1.1.1]pentane group, a bicyclo[2.1.1]hexane group, a bicyclo[2.2.2]octane group, a benzene group, a naphthalene group, an anthracene group, a phenanthrene group, a triphenylene group, a pyrene group, a chrysene group, a cyclopentadiene group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, a phthalazine group, a phenanthroline group, a pyrrole group, a pyrazole group, an imidazole group, a triazole group, an oxazole group, an isoxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a benzofuropyrinine group, a benzofuropyrimidine group, a benzimidazole group, an indolecarbazole group, a benzothienopyridine group, a benzothienopyrimidine group, a benzofurocarbazole group, a benzimidizoquinoxaline group, or a spiro[fluorene-fluoreno[3,4]benzofuran] group, each unsubstituted or substituted with at least one $R_{10a}$.

In one or more embodiments, $L_1$ in Formula 1 may be: a single bond; or a methylene group, a cyclopentane group, a cyclohexane group, a cycloheptane group, a cyclopentene group, a cyclohexene group, a cycloheptene group, an adamantane group, a norbornane group, a norbornene group, a bicyclo[1.1.1]pentane group, a bicyclo[2.1.1]hexane group, a bicyclo[2.2.2]octane group, a benzene group, a carbazole group, a dibenzofuran group, a dibenzothiophene group, a dibenzosilole group, a pyridine group, a pyrimidine group, a pyrazine group, a pyridazine group, a triazine group, a quinoline group, an isoquinoline group, a quinoxaline group, a quinazoline group, a phthalazine group, a benzothiazole group, a benzoxadiazole group, a benzothiadiazole group, a benzofuropyrinine group, a benzofuropyrimidine group, a benzimidazole group, an indolecarbazole group, a benzothienopyridine group, a benzothienopyrimidine group, a benzofurocarbazole group, a benzimidizoquinoxaline group, or a spiro[fluorene-fluoreno[3,4]benzofuran] group, each unsubstituted or substituted with at least one $R_{10a}$.

In one or more embodiments, $L_1$ in Formula 1 may be: a single bond; or a benzene group or a carbazole group, each unsubstituted or substituted with at least one $R_{10a}$.

In one or more embodiments, $L_1$ in Formula 1 may be: a single bond; or a group represented by one of Formulae 3-1 to 3-7.

3-1

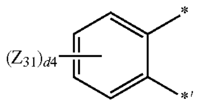

3-2

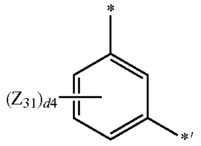

3-3

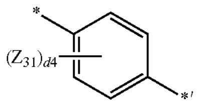

3-4

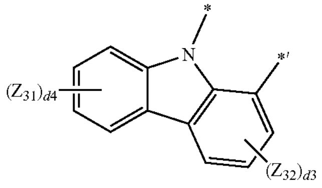

3-5

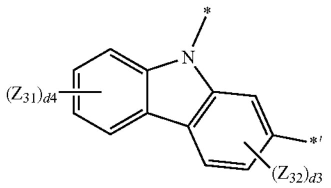

-continued 3-6

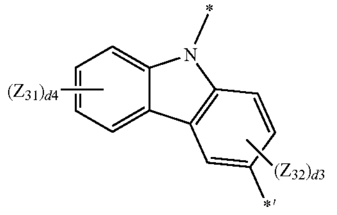

3-7

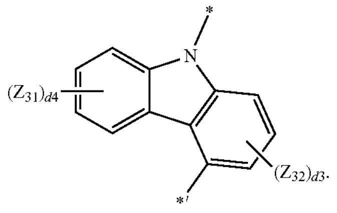

In Formulae 3-1 to 3-7, $Z_{31}$ and $Z_{32}$ may each independently be hydrogen or may be the same as described in connection with $R_{10a}$, d3 may be an integer from 0 to 3, d4 may be an integer from 0 to 4, and * and *' may each indicate a binding site to a neighboring atom.

In one or more embodiments, $L_1$ in Formula 1 may be: a single bond; or a group represented by one of Formulae 3-1 to 3-3 and 3-6.

a1 in Formula 1 may be an integer from 0 to 3.

In an embodiment, a1 in Formula 1 may be an integer from 0 to 2.

ring CY2 to ring CY5 in Formulae 1 and 2 may each independently be a $C_3$-$C_{60}$ carbocyclic group or a $C_1$-$C_{60}$ heterocyclic group.

In an embodiment, ring CY2 to ring CY5 in Formulae 1 and 2 may each independently be a benzene group, a naphthalene group, an anthracene group, a dibenzothiophene group, a carbazole group, a fluorene group, a dibenzosilole group, a dibenzofuran group, a cyclopentene group, a dihydrosilole group, a dihydropyrrole group, a dihydrofuran group, a dihydrothiophene group, a dihydroselenophene group, a dihydroindene group, a dihydrobenzosilole group, an indoline group, a dihydrobenzofuran group, a dihydrobenzothiophene group, a dihydrobenzoselenophene group, a dihydrocyclopentapyridine group, a dihydrosilolepyridine group, a dihydropyrrolopyridine group, a dihydrofuranpyridine group, a dihydrothienopyridine group, a dihydroselenophenopyridine group, a dihydrocyclopentapyrimidine group, a dihydrosilolepyrimidine group, a dihydropyrrolopyrimidine group, a dihydrofuranpyrimidine group, a dihydrothienopyrimidine group, a dihydroselenophenopyrimidine group, a dihydrocyclopentapyridazine group, a dihydrosilolepyridazine group, a dihydropyrrolopyridazine group, a dihydrofuranpyridazine group, a dihydrothienopyridazine group, a dihydroselenophenopyridazine group, a dihydrocyclopentapyrazine group, a dihydrosilolepyrazine group, a dihydropyrrolopyrazine group, a dihydrofuranpyrazine group, a dihydrothienopyrazine group, a dihydroselenophenopyrazine group, a dihydrocyclopentatriazine group, a dihydrosiloletriazine group, a dihydropyrrolotriazine group, a dihydrofurantriazine group, a dihydrothienotriazine group, or a dihydroselenophenotriazine group, each unsubstituted or substituted with at least one $R_{10a}$.

In one or more embodiments, ring CY2 to ring CY5 in Formulae 1 and 2 may each independently be a benzene group, a naphthalene group, a carbazole group, a dibenzofuran group, a fluorene group, a dibenzothiophene group, or a dibenzosilole group, each unsubstituted or substituted with at least one $R_{10a}$.

In an embodiment, ring CY2 and ring CY3 in Formula 1 may each independently be a benzene group unsubstituted or substituted with at least one $R_{10a}$.

In an embodiment, ring CY4 and ring CY5 in Formula 2 may each independently be a benzene group unsubstituted or substituted with at least one $R_{10a}$.

In an embodiment, ring CY2 in Formula 1 may be a group represented by one of Formulae CY2-1 to CY2-5.

CY2-1

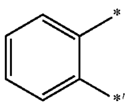

CY2-2

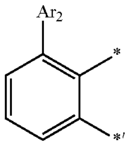

CY2-3

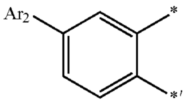

CY2-4

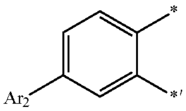

CY2-5

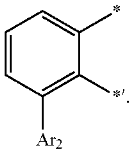

In Formulae CY2-1 to CY2-5, $Ar_2$ is the same as described in the present specification, * indicates a binding site to $X_1$ in Formula 1, and *' indicates a binding site to an element included in ring CY3 in Formula 1.

In one or more embodiments, ring CY2 in Formula 1 may be a group represented by Formula CY2-1 or CY2-5.

In an embodiment, ring CY3 in Formula 1 may be a group represented by one of Formulae CY3-1 to CY3-5.

CY3-1

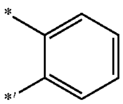

CY3-2

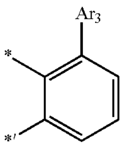

-continued

CY3-3

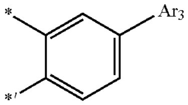

CY3-4

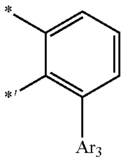

CY3-5

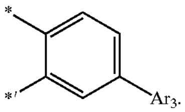

In Formulae CY3-1 to CY3-5, $Ar_3$ is the same as described in the present specification, * indicates a binding site to $X_1$ in Formula 1, and *' indicates a binding site to an element included in ring CY2 in Formula 1.

In one or more embodiments, ring CY3 in Formula 1 may be a group represented by Formula CY3-1 or CY3-5.

In an embodiment, ring CY4 in Formula 2 may be a group represented by one of Formulae CY4-1 to CY4-5.

CY4-1

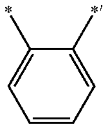

CY4-2

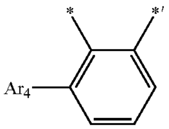

CY4-3

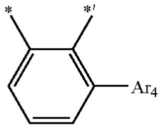

CY4-4

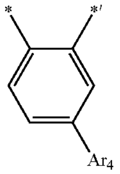

CT4-5

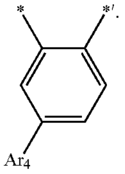

In Formulae CY4-1 to CY4-5, $Ar_4$ is the same as described in the present specification, * indicates a binding site to $X_2$ in Formula 2, and *' indicates a binding site to $X_3$ in Formula 2.

In one or more embodiments, ring CY4 in Formula 2 may be a group represented by Formula CY4-1 or CY4-5.

In an embodiment, ring CY5 in Formula 2 may be a group represented by one of Formulae CY5-1 to CY5-5.

CY5-1

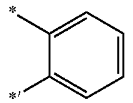

CY5-2

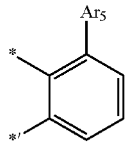

CY5-3

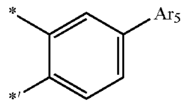

CY5-4

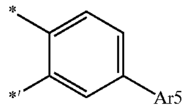

CY5-5

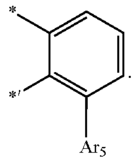

In Formulae CY5-1 to CY5-5, $Ar_5$ is the same as described in the present specification, * indicates a binding site to $X_4$ in Formula 2, and *' indicates a binding site to $X_3$ in Formula 2.

In one or more embodiments, ring CY5 in Formula 2 may be a group represented by Formula CY5-1 or CY5-4.

$Ar_1$ to $Ar_6$ may each independently be selected from hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$ (e.g., with one or more $R_{10a}$s), —Si($Q_1$)($Q_2$)($Q_3$), —N($Q_1$)($Q_2$), —B($Q_1$)($Q_2$), —C(═O)($Q_1$), —S(═O)$_2$($Q_1$), and —P(═O)($Q_1$)($Q_2$).

In an embodiment, $Ar_1$ to $Ar_6$ in Formulae 1 and 2 may each independently be: hydrogen, deuterium, —F, —Cl, —Br, —I, a hydroxyl group, a cyano group, a nitro group, a $C_1$-$C_{20}$ alkyl group, or a $C_1$-$C_{20}$ alkoxy group; a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a naphthyl group, an anthracenyl group, a carbazolyl group, a pyridinyl group, a pyrimidinyl group, a pyridazinyl group, a pyrazinyl group, a triazinyl group, a phenanthrenyl group, a quinolinyl group, an isoquinolinyl group, a spiro-bifluorenyl group, a dibenzofuranyl group, a dibenzothiophenyl group, a dibenzosilolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, a tetrabenzosilanyl group, —Si($Q_{31}$)($Q_{32}$)($Q_{33}$), or any combination thereof; a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a spiro-bifluorenyl group, a phenanthrolinyl group, a benzoimidazolyl group, a benzofuranyl group, a benzothiophenyl group, a benzosilolyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, or a tetrabenzosilanyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a spiro-bifluorenyl group, a phenanthrolinyl group, a benzoimidazolyl group, a benzofuranyl group, a benzothiophenyl group, a benzosilolyl group, a benzoisothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, a tetrabenzosilanyl group, $—Si(Q_{31})(Q_{32})(Q_{33})$, $—N(Q_{31})(Q_{32})$, $—B(Q_{31})(Q_{32})$, $—P(Q_{31})(Q_{32})$, $—C(=O)(Q_{31})$, $—S(=O)_2(Q_{31})$, $—P(=O)(Q_{31})(Q_{32})$, or any combination thereof; or $—Si(Q_1)(Q_2)(Q_3)$, $—N(Q_1)(Q_2)$, $—B(Q_1)(Q_2)$, $—C(=O)(Q_1)$, $—S(=O)_2(Q_1)$, or $—P(=O)(Q_1)(Q_2)$, wherein $Q_1$ to $Q_3$ and $Q_{31}$ to $Q_{33}$ may each independently be: $—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, or $—CD_2CDH_2$; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, a terphenyl group, a pyridinyl group, a pyrimidinyl group, a pyridazinyl group, a pyrazinyl group, a triazinyl group, a naphthyl group, a carbazolyl group, a dibenzofuranyl group, a dibenzothiophenyl group, a dibenzosilolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, or a tetrabenzosilanyl group, each unsubstituted or substituted with deuterium, a $C_1$-$C_{20}$ alkyl group, a phenyl group, a biphenyl group, a terphenyl group, a pyridinyl group, a pyrimidinyl group, a pyridazinyl group, a pyrazinyl group, a triazinyl group, a naphthyl group, a carbazolyl group, a dibenzofuranyl group, a dibenzothiophenyl group, a dibenzosilolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, a tetrabenzosilanyl group, or any combination thereof.

In an embodiment, $Ar_1$ to $Ar_6$ in Formulae 1 and 2 may each independently be: hydrogen, deuterium, —F, a cyano group, a $C_1$-$C_{20}$ alkyl group, or a $C_1$-$C_{20}$ alkoxy group; a $C_1$-$C_{20}$ alkyl group or a $C_1$-$C_{20}$ alkoxy group, each substituted with deuterium, —F, $—CD_3$, $—CD_2H$, $—CDH_2$, $—CF_3$, $—CF_2H$, $—CFH_2$, a cyano group, or any combination thereof; a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a pyridinyl group, a pyrimidinyl group, a pyridazinyl group, a pyrazinyl group, a triazinyl group, a naphthyl group, a quinolinyl group, an isoquinolinyl group, a fluorenyl group, a phenanthrenyl group, an anthracenyl group, a thiophenyl group, a furanyl group, an indenyl group, an isoindolyl group, an indolyl group, a carbazolyl group, a spiro-bifluorenyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, or a tetrabenzosilanyl group, each unsubstituted or substituted with deuterium, —F, $—CD_3$, $—CD_2H$, $—CDH_2$, $—CF_3$, $—CF_2H$, $—CFH_2$, a cyano group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a pyridinyl group, a pyrimidinyl group, a pyridazinyl group, a pyrazinyl group, a triazinyl group, a naphthyl group, a quinolinyl group, an isoquinolinyl group, a fluorenyl group, a phenanthrenyl group, an anthracenyl group, a thiophenyl group, a furanyl group, an indenyl group, an isoindolyl group, an indolyl group, a carbazolyl group, a spiro-bifluorenyl group, a benzofuranyl group, a benzothiophenyl group, a benzosilolyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, a tetrabenzosilanyl group, $—Si(Q_{31})(Q_{32})(Q_{33})$, $—N(Q_{31})(Q_{32})$, $—B(Q_{31})(Q_{32})$, $—P(Q_{31})(Q_{32})$, $—C(=O)(Q_{31})$, $—S(=O)_2(Q_{31})$, $—P(=O)(Q_{31})(Q_{32})$, or any combination thereof wherein $Q_1$ to $Q_3$ and $Q_{31}$ to $Q_{33}$ may each independently be: $—CH_3$, $—CD_3$, $—CD_2H$, $—CDH_2$, $—CH_2CH_3$, $—CH_2CD_3$, $—CH_2CD_2H$, $—CH_2CDH_2$, $—CHDCH_3$, $—CHDCD_2H$, $—CHDCDH_2$, $—CHDCD_3$, $—CD_2CD_3$, $—CD_2CD_2H$, or $—CD_2CDH_2$; or an n-propyl group, an isopropyl group, an n-butyl group, an isobutyl group, a sec-butyl group, a tert-butyl group, an n-pentyl group, an isopentyl group, a sec-pentyl group, a tert-pentyl group, a phenyl group, a biphenyl group, a terphenyl group, a pyridinyl group, a pyrimidinyl group, a pyridazinyl group, a pyrazinyl group, a triazinyl group, a quinolinyl group, an isoquinolinyl group, a naphthyl group, an anthracenyl group, a phenanthrenyl group, a spiro-bifluorenyl group, a dibenzothiophenyl group, a carbazolyl group, a dibenzofuranyl group, a dibenzothiophenyl group, a dibenzosilolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, or a tetrabenzosilanyl group, each unsubstituted or substituted with deuterium, a $C_1$-$C_{20}$ alkyl group, a phenyl group, a biphenyl group, a terphenyl group, a pyridinyl group, a pyrimidinyl group, a pyridazinyl group, a pyrazinyl group, a triazinyl group, a quinolinyl group, an isoquinolinyl group, a naphthyl group, an anthracenyl group, a phenanthrenyl group, a spiro-bifluorenyl group, a dibenzothiophenyl group, a carbazolyl group, a dibenzofuranyl group, a dibenzothiophenyl group, a dibenzosilolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, a tetrabenzosilanyl group, or any combination thereof.

In one or more embodiments, $Ar_1$ to $Ar_6$ in Formulae 1 and 2 may each independently be: hydrogen, deuterium, —F, or a cyano group; or a phenyl group, a biphenyl group, a naphthyl group, a pyridinyl group, a pyrimidinyl group, a pyridazinyl group, a pyrazinyl group, a triazinyl group, a dibenzofuranyl group, a dibenzothiophenyl group, a dibenzosilolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, or a tetrabenzosilanyl group, each unsubstituted or substituted with deuterium, —F, a cyano group, a $C_1$-$C_{20}$ alkyl group, a phenyl group, a biphenyl group, a naphthyl group, a pyridinyl group, a pyrimidinyl group, a pyridazinyl group, a pyrazinyl group, a triazinyl group, a $C_1$-$C_{20}$ alkylphenyl group, a dibenzofuranyl group, a dibenzothiophenyl group, a dibenzosilolyl group, a benzofuropyridinyl group, a benzofuropyrimidinyl group, a benzosilolepyridinyl group, a siloledipyridinyl group, a benzothienopyridinyl group, a benzothienopyrimidinyl group, a benzoimidazolyl group, a benzoimidazoquinazolinyl group, a spiro-fluorenefluorenobenzofuranyl group, a benzothiadiazolyl group, a benzoxadiazolyl group, a benzothiazolyl group, a quinazolinyl group, a quinoxalinyl group, a phthalazinyl group, an indolecarbazolyl group, a benzoimidazoquinazolinyl group, a tetrabenzosilanyl group, or any combination thereof.

In an embodiment, $Ar_1$ to $Ar_3$ in Formula 1 may each independently be: hydrogen, deuterium, or a group represented by $—Si(Q_1)(Q_2)(Q_3)$; or a group represented by one of Formulae 4-1 to 4-10.

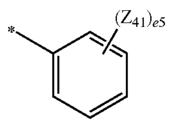
4-1

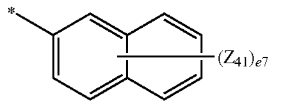
4-2

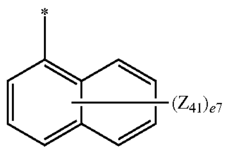
4-3

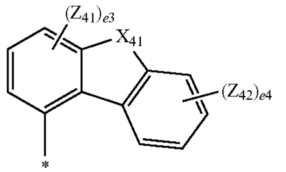
4-4

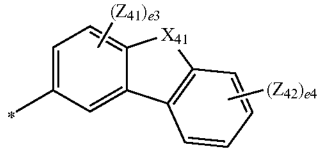
4-5

-continued 4-6

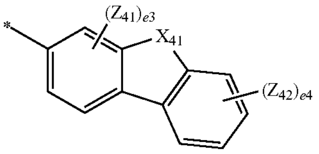

4-7

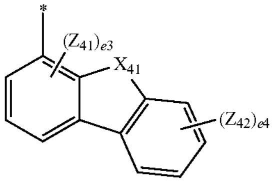

4-8

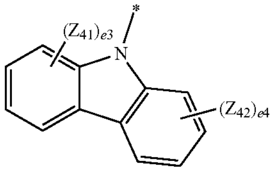

4-9

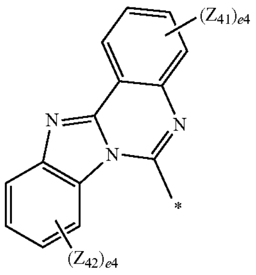

4-10

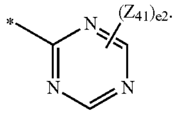

$Q_1$ to $Q_3$ may be the same as described in the present specification. In Formulae 4-1 to 4-10, $X_{41}$ may be $C(R_{41a})(R_{41b})$, $Si(R_{41a})(R_{41b})$, $N(R_{41a})$, O, S, or Se, $R_{41a}$, $R_{41b}$, $Z_{41}$, and $Z_{42}$ may each independently be hydrogen or may be the same as described in connection with $R_{10a}$, e2 may be an integer from 0 to 2, e3 may be an integer from 0 to 3, e4 may be an integer from 0 to 4, e5 may be an integer from 0 to 5, e7 may be an integer from 0 to 7, and * may indicate a binding site to a neighboring group.

In one or more embodiments, at least one of $Ar_1$ to $Ar_3$ in Formula 1 may be a group represented by Formula 4-8.

In an embodiment, $Ar_4$ to $Ar_6$ in Formula 2 may each independently be: hydrogen, deuterium, or a cyano group; or a group represented by one of Formulae 5-1 to 5-3.

5-1

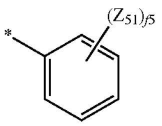

-continued 5-2

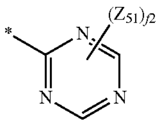

5-3

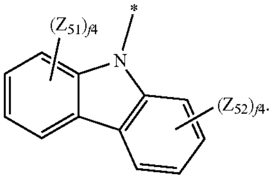

In Formulae 5-1 to 5-3, $Z_{51}$ and $Z_{52}$ may each independently be hydrogen or may be the same as described in connection with $R_{10a}$, f2 may be an integer from 0 to 2, f4 may be an integer from 0 to 4, f5 may be an integer from 0 to 5, and * may indicate a binding site to a neighboring group.

In one or more embodiments, $Ar_4$ to $Ar_6$ in Formula 2 may each independently be: hydrogen or a cyano group; or a group represented by one of Formulae 5-1 and 5-2.

In one or more embodiments, $Ar_6$ in Formula 2 may not include a carbazole group. In an embodiment, $Ar_6$ may not be a carbazole group. In an embodiment, $Ar_6$ may be a group represented by Formula 5-1 or 5-2.

b1 to b5 may each independently be an integer from 0 to 10.

In an embodiment, b2 to b5 in Formulae 1 and 2 may each independently be an integer from 0 to 4.

In an embodiment, the first compound may be one of Compounds 1-1 to 1-22.

1-1

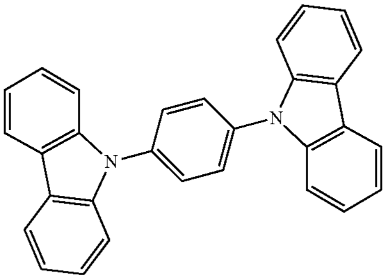

1-2

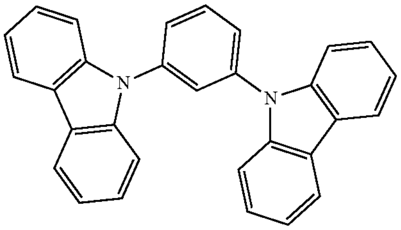

1-3
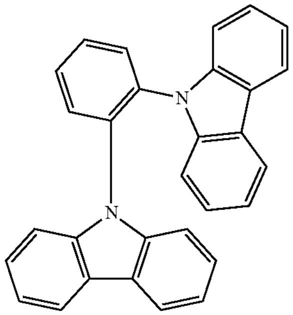
1-4
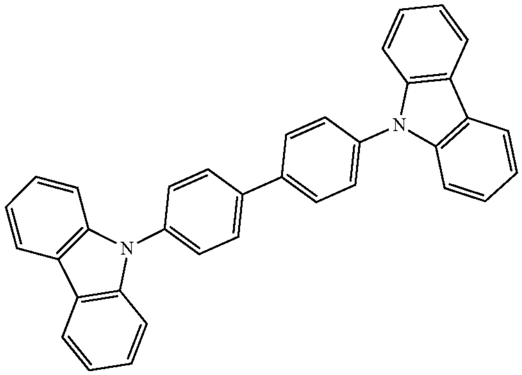
1-5
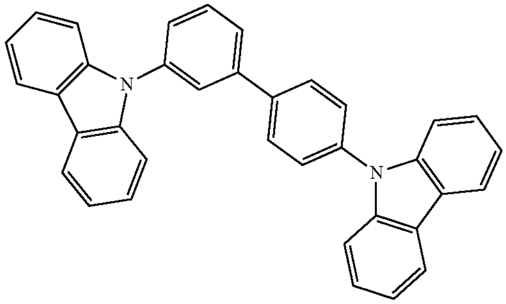
1-6
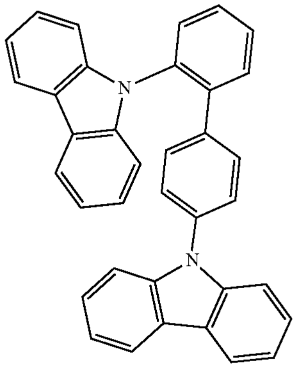
1-7
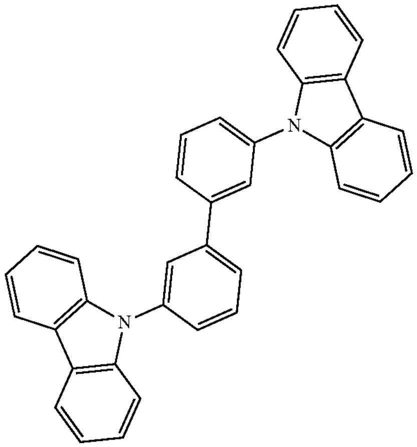
1-8
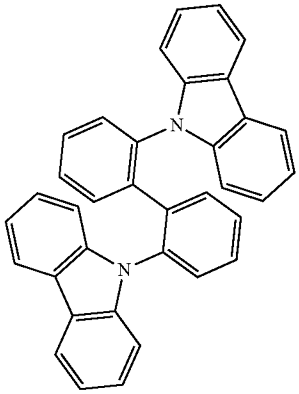
1-9
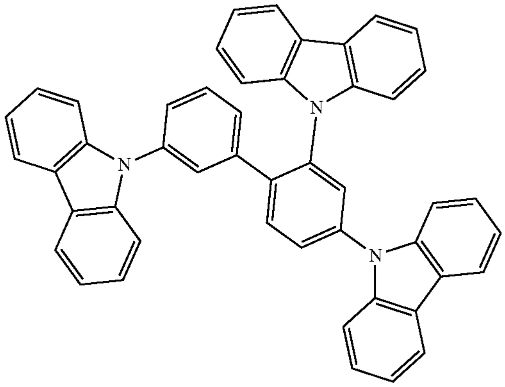

-continued
1-10
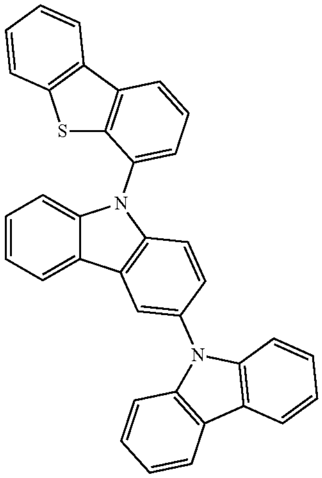
1-11
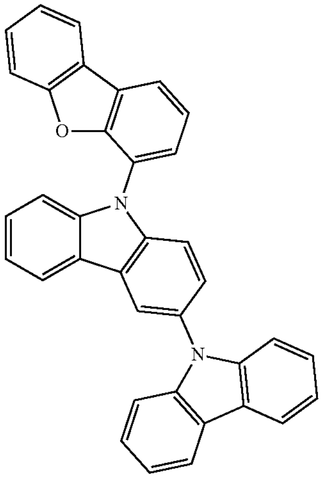
1-12
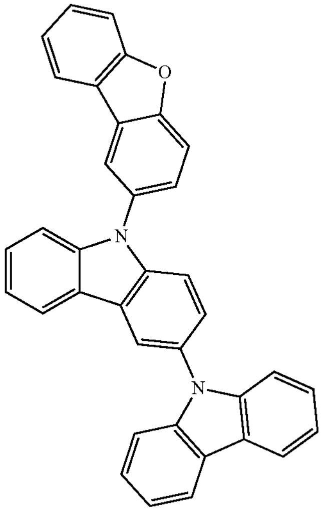
-continued
1-13
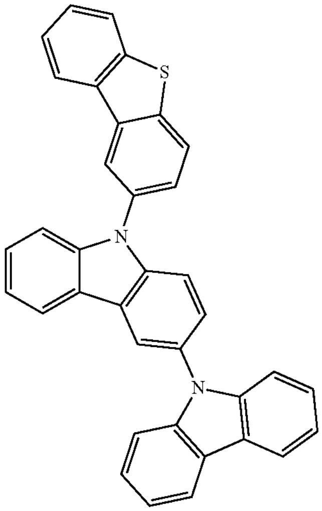
1-14
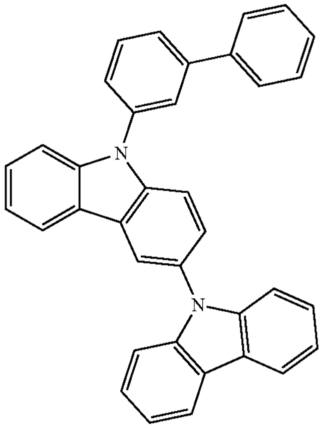
1-15
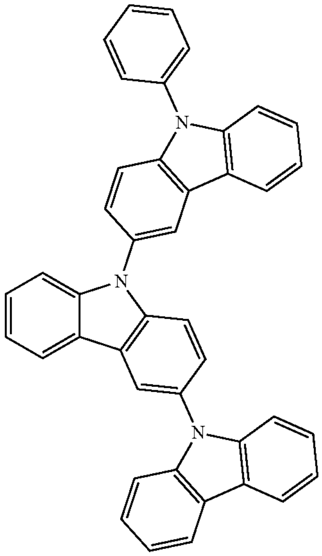

-continued
1-16
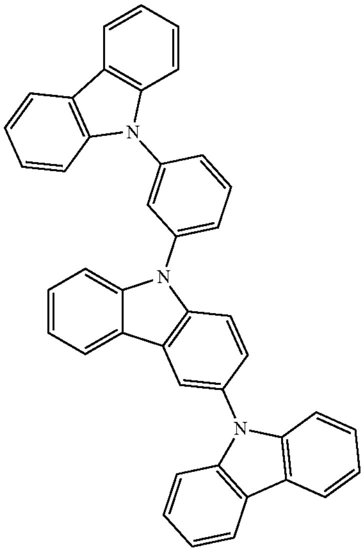
1-17
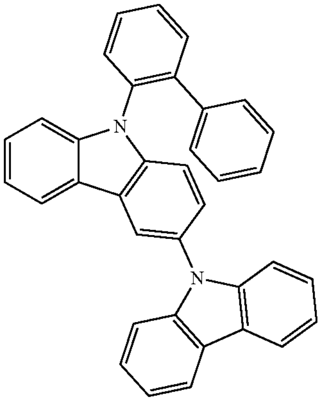
1-18
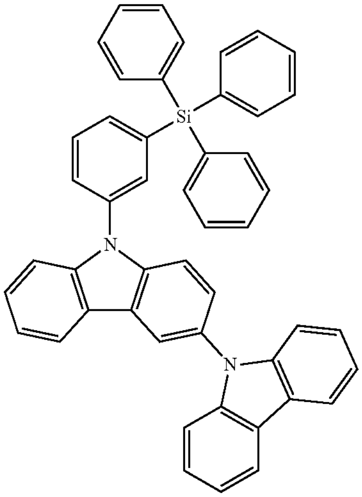
-continued
1-19
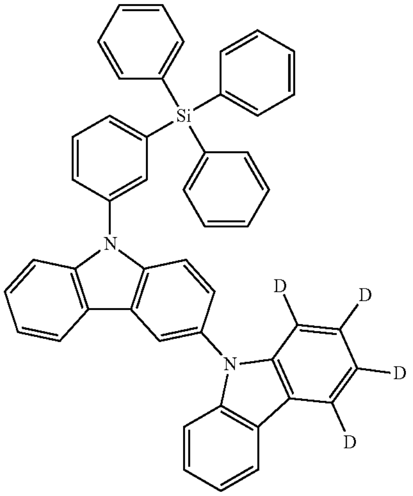
1-20
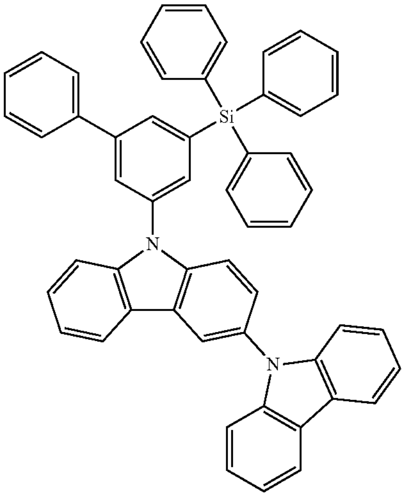
1-21
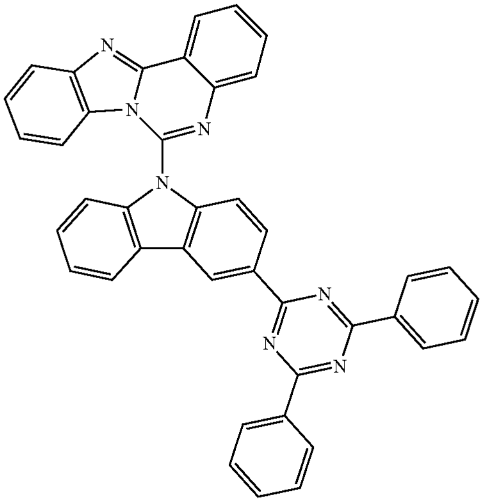

-continued
1-22
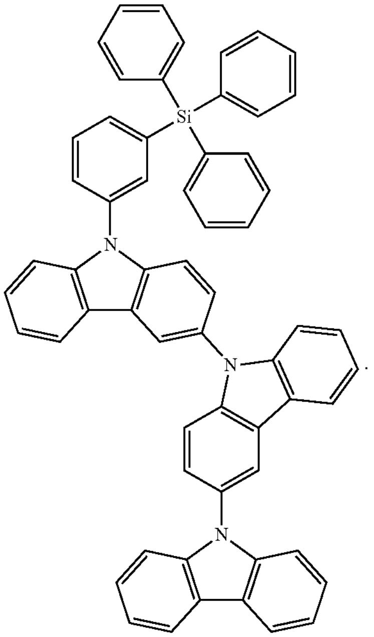
In an embodiment, the second compound may be one of Compounds 2-1 to 2-9.
2-1
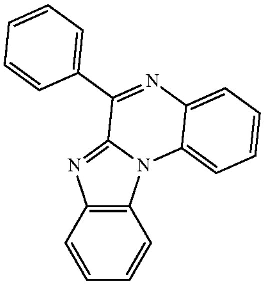
2-2
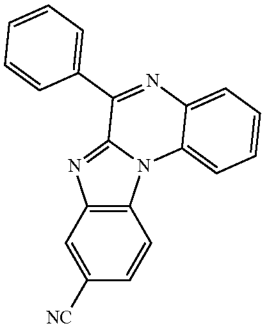
-continued
2-3
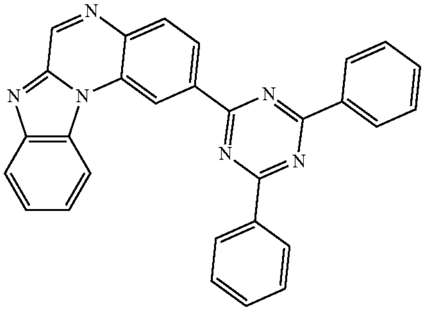
2-4
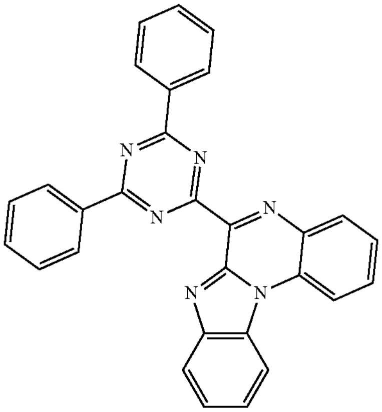
2-5
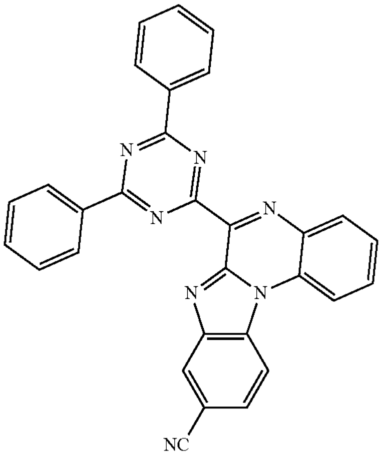
2-6
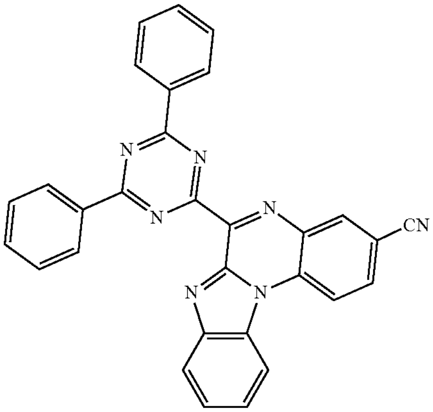

-continued 2-7

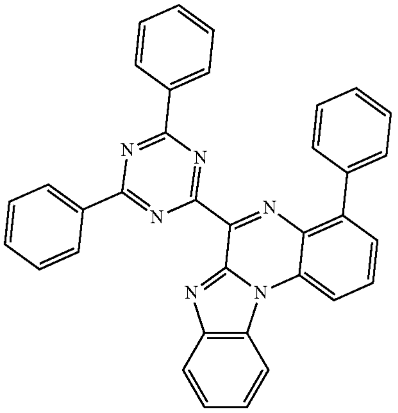

2-8

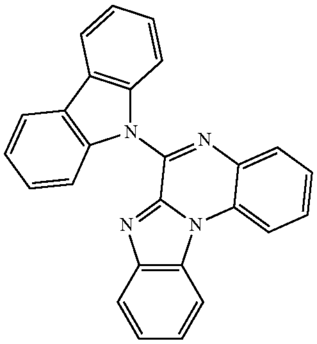

2-9

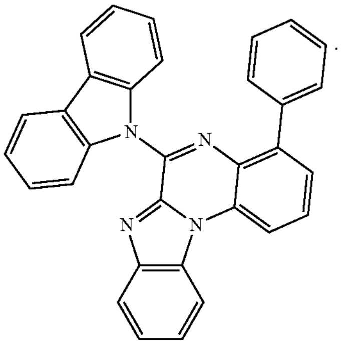

The light-emitting device includes the first compound represented by Formula 1 and the second compound represented by Formula 2.

Although not limited to a particular theory, because the light-emitting device described above concurrently or simultaneously includes the first compound represented by Formula 1 and the second compound represented by Formula 2, due to suitable (e.g., excellent) hole mobility of the first compound and suitable (e.g., excellent) electron mobility of the second compound, the charge balance in the light-emitting device may be improved.

In addition, because the first compound and the second compound correspond to host materials that convert both singlet excitons and triplet excitons into light, and the first compound has suitable (e.g., excellent) hole mobility and the second compound has suitable (e.g., excellent) electron mobility, the charge balance in the light-emitting device may be improved. As a result, the light-emitting device including both the first compound and the second compound may not only have improved lifespan characteristics, but may also concurrently or simultaneously have improved luminescence efficiency, as compared with a light-emitting device that does not include the first compound and/or the second compound.

Accordingly, an electronic device, for example, a light-emitting device, concurrently or simultaneously including the first compound represented by Formula 1 and the second compound represented by Formula 2 may have improved luminescence efficiency and/or lifespan.

Methods of synthesizing the first compound represented by Formula 1 and the second compound represented by Formula 2 may be easily recognizable by one of ordinary skill in the art by referring to Synthesis Examples and Examples provided below.

The first compound represented by Formula 1 and the second compound represented by Formula 2 may be utilized in a light-emitting device (for example, an organic light-emitting device). Accordingly, provided is a light-emitting device including: a first electrode; a second electrode facing the first electrode; an interlayer located between the first electrode and the second electrode and including an emission layer; and the first compound represented by Formula 1 and the second compound represented by Formula 2.

In an embodiment, the first electrode of the light-emitting device may be an anode, the second electrode of the light-emitting device may be a cathode, the interlayer may further include a hole transport region located between the first electrode and the emission layer and an electron transport region located between the emission layer and the second electrode, the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof.

In one or more embodiments, the first compound and the second compound may be included between the first electrode and the second electrode of the light-emitting device. Accordingly, the first compound and the second compound may be included in the interlayer of the light-emitting device, for example, in the emission layer of the interlayer. The emission layer may emit red light, green light, blue light, and/or white light.

In an embodiment, the emission layer may emit blue light. The blue light may have a maximum emission wavelength of, for example, about 400 nm to about 490 nm.

In one or more embodiments, each of the first compound and the second compound included in the emission layer may be a host.

In one or more embodiments, the first compound and the second compound may be different from each other. In this case, the first compound may have suitable (e.g., excellent) hole mobility, and the second compound may have suitable (e.g., excellent) electron mobility. Thus, a light-emitting device concurrently or simultaneously including the first compound and the second compound may concurrently or simultaneously have improved luminescence efficiency and improved lifespan characteristics.

In one or more embodiments, a ratio of an amount of the first compound to an amount of the second compound in the light-emitting device may be in a range of about 1:0.1 to about 1:10. In an embodiment, the ratio of the amount of the first compound to the amount of the second compound in the light-emitting device may be in a range of about 1:0.5 to about 1:10, about 1:0.9 to about 1:10, about 1:0.1 to about 1:5, about 1:0.1 to about 1:3, or about 1:0.1 to about 1:2. When the ratio of the amount of the first compound to the amount of the second compound is within these ranges, the luminescence efficiency and lifespan characteristics of the light-emitting device may be improved.

In one or more embodiments, the emission layer may further include a host other than the first compound and the second compound. In an embodiment, the host further included in the emission layer may include two or more different hosts.

In one or more embodiments, the emission layer may further include a dopant. In an embodiment, the dopant may include a phosphorescent dopant, a fluorescent dopant, a delayed fluorescence material, or any combination thereof as described below.

In one or more embodiments, the emission layer may include a phosphorescent dopant, a delayed fluorescence material, or any combination thereof. In an embodiment, the emission layer may concurrently or simultaneously include the first compound having suitable (e.g., excellent) hole mobility and the second compound having suitable (e.g., excellent) electron mobility, and thus, the charge balance in the emission layer may be improved. Also, due to the phosphorescent dopant, the delayed fluorescence material, or any combination thereof, the luminescence efficiency may be improved. Accordingly, the light-emitting device may concurrently or simultaneously have improved luminescence efficiency and improved lifespan characteristics.

In one or more embodiments, the emission layer in the interlayer of the light-emitting device may include a dopant and a host, the host may include the first compound and the second compound, and the dopant may emit blue light.

In an embodiment, the dopant may include a transition metal and m ligands, wherein m may be an integer from 1 to 6, the m ligands may be identical to or different from each other, at least one ligand from among the m ligands and the transition metal may be linked to each other via a carbon-transition metal bond, and the carbon-transition metal bond may be a coordinate bond. In other words, at least one ligand from among the m ligands may be a carbene ligand (for example, $Ir(pmp)_3$). The transition metal may be, for example, iridium, platinum, osmium, palladium, rhodium, gold, and/or the like. More details on the emission layer and the dopant are the same as described in the present specification.

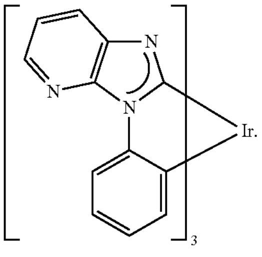

$Ir(pmp)_3$

In one or more embodiments, the light-emitting device may include a capping layer located outside the first electrode (e.g., located on the side opposite to the side facing the second electrode) or outside the second electrode (e.g., located on the side opposite to the side facing the first electrode). In an embodiment, the capping layer may include the first compound represented by Formula 1.

In an embodiment, the light-emitting device may further include at least one of a first capping layer located outside the first electrode and a second capping layer located outside the second electrode, and at least one of the first capping layer and the second capping layer may include the first compound represented by Formula 1. More details on the first capping layer and/or second capping layer are the same as described in the present specification.

In an embodiment, the light-emitting device may include:

a first capping layer located outside the first electrode and including the first compound represented by Formula 1 and the second compound represented by Formula 2;

a second capping layer located outside the second electrode and including the first compound represented by Formula 1 and the second compound represented by Formula 2; or the first capping layer and the second capping layer.

The expression "(an interlayer and/or a capping layer) includes at least one first compound" as used herein may include a case in which "(an interlayer and/or a capping layer) includes identical first compounds represented by Formula 1" and a case in which "(an interlayer and/or a capping layer) includes two or more different first compounds represented by Formula 1." The expression "(an interlayer and/or a capping layer) includes at least one second compound" as used herein may include a case in which "(an interlayer and/or a capping layer) includes identical second compounds represented by Formula 2" and a case in which "(an interlayer and/or a capping layer) includes two or more different second compounds represented by Formula 2."

In an embodiment, the interlayer and/or capping layer may include the first compound and the second compound. In this regard, the first compound and the second compound may be present in the emission layer of the light-emitting device. In one or more embodiments, the interlayer may include the first compound and the second compound. In this regard, the first compound and the second compound may be present in the same layer (for example, both the first compound and the second compound may be present in the emission layer), or may be present in different layers (for example, the first compound may be present in the emission layer, and the second compound may be present in the electron transport region).

The term "interlayer" as used herein refers to a single layer and/or all of a plurality of layers located between a first electrode and a second electrode of a light-emitting device.

According to one or more embodiments, provided is an electronic apparatus including the light-emitting device. The electronic apparatus may further include a thin-film transistor. In an embodiment, the electronic apparatus may further include a thin-film transistor including a source electrode and a drain electrode, and the first electrode of the light-emitting device may be electrically connected to the source electrode or the drain electrode. In one or more embodiments, the electronic apparatus may further include a color filter, a color conversion layer, a touch screen layer, a polarizing layer, or any combination thereof. More details on the electronic apparatus are the same as described in the present specification.

Description of FIG. 1

FIG. 1 is a schematic cross-sectional view of a light-emitting device 10 according to an embodiment of the present disclosure. The light-emitting device 10 may include a first electrode 110, an interlayer 130, and a second electrode 150.

Hereinafter, the structure of the light-emitting device 10 according to an embodiment and a method of manufacturing the light-emitting device 10 will be described in connection with FIG. 1.

First Electrode 110

In FIG. 1, a substrate may be additionally located under the first electrode 110 or above the second electrode 150. As the substrate, a glass substrate or a plastic substrate may be utilized. In one or more embodiments, the substrate may be a flexible substrate, and may include plastics with suitable (e.g., excellent) heat resistance and durability, such as polyimide, polyethylene terephthalate (PET), polycarbonate, polyethylene napthalate, polyarylate (PAR), polyetherimide, or any combination thereof.

The first electrode 110 may be formed by, for example, depositing or sputtering a material for forming the first electrode 110 on the substrate. When the first electrode 110 is an anode, a material for forming the first electrode 110 may be a high work function material that facilitates injection of holes.

The first electrode 110 may be a reflective electrode, a semi-transmissive electrode, or a transmissive electrode. When the first electrode 110 is a transmissive electrode, a material for forming the first electrode 110 may include indium tin oxide (ITO), indium zinc oxide (IZO), tin oxide ($SnO_2$), zinc oxide (ZnO), or any combinations thereof. In one or more embodiments, when the first electrode 110 is a semi-transmissive electrode or a reflective electrode, a material for forming the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof.

The first electrode 110 may have a single-layered structure consisting of a single layer or a multi-layered structure including a plurality of layers. In an embodiment, the first electrode 110 may have a three-layered structure of ITO/Ag/ITO.

Interlayer 130

The interlayer 130 may be located on the first electrode 110. The interlayer 130 may include an emission layer.

The interlayer 130 may further include a hole transport region located between the first electrode 110 and the emission layer and an electron transport region located between the emission layer and the second electrode 150.

The interlayer 130 may further include, in addition to various suitable organic materials, metal-containing compounds such as organometallic compounds, inorganic materials such as quantum dots, and/or the like.

In one or more embodiments, the interlayer 130 may include, i) two or more emitting units sequentially stacked between the first electrode 110 and the second electrode 150 and ii) a charge generation layer located between two adjacent emitting units. When the interlayer 130 includes the two or more emitting units and the charge generation layer as described above, the light-emitting device 10 may be a tandem light-emitting device.

Hole Transport Region in Interlayer 130

The hole transport region may have i) a single-layered structure consisting of a single layer consisting of a single material, ii) a single-layered structure consisting of a single layer including a plurality of different materials, or iii) a multi-layered structure having a plurality of layers including a plurality of different materials.

The hole transport region may include a hole injection layer, a hole transport layer, an emission auxiliary layer, an electron blocking layer, or any combination thereof.

In an embodiment, the hole transport region may have a multi-layered structure including a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein, in each structure, constituting layers are stacked sequentially from the first electrode 110 in the respective stated order.

The hole transport region may include a compound represented by Formula 201, a compound represented by Formula 202, or any combination thereof:

Formula 201

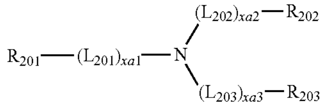

Formula 202

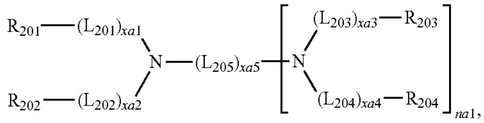

wherein, in Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—*', *—S—*', *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group (for example, a carbazole group and/or the like) unsubstituted or substituted with at least one $R_{10a}$ (for example, Compound HT16), $R_{203}$ and $R_{204}$ may optionally be linked to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$, to form a $C_8$-$C_{60}$ polycyclic group unsubstituted or substituted with at least one $R_{10a}$, and na1 may be an integer from 1 to 4.

In an embodiment, each of Formulae 201 and 202 may include at least one of the groups represented by Formulae CY201 to CY217:

CY201

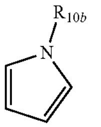

CY202

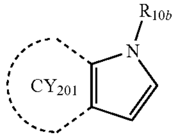

CY203

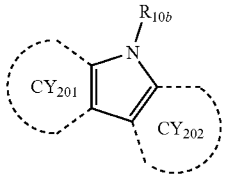

CY204

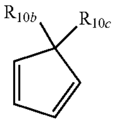

CY205

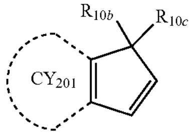

CY206

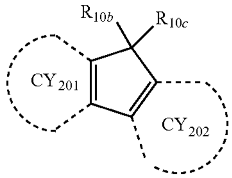

CY207

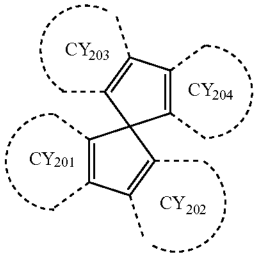

CY208

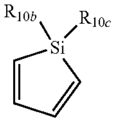

CY209

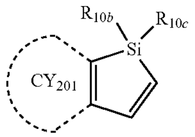

-continued

CY210

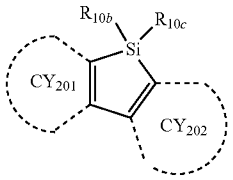

CY211

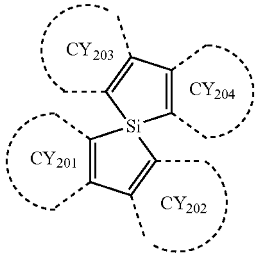

CY212

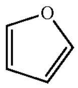

CY213

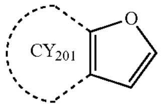

CY214

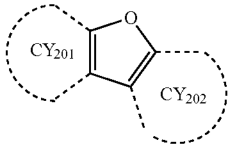

CY215

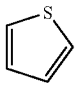

CY216

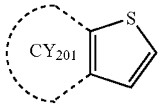

CY217

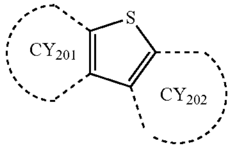

, wherein, in Formulae CY201 to CY217, $R_{10b}$ and $R_{10c}$ may be the same as described in connection with $R_{10a}$, ring CY201 to ring CY204 may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In an embodiment, ring CY201 to ring CY204 in Formulae CY201 to CY217 may each independently be a benzene group, a naphthalene group, a phenanthrene group, or an anthracene group.

In one or more embodiments, each of Formulae 201 and 202 may include at least one of the groups represented by Formulae CY201 to CY203.

In one or more embodiments, Formula 201 may include at least one of the groups represented by Formulae CY201 to CY203 and/or at least one of the groups represented by Formulae CY204 to CY217.

In one or more embodiments, in Formula 201, xa1 may be 1, $R_{201}$ may be a group represented by one of Formulae CY201 to CY203, xa2 may be 0, and $R_{202}$ may be a group represented by one of Formulae CY204 to CY207.

In one or more embodiments, each of Formulae 201 and 202 may not include any of the groups represented by Formulae CY201 to CY203.

In one or more embodiments, each of Formulae 201 and 202 may not include any of the groups represented by Formulae CY201 to CY203, and may include at least one of the groups represented by Formulae CY204 to CY217.

In one or more embodiments, each of Formulae 201 and 202 may not include any of the groups represented by Formulae CY201 to CY217.

In an embodiment, the hole transport region may include one of Compounds HT1 to HT46, m-MTDATA, TDATA, 2-TNATA, NPB(NPD), β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), or any combination thereof:

HT1

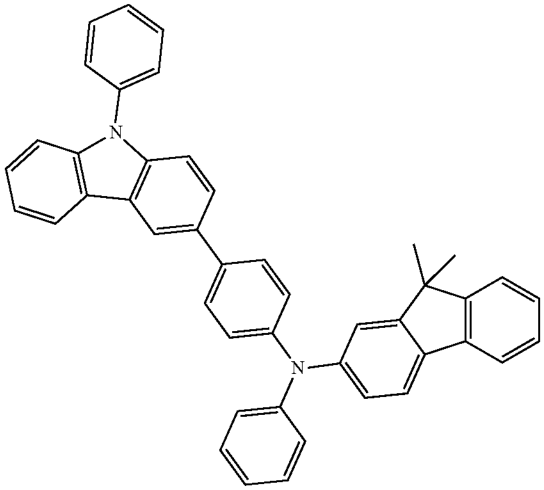

HT2

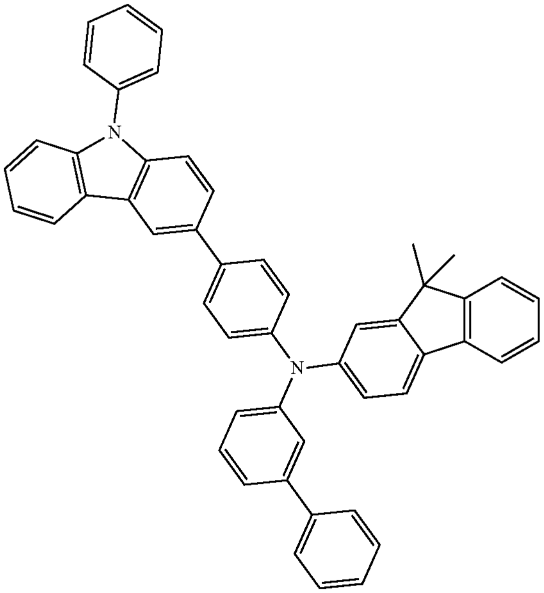

HT3

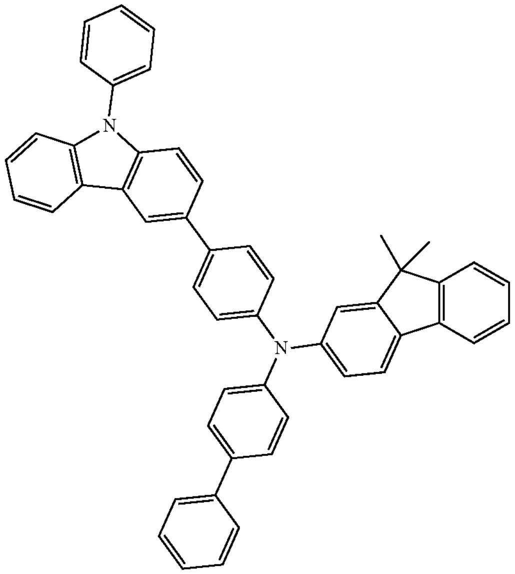

HT4

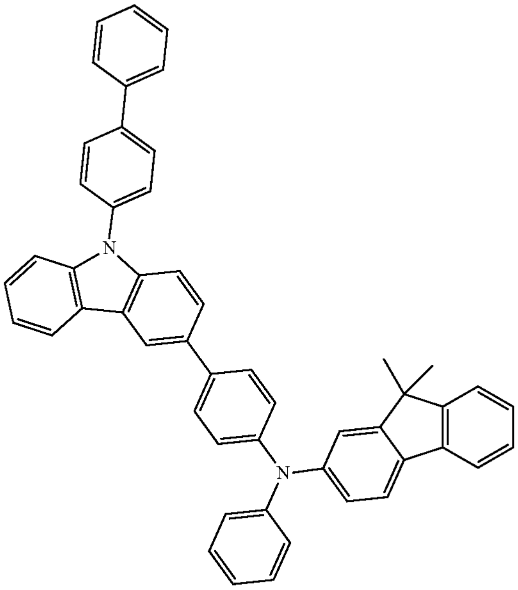

-continued
HT5
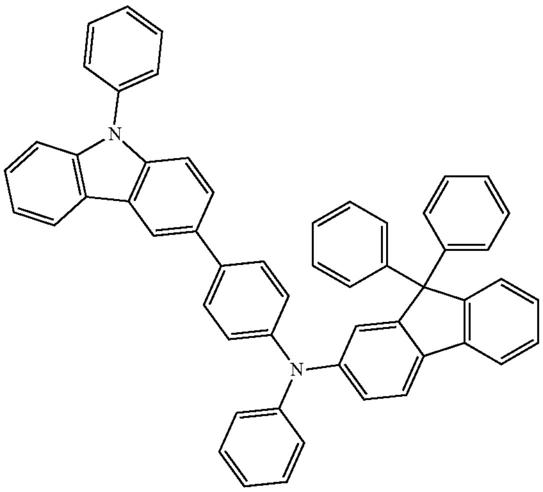
HT6
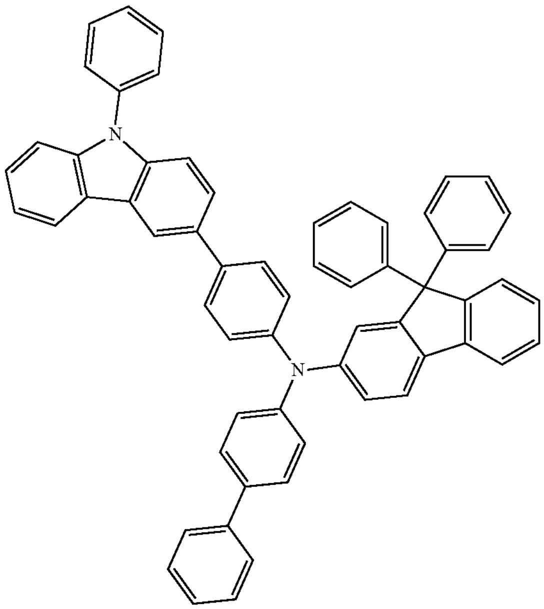
HT7
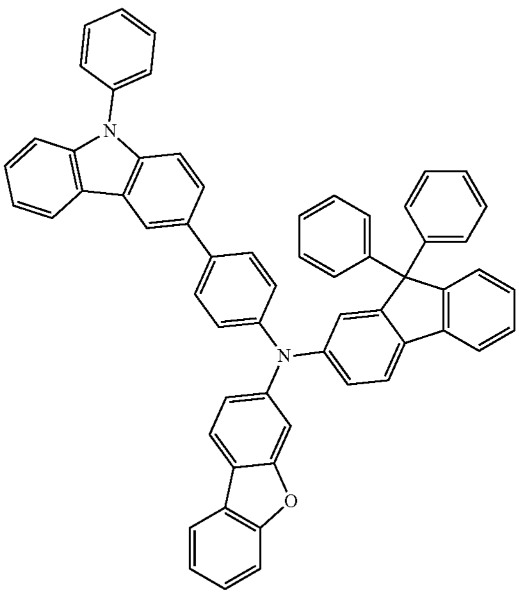
HT8
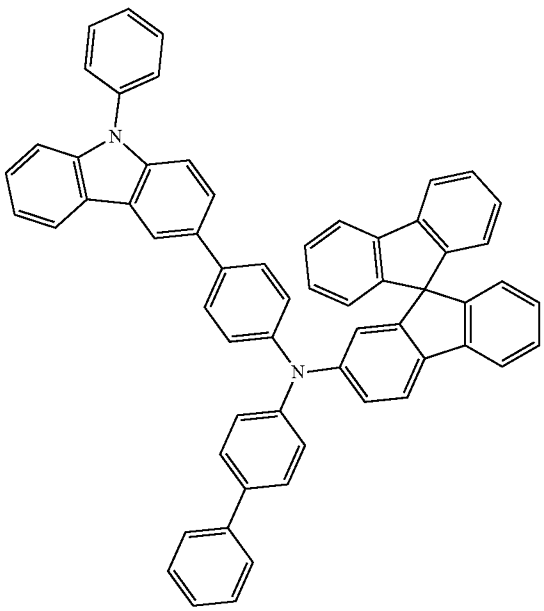

-continued
HT9
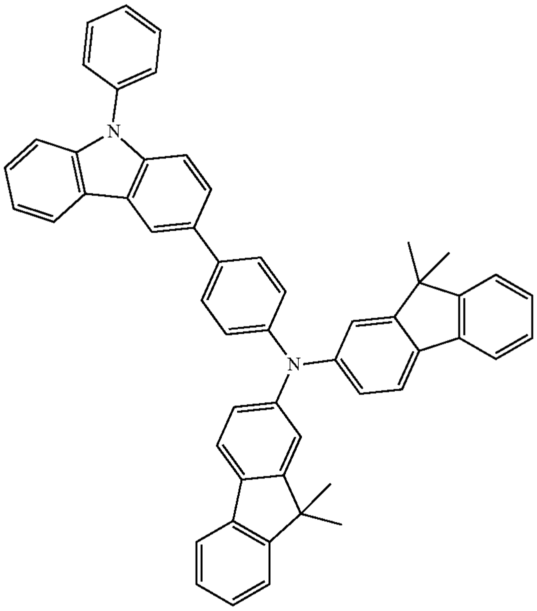
HT10
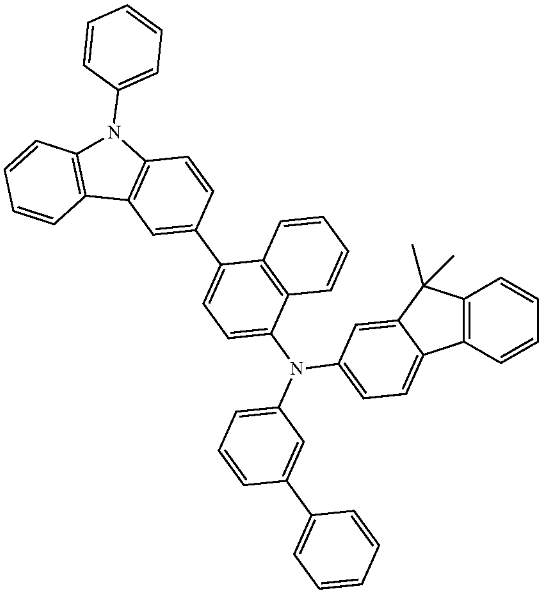
HT11
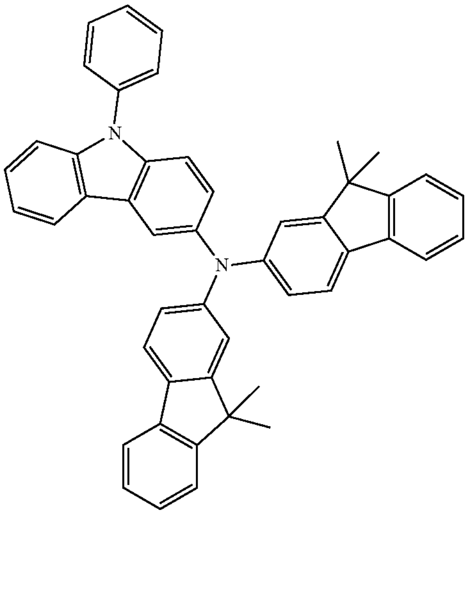
HT12
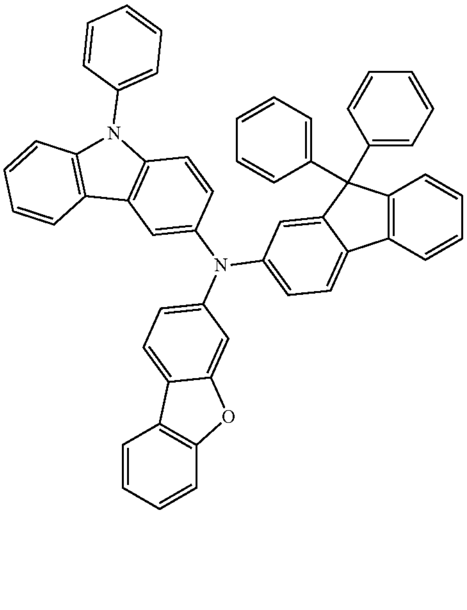

-continued
HT13
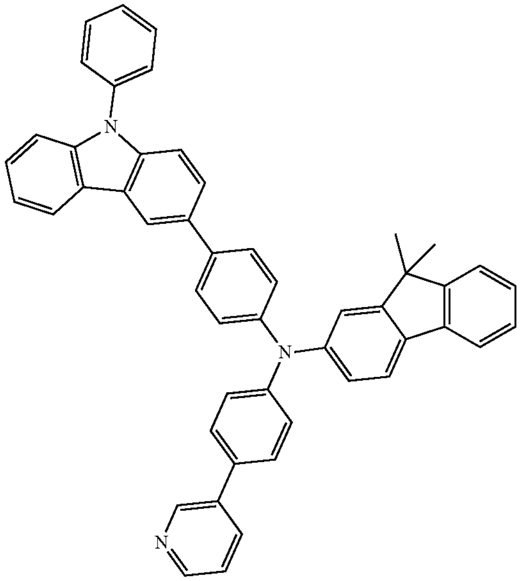
HT14
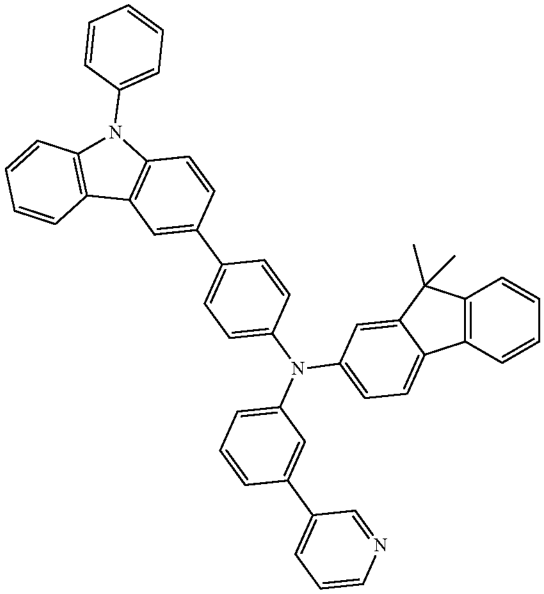
HT15
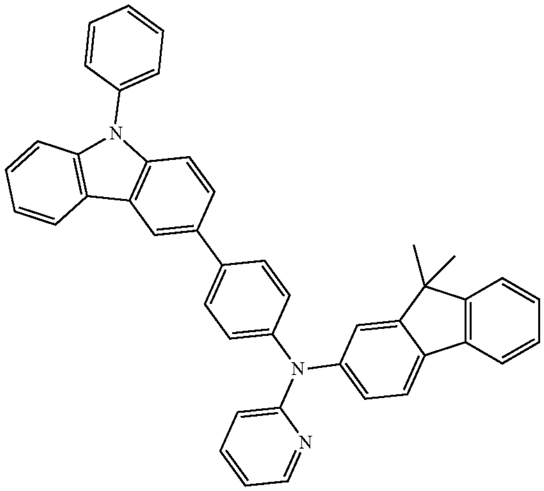
HT16
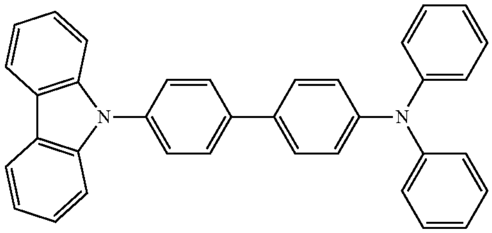
HT17
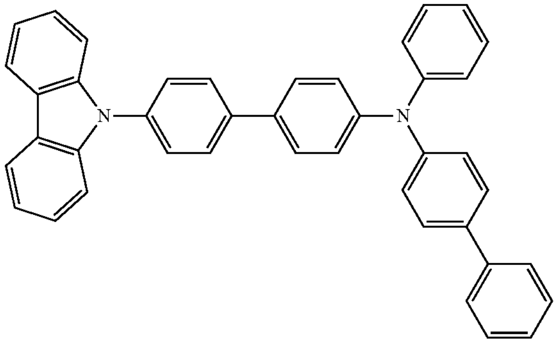
HT18
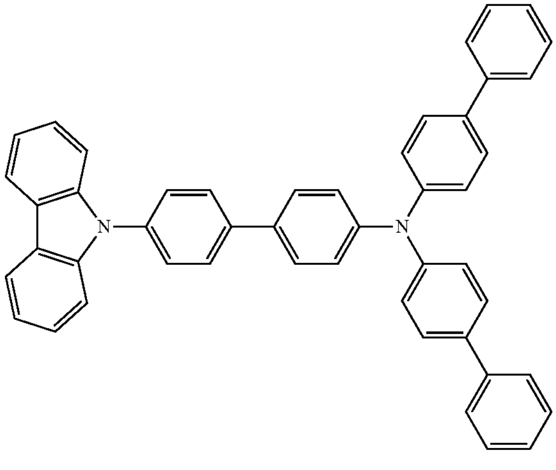

-continued
HT19
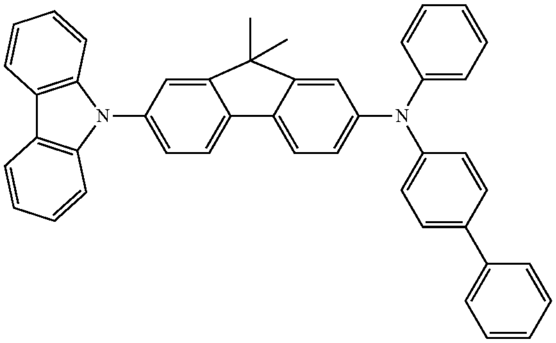
HT20
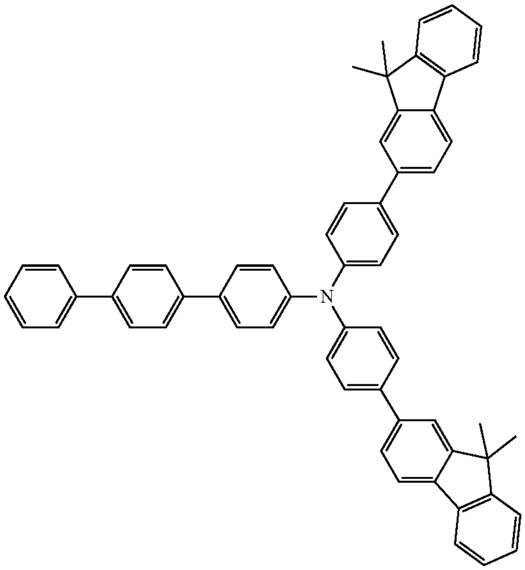
HT21
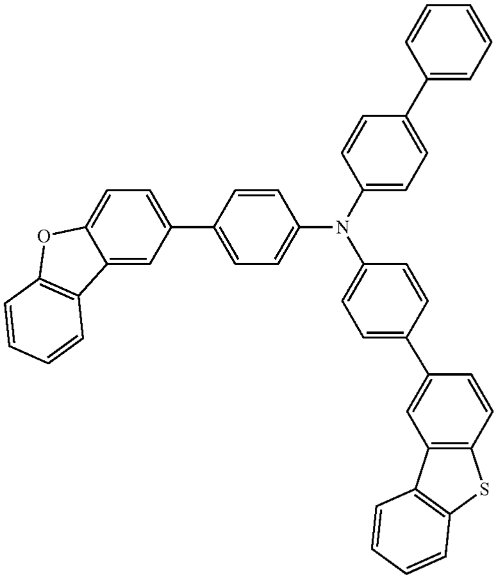
HT22
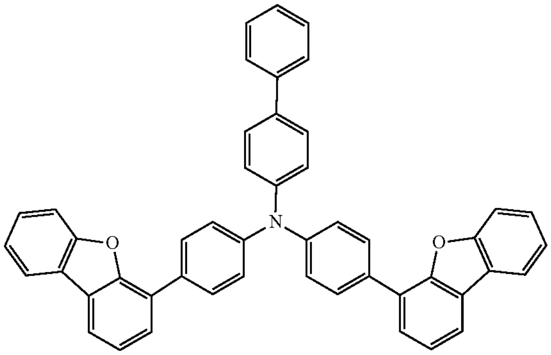

-continued
HT23
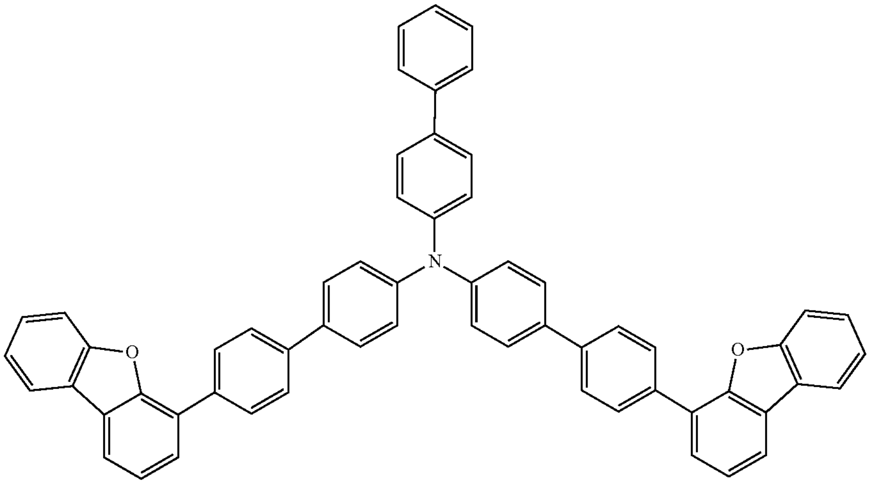
HT24
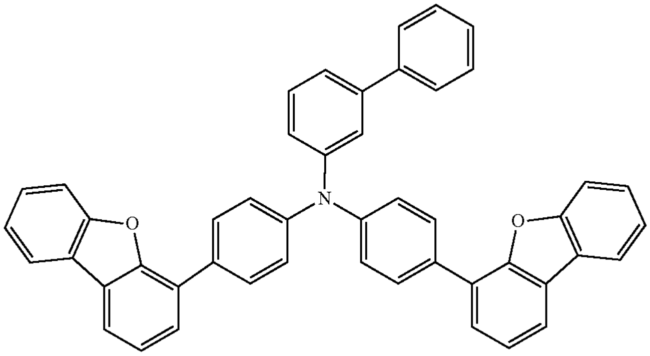
HT25
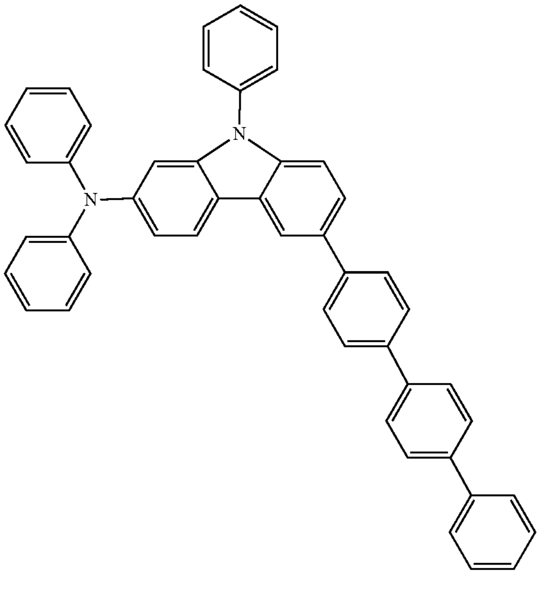
HT26
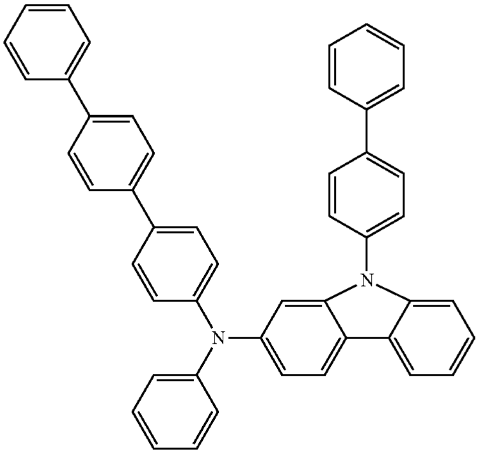

-continued
HT27
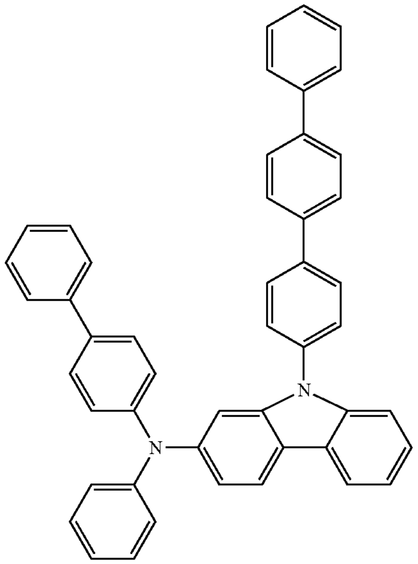
HT28
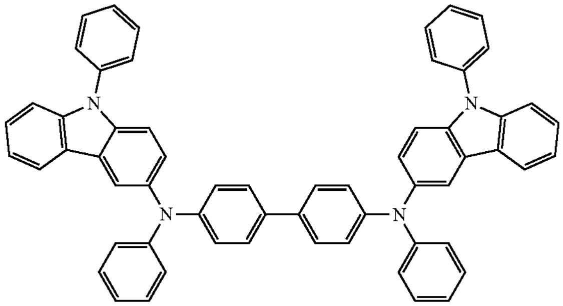
HT29
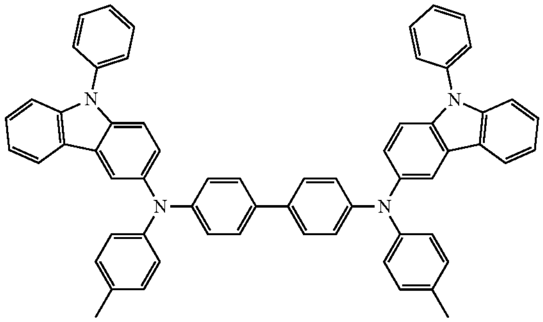
HT30
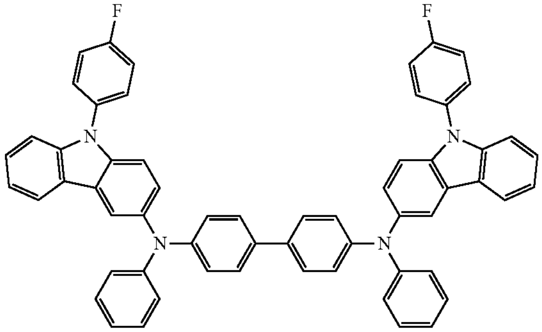
HT31
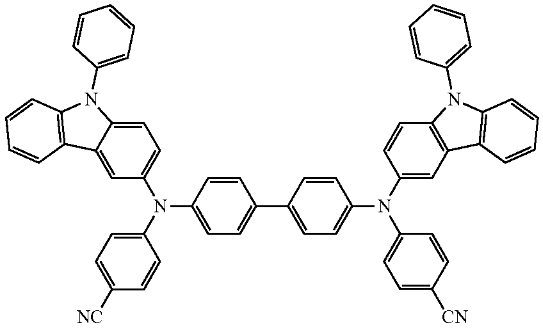
HT32
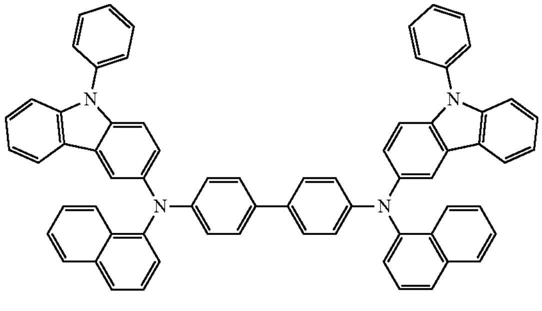

-continued
HT33
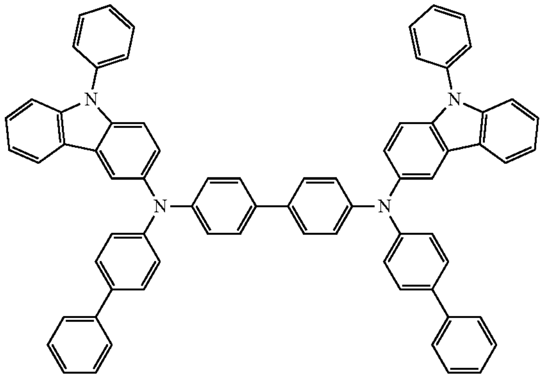
HT34
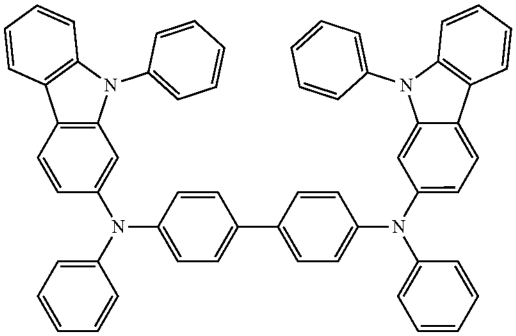
HT35
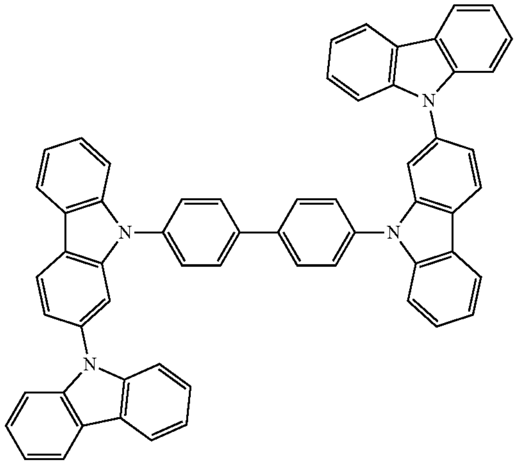
HT36
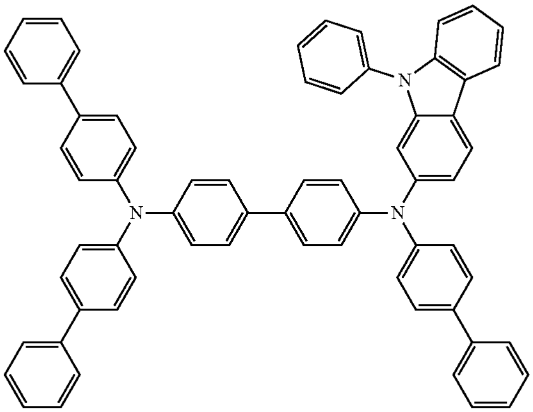
HT37
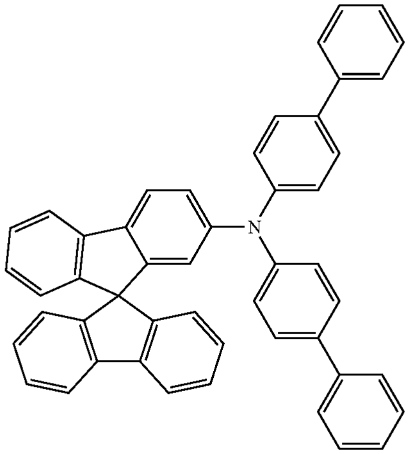
HT38
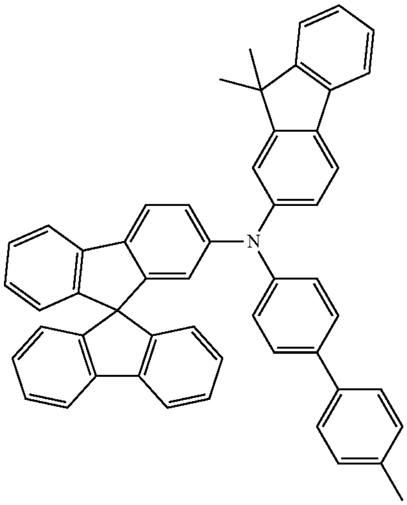

-continued
HT39
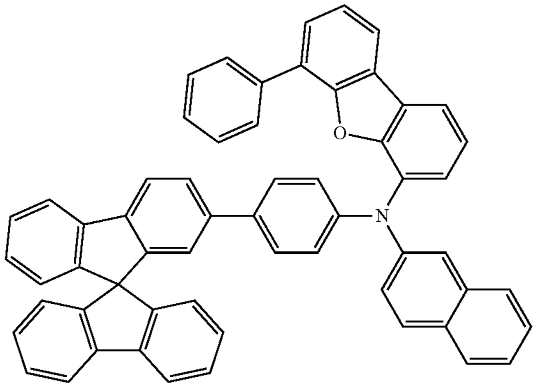
HT40
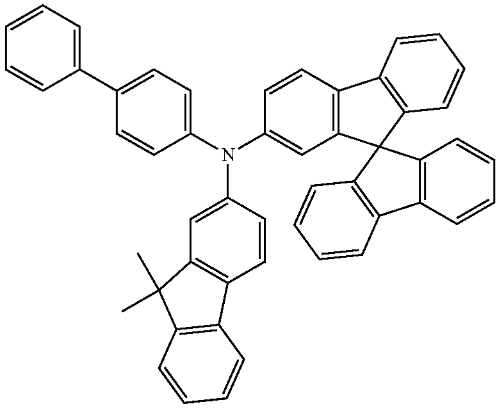
HT41
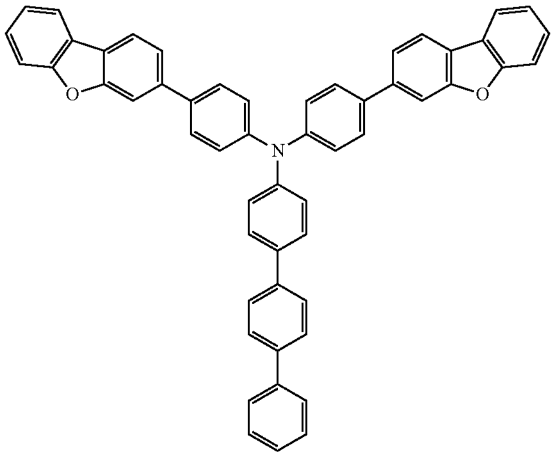
HT42
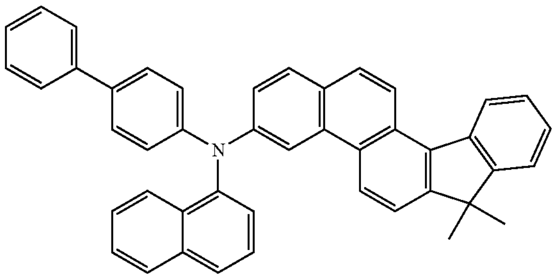
HT43
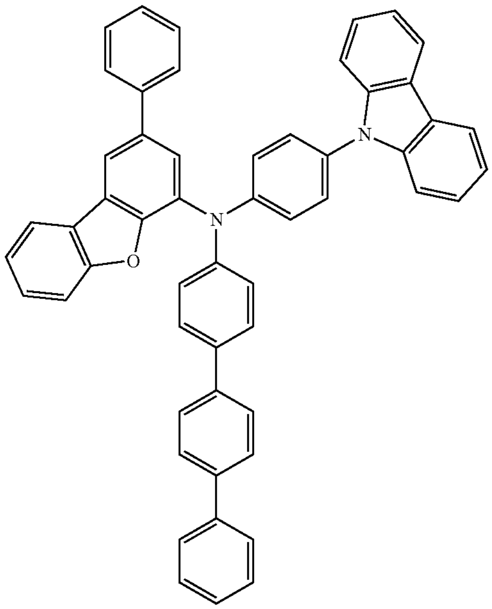
HT44
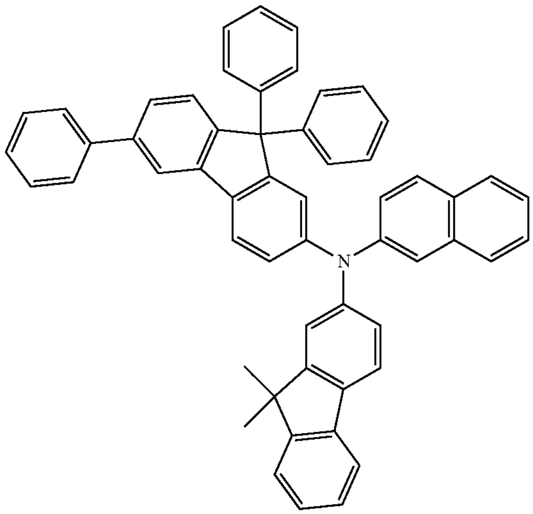

-continued
HT45
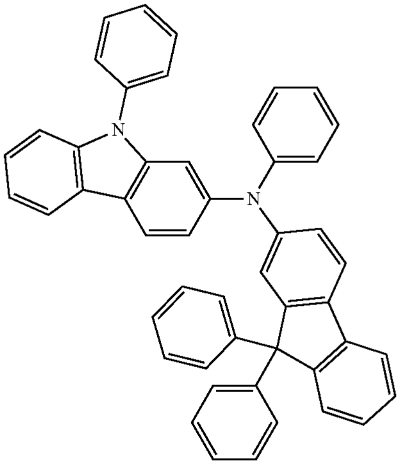
HT46
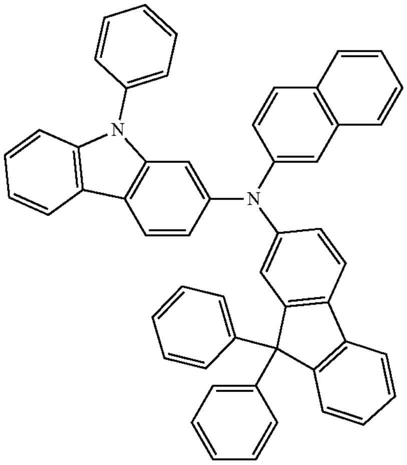
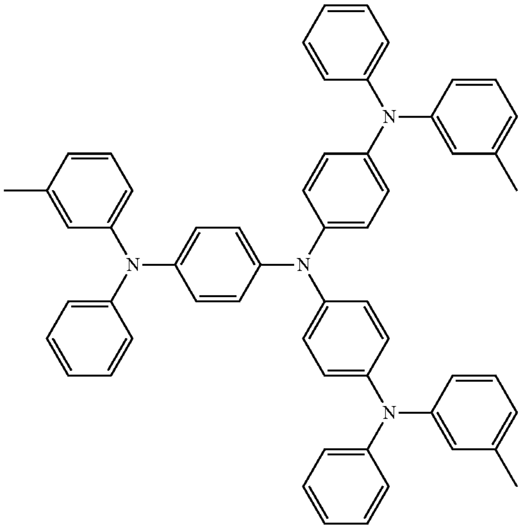
m-MTDATA
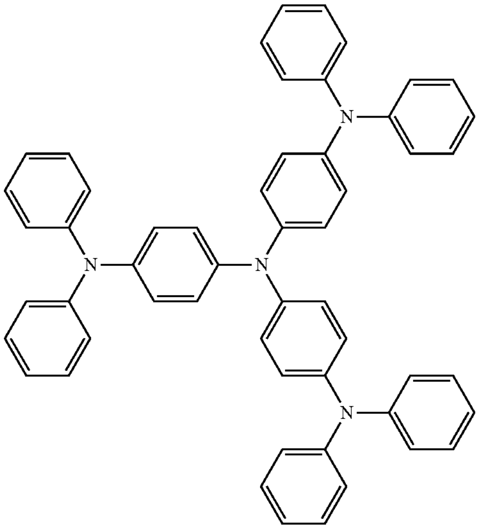
TDATA
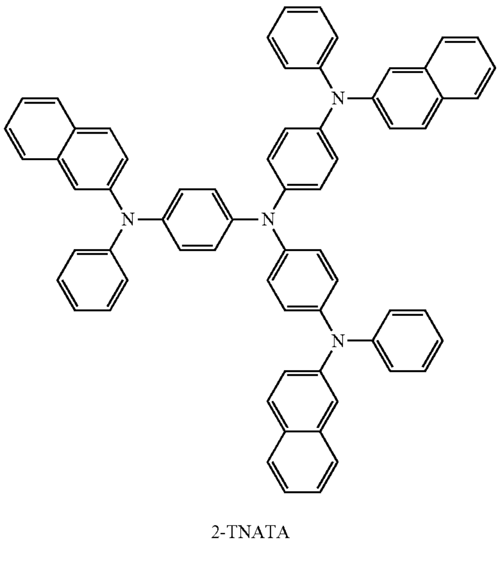
2-TNATA
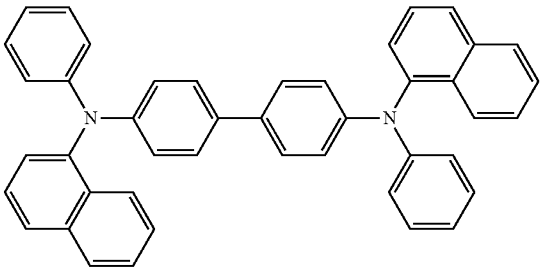
NPB -continued
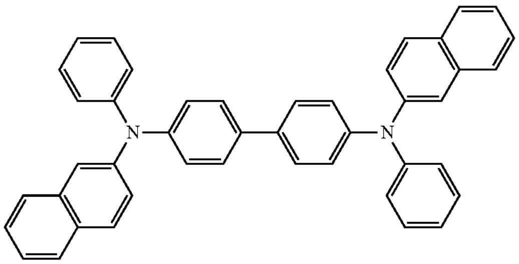
β-NPB
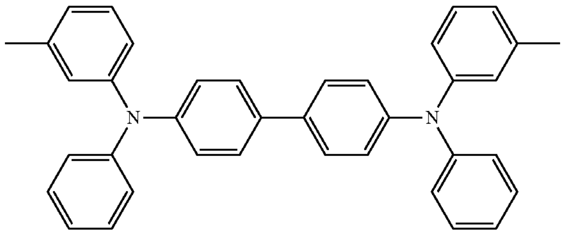
TPD
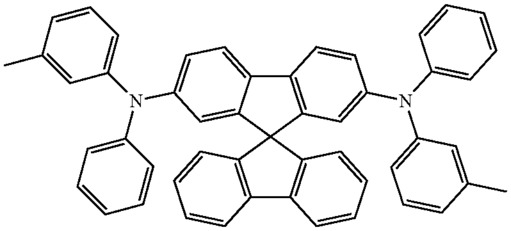
Spiro-TPD
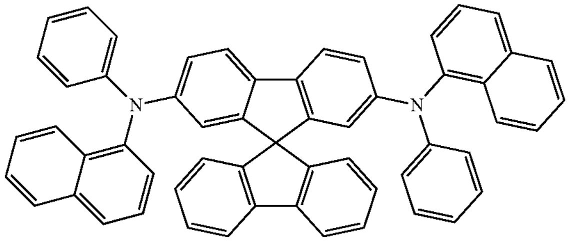
Spiro-NPB
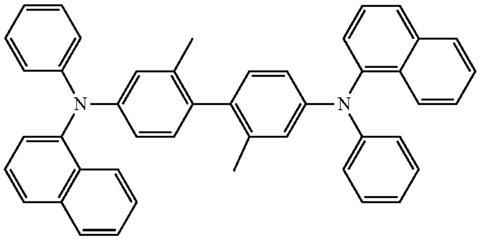
methylated-NPB
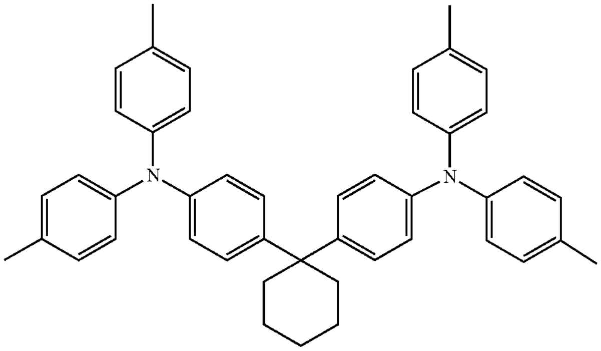
TAPC
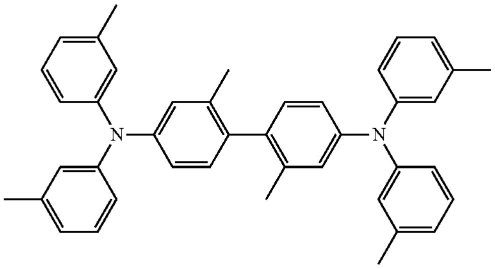
HMTPD
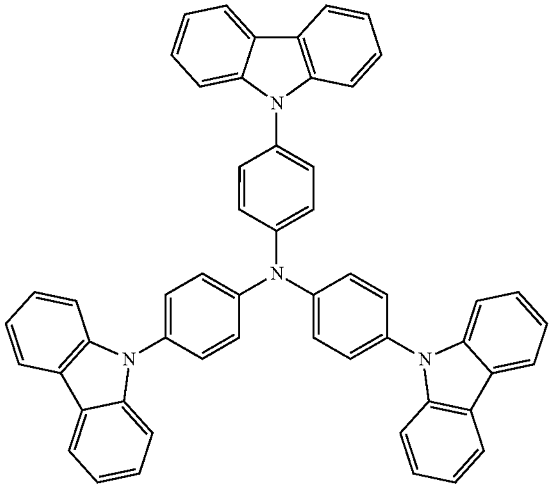
TCTA -continued

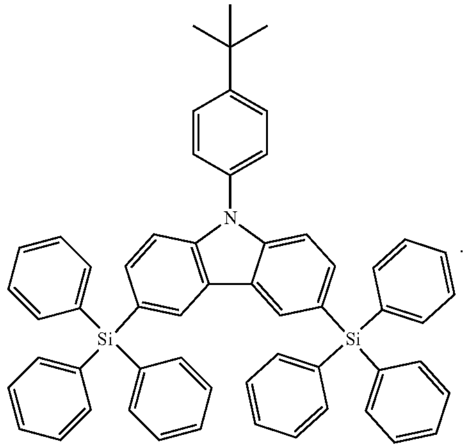

CzSi

A thickness of the hole transport region may be in a range of about 50 Å to about 10,000 Å, for example, about 100 Å to about 4,000 Å. When the hole transport region includes a hole injection layer, a hole transport layer, or any combination thereof, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within the ranges described above, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the leakage of electrons from the emission layer to a hole transport region. Materials that may be included in the hole transport region may be included in the emission auxiliary layer and the electron blocking layer.

p-Dopant

The hole transport region may further include, in addition to these materials, a charge-generation material for the improvement of conductive properties. The charge-generation material may be uniformly or non-uniformly dispersed in the hole transport region (for example, in the form of a single layer consisting of a charge-generation material).

The charge-generation material may be, for example, a p-dopant.

In an embodiment, the lowest unoccupied molecular orbital (LUMO) energy level of the p-dopant may be −3.5 eV or less.

In an embodiment, the p-dopant may include a quinone derivative, a cyano group-containing compound, a compound containing element EL1 and element EL2, or any combination thereof.

Examples of the quinone derivative may include TCNQ, F4-TCNQ, and/or the like.

Examples of the cyano group-containing compound may include HAT-CN, a compound represented by Formula 221, and/or the like.

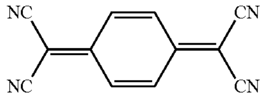

TCNQ

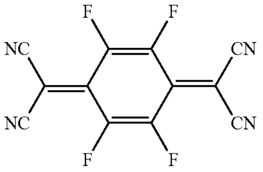

F4-TCNQ

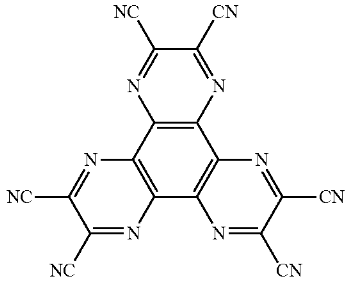

HAT-CN

Formula 221

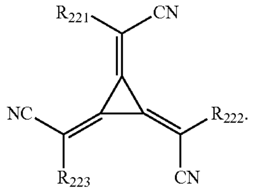

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof; or any combination thereof.

In the compound containing element EL1 and element EL2, element EL1 may be a metal, a metalloid, or any combination thereof, and element EL2 may be a non-metal, a metalloid, or any combination thereof.

Examples of the metal may include: an alkali metal (for example, lithium (Li), sodium (Na), potassium (K), rubidium (Rb), cesium (Cs), etc.); an alkaline earth metal (for example, beryllium (Be), magnesium (Mg), calcium (Ca), strontium (Sr), barium (Ba), etc.); a transition metal (for example, titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), etc.); a post-transition metal (for example, zinc (Zn), indium (In), tin (Sn), etc.); and a lanthanide metal (for example, lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), etc.).

Examples of the metalloid may include silicon (Si), antimony (Sb), and tellurium (Te).

Examples of the non-metal may include oxygen (O) and halogen (for example, F, Cl, Br, I, etc.).

In an embodiment, examples of the compound containing element EL1 and element EL2 may include a metal oxide, a metal halide (for example, metal fluoride, metal chloride, metal bromide, metal iodide, etc.), a metalloid halide (for example, metalloid fluoride, metalloid chloride, metalloid bromide, metalloid iodide, etc.), a metal telluride, or any combination thereof.

Examples of the metal oxide may include tungsten oxide (for example, WO, $W_2O_3$, $WO_2$, $WO_3$, $W_2O_5$, etc.), vanadium oxide (for example, VO, $V_2O_3$, $VO_2$, $V_2O_5$, etc.), molybdenum oxide (MoO, $Mo_2O_3$, $MoO_2$, $MoO_3$, $Mo_2O_5$, etc.), and rhenium oxide (for example, $ReO_3$, etc.).

Examples of the metal halide may include alkali metal halide, alkaline earth metal halide, transition metal halide, post-transition metal halide, and lanthanide metal halide.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, and Csl.

Examples of the alkaline earth metal halide may include $BeF_2$, $MgF_2$, $CaF_2$, $SrF_2$, $BaF_2$, $BeCl_2$, $MgCl_2$, $CaCl_2$), $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, and $BaI_2$.

Examples of the transition metal halide may include titanium halide (for example, $TiF_4$, $TiCl_4$, $TiBr_4$, $TiI_4$, etc.), zirconium halide (for example, $ZrF_4$, $ZrCl_4$, $ZrBr_4$, $Zr_{14}$, etc.), hafnium halide (for example, $HfF_4$, $HfCl_4$, $HfBr_4$, $HfI_4$, etc.), vanadium halide (for example, $VF_3$, $VCl_3$, $VBr_3$, $VI_3$, etc.), niobium halide (for example, $NbF_3$, $NbCl_3$, $NbBr_3$, $NbI_3$, etc.), tantalum halide (for example, $TaF_3$, $TaCl_3$, $TaBr_3$, $TaI_3$, etc.), chromium halide (for example, $CrF_3$, $CrCl_3$, $CrBr_3$, $CrI_3$, etc.), molybdenum halide (for example, $MoF_3$, $MoCl_3$, $MoBr_3$, $MoI_3$, etc.), tungsten halide (for example, $WF_3$, $WCl_3$, $WBr_3$, $WI_3$, etc.), manganese halide (for example, $MnF_2$, $MnCl_2$, $MnBr_2$, $MnI_2$, etc.), technetium halide (for example, $TcF_2$, $TcCl_2$, $TcBr_2$, $TcI_2$, etc.), rhenium halide (for example, $ReF_2$, $ReCl_2$, $ReBr_2$, $ReI_2$, etc.), iron halide (for example, $FeF_2$, $FeCl_2$, $FeBr_2$, $Fe_{12}$, etc.), ruthenium halide (for example, $RuF_2$, $RuCl_2$, $RuBr_2$, $RuI_2$, etc.), osmium halide (for example, $OsF_2$, $OsCl_2$, $OsBr_2$, $OsI_2$, etc.), cobalt halide (for example, $CoF_2$, $CoCl_2$, $CoBr_2$, $CoI_2$, etc.), rhodium halide (for example, $RhF_2$, $RhCl_2$, $RhBr_2$, $RhI_2$, etc.), iridium halide (for example, $IrF_2$, $IrCl_2$, $IrBr_2$, $IrI_2$, etc.), nickel halide (for example, $NiF_2$, $NiCl_2$, $NiBr_2$, $NiI_2$, etc.), palladium halide (for example, $PdF_2$, $PdCl_2$, $PdBr_2$, $PdI_2$, etc.), platinum halide (for example, $PtF_2$, $PtCl_2$, $PtBr_2$, $PtI_2$, etc.), copper halide (for example, CuF, CuCl, CuBr, CuI, etc.), silver halide (for example, AgF, AgCl, AgBr, AgI, etc.), and gold halide (for example, AuF, AuCl, AuBr, AuI, etc.).

Examples of the post-transition metal halide may include zinc halide (for example, $ZnF_2$, $ZnCl_2$, $ZnBr_2$, $ZnI_2$, etc.), indium halide (for example, $InI_3$, etc.), and tin halide (for example, $SnI_2$, etc.).

Examples of the lanthanide metal halide may include YbF, $YbF_2$, $YbF_3$, $SmF_3$, YbCl, $YbCl_2$, $YbCl_3$ $SmCl_3$, YbBr, $YbBr_2$, $YbBr_3$, $SmBr_3$, YbI, $YbI_2$, $YbI_3$, and $SmI_3$.

Examples of the metalloid halide may include antimony halide (for example, $SbCl_5$, etc.).

Examples of the metal telluride may include alkali metal telluride (for example, $Li_2Te$, a $Na_2Te$, $K_2Te$, $Rb_2Te$, $Cs_2Te$, etc.), alkaline earth metal telluride (for example, BeTe, MgTe, CaTe, SrTe, BaTe, etc.), transition metal telluride (for example, $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, etc.), post-transition metal telluride (for example, ZnTe, etc.), and lanthanide metal telluride (for example, LaTe, CeTe, PrTe, NdTe, PmTe, EuTe, GdTe, TbTe, DyTe, HoTe, ErTe, TmTe, YbTe, LuTe, etc.).

Emission Layer in Interlayer 130

When the light-emitting device 10 is a full-color light-emitting device, the emission layer may be patterned into a red emission layer, a green emission layer, and/or a blue emission layer, according to a sub-pixel. In one or more embodiments, the emission layer may have a stacked structure of two or more layers of a red emission layer, a green emission layer, and a blue emission layer, in which the two or more layers contact each other or are separated from each other. In one or more embodiments, the emission layer may include two or more materials of a red light-emitting material, a green light-emitting material, and a blue light-emitting material, in which the two or more materials are mixed with each other in a single layer to emit white light. In an embodiment, the emission layer may emit blue light.

In an embodiment, the emission layer may include a first compound represented by Formula 1 and a second compound represented by Formula 2 as described herein.

The emission layer may include a host and a dopant.

In an embodiment, the host may include the first compound and the second compound. In an embodiment, the dopant may include a phosphorescent dopant, a fluorescent dopant, a delayed fluorescence material, or any combination thereof.

The phosphorescent dopant, the fluorescent dopant, and/or the like further included in the emission layer are the same as described below.

An amount of the dopant in the emission layer may be from about 0.01 to about 15 parts by weight based on 100 parts by weight of the host.

In one or more embodiments, the emission layer may include a quantum dot.

In one embodiment, the emission layer may include a delayed fluorescence material. The delayed fluorescence material may act as a host or a dopant in the emission layer.

A thickness of the emission layer may be in a range of about 100 Å to about 1,000 Å, for example, about 200 Å to about 600 Å. When the thickness of the emission layer is within the ranges described above, suitable (e.g., excellent) light-emission characteristics may be obtained without a substantial increase in driving voltage.

Host

The host may further include a host other than the first compound and the second compound. In an embodiment, the host may further include a carbazole-containing compound, an anthracene-containing compound, a triazine-containing compound, or any combination thereof. The host may further include, for example, a carbazole-containing compound and a triazine-containing compound.

In one or more embodiments, the host may further include a compound represented by Formula 301:

$$[Ar_{301}]_{xb11}\text{-}[(L_{301})_{xb1}\text{-}R_{301}]_{xb21} \qquad \text{Formula 301}$$

wherein, in Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, $—Si(Q_{301})(Q_{302})(Q_{303})$, $—N(Q_{301})(Q_{302})$, $—B(Q_{301})(Q_{302})$, $—C(=O)(Q_{301})$, $—S(=O)_2(Q_{301})$, or $—P(=O)(Q_{301})(Q_{302})$, xb21 may be an integer from 1 to 5, and $Q_{301}$ to $Q_{303}$ may each independently be the same as described in connection with $Q_1$.

In an embodiment, when xb11 in Formula 301 is 2 or more, two or more of $Ar_{301}$(s) may be linked to each other via a single bond.

In one or more embodiments, the host may further include a compound represented by Formula 301-1, a compound represented by Formula 301-2, or any combination thereof:

Formula 301-1

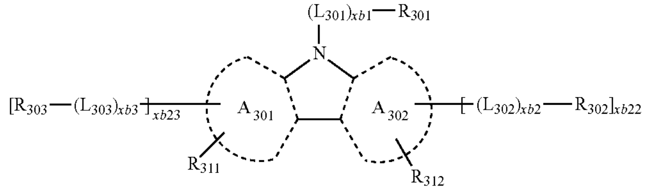

Formula 301-2

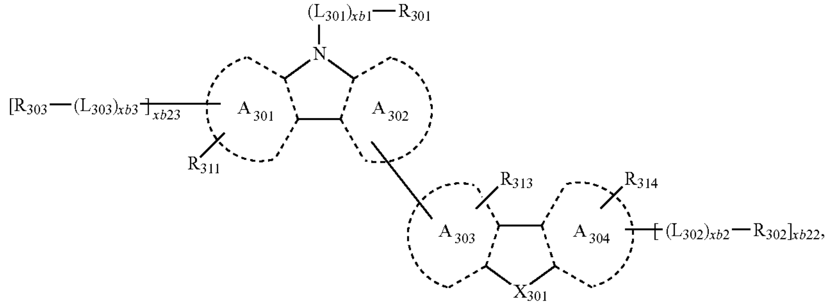

wherein, in Formulae 301-1 and 301-2, ring $A_{301}$ to ring $A_{304}$ may each independently be a $C_3$-$C_{60}$ carbocyclic group unsubstituted or substituted with at least one $R_{10a}$ or a $C_1$-$C_{10}$ heterocyclic group unsubstituted or substituted with at least one $R_{10a}$, $X_{301}$ may be O, S, $N\text{-}[(L_{304})_{xb4}\text{-}R_{304}]$, $C(R_{304})(R_{305})$, or $Si(R_{304})(R_{305})$, xb22 and xb23 may each independently be 0, 1, or 2, $L_{301}$, xb1, and $R_{301}$ may each independently be the same as described in the present specification, $L_{302}$ to $L_{304}$ may each independently be the same as described in connection with $L_{301}$, xb2 to xb4 may each independently be the same as described in connection with xb1, and $R_{302}$ to $R_{305}$ and $R_{311}$ to $R_{314}$ may each independently be the same as described in connection with $R_{301}$.

In one or more embodiments, the host may further include, other than the first compound and the second compound, an alkali earth metal complex, a post-transition metal complex, or any combination thereof. In an embodiment, the host may further include a Be complex (for example, Compound H55), an Mg complex, a Zn complex, or any combination thereof.

In an embodiment, the host may further include one of Compounds H1 to H124, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), or any combination thereof:

H1

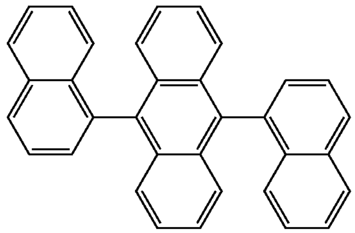

-continued
H2
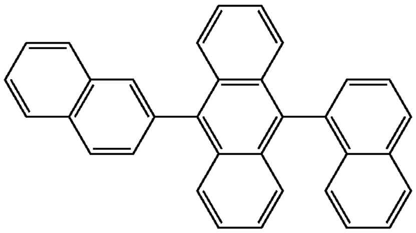
H3
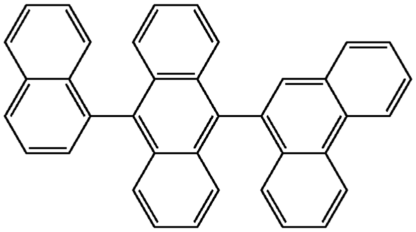
H4
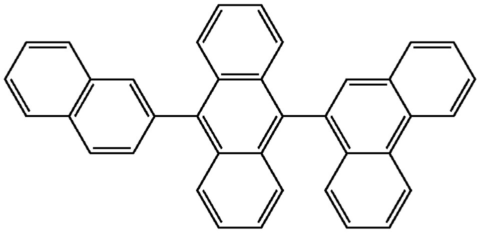
H5
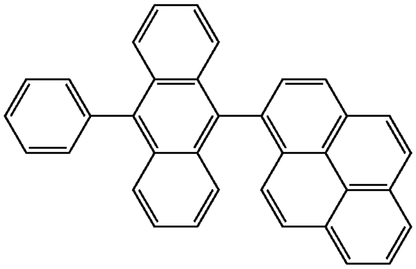
H6
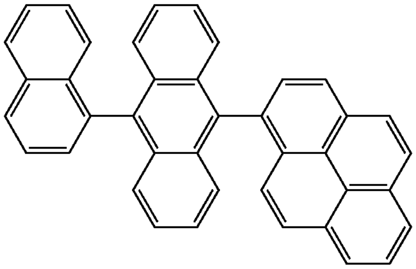
H7
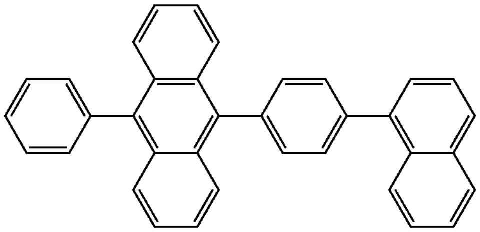
-continued
H8
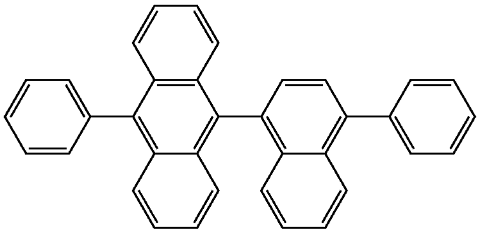
H9
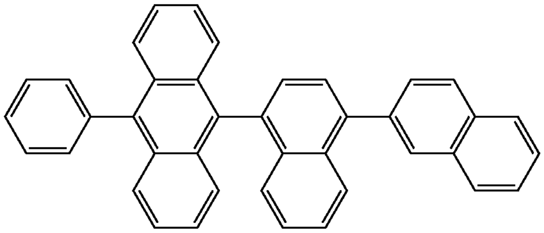
H10
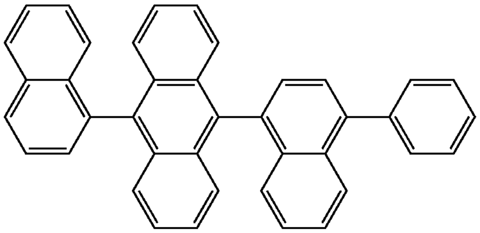
H11
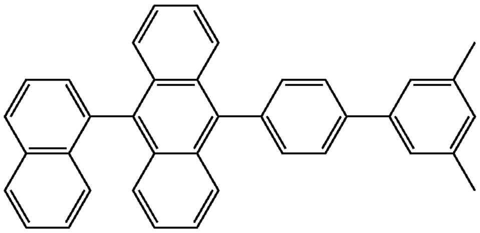
H12
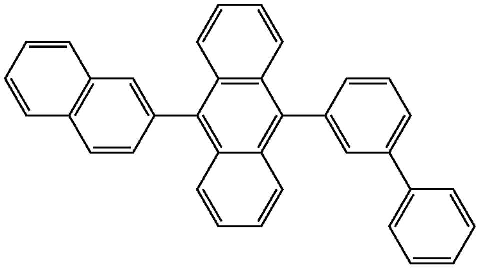
H13
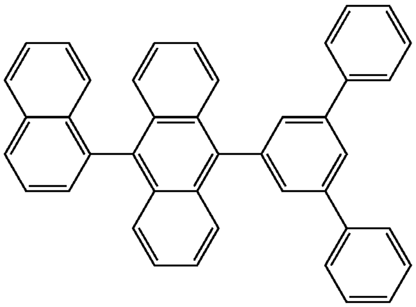

-continued
H14
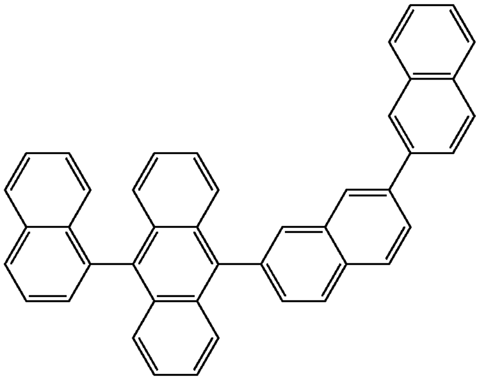
H15
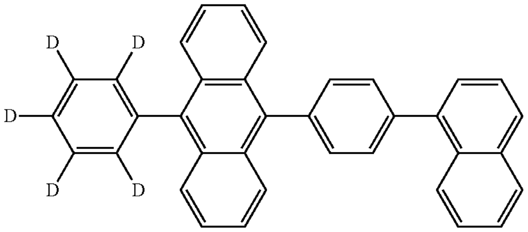
H16
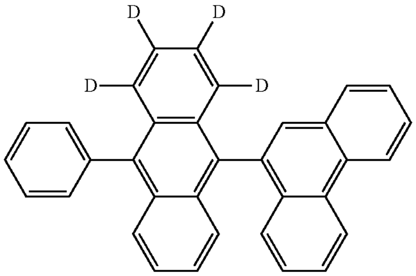
H17
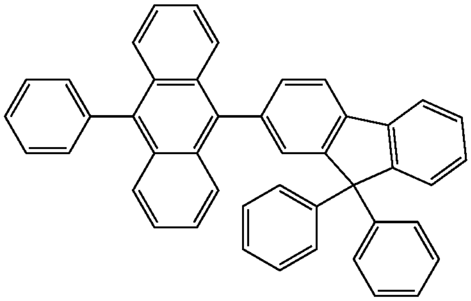
H18
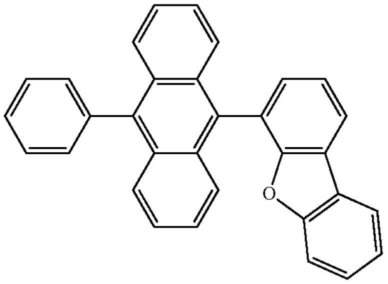
-continued
H19
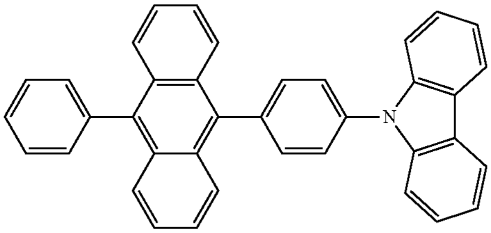
H20
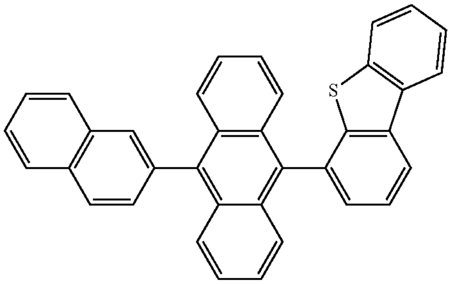
H21
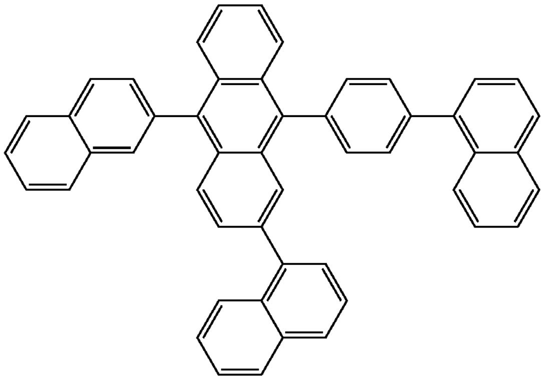
H22
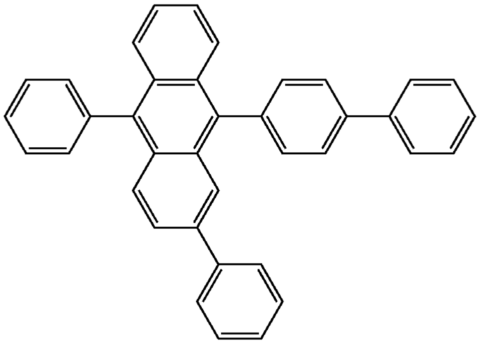

-continued
H23
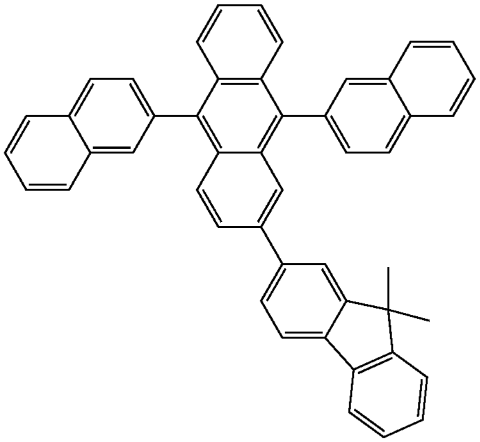
H24
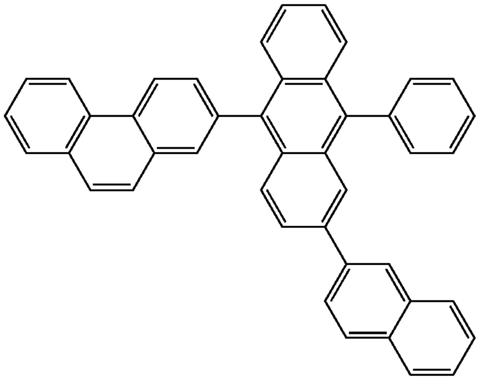
H25
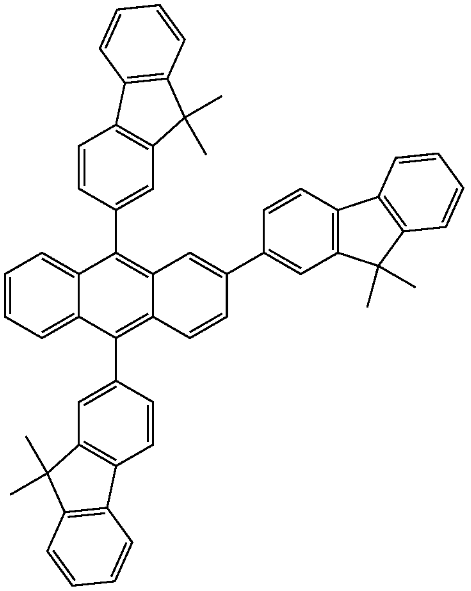
-continued
H26
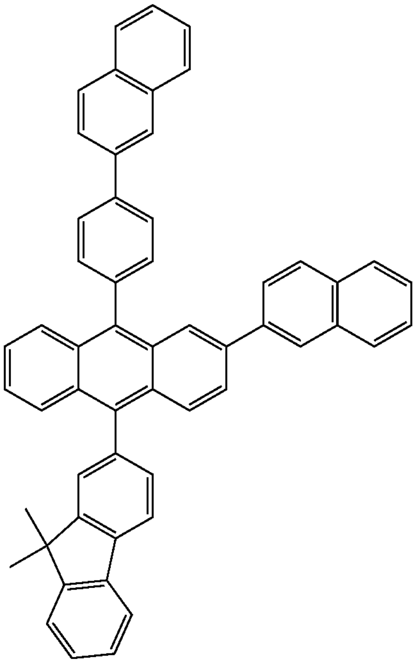
H27
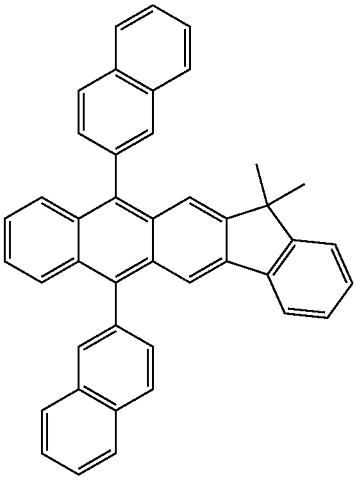
H28
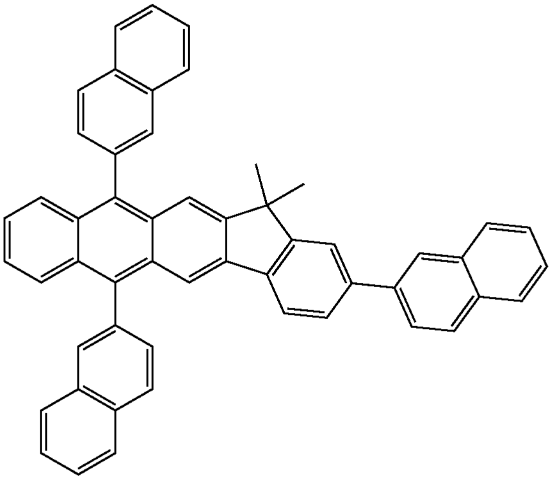

-continued
H29
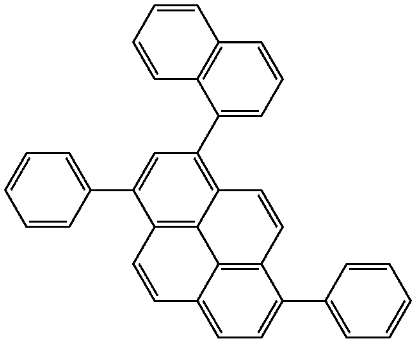
H30
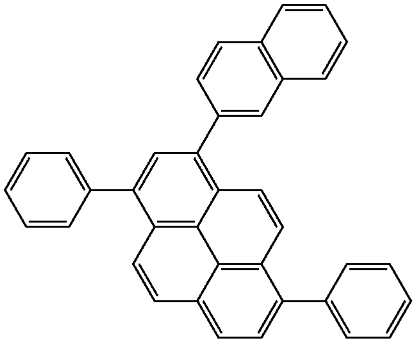
H31
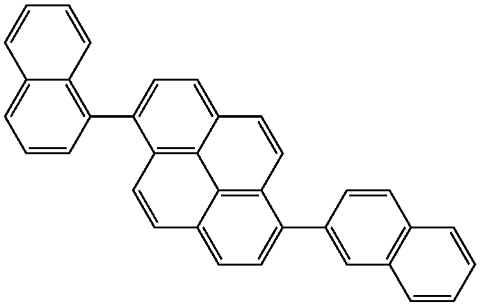
H32
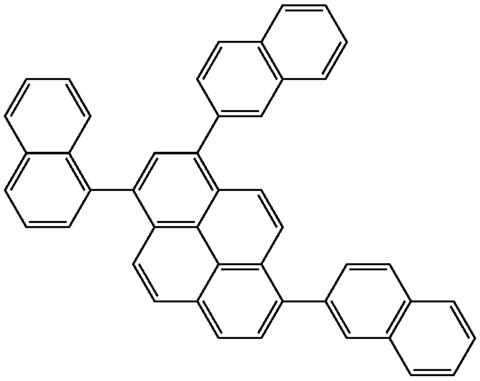
H33
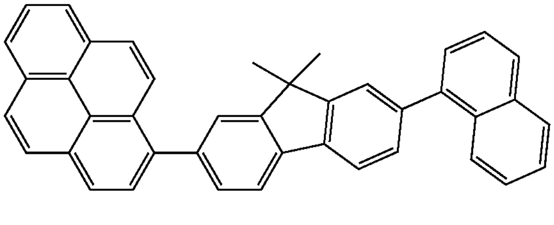
-continued
H34
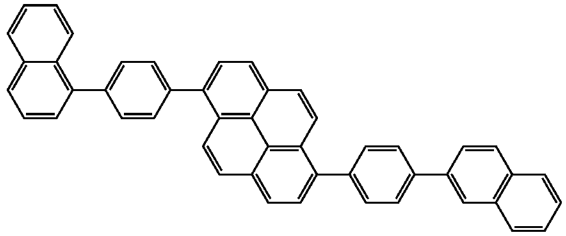
H35
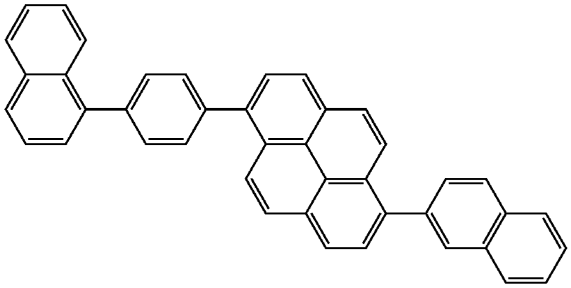
H36
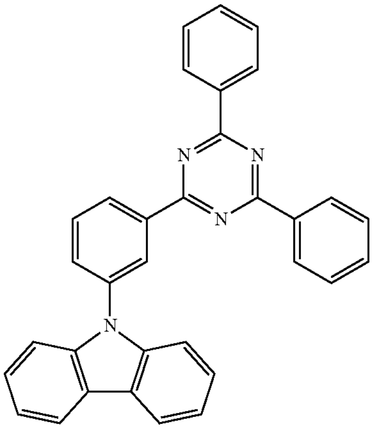
H37
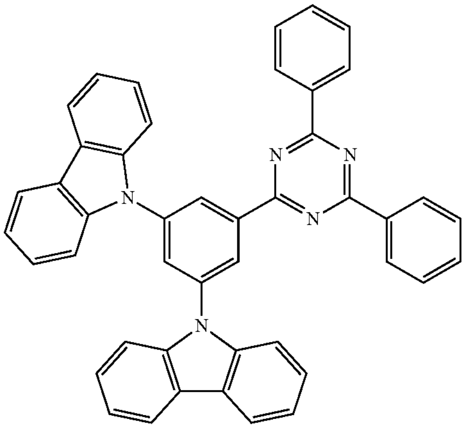

-continued
H38
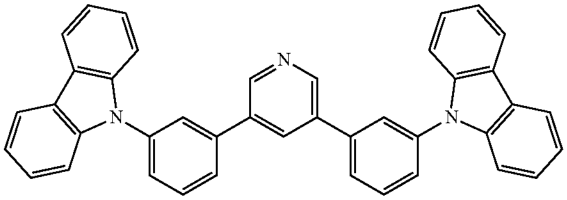
H39
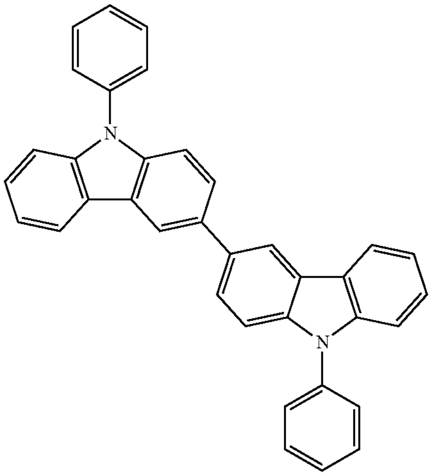
H40
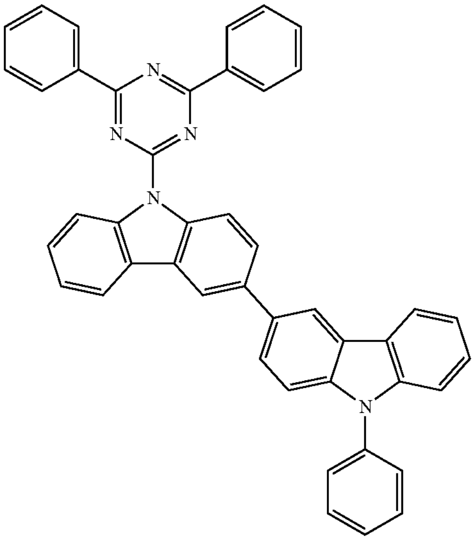
-continued
H41
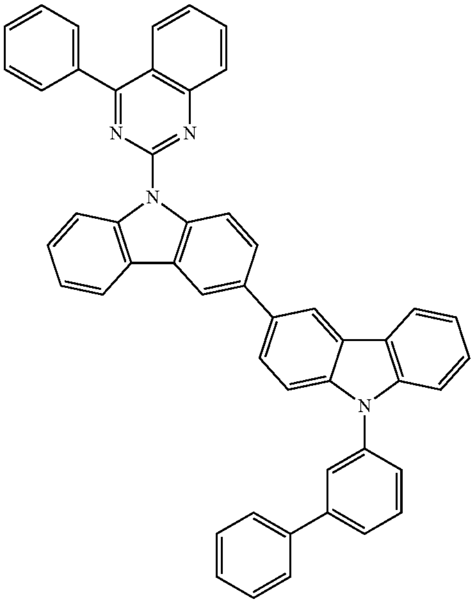
H42
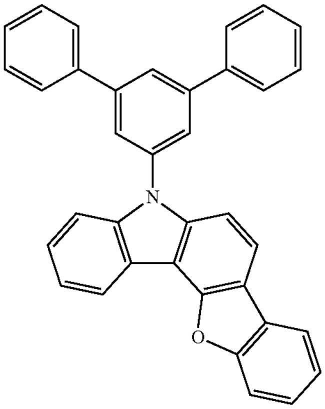
H43
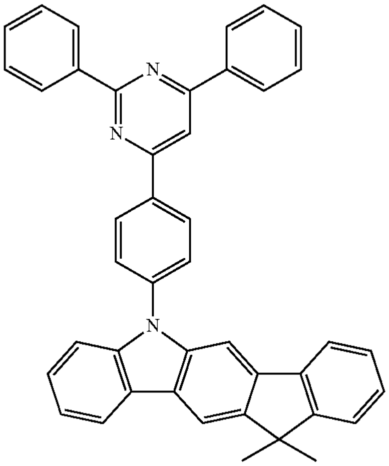

-continued
H44
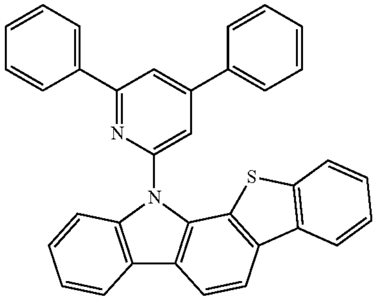
H45
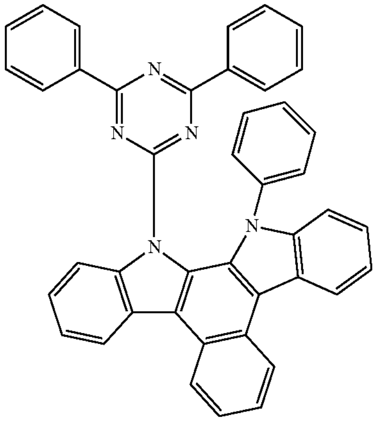
H46
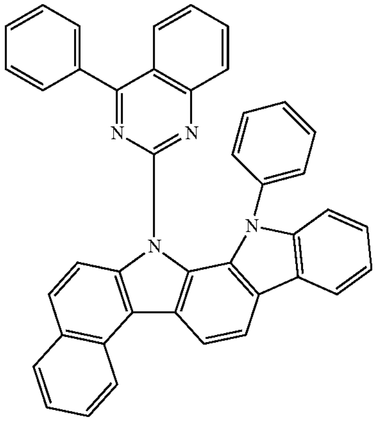
H47
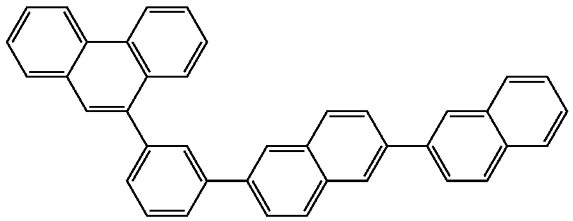
H48
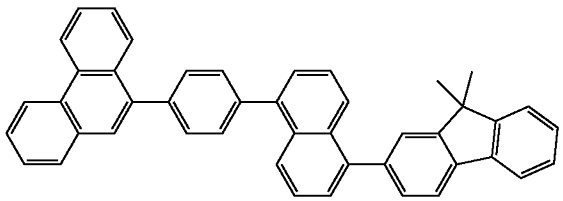
-continued
H49
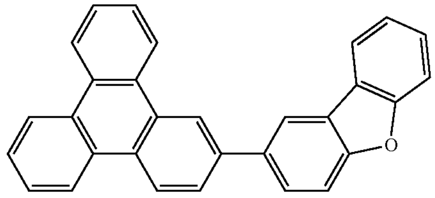
H50
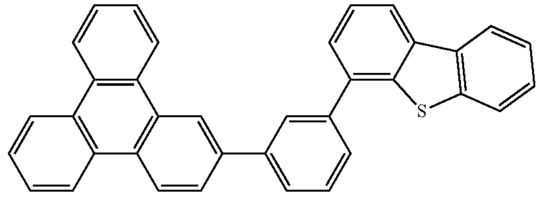
H51
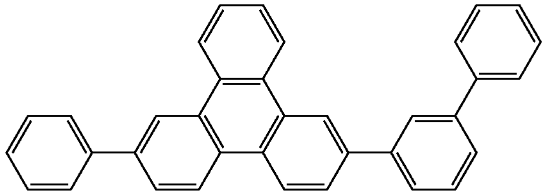
H52
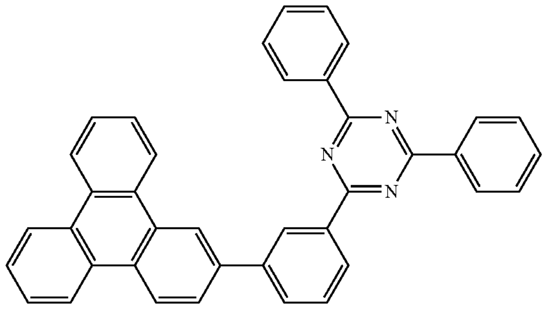
H53
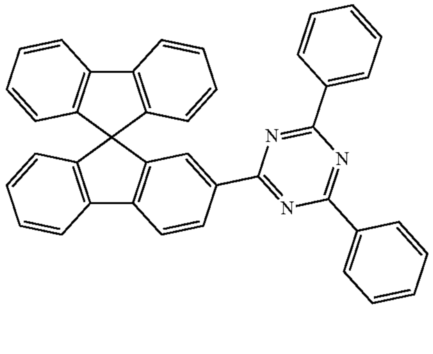

-continued
H54
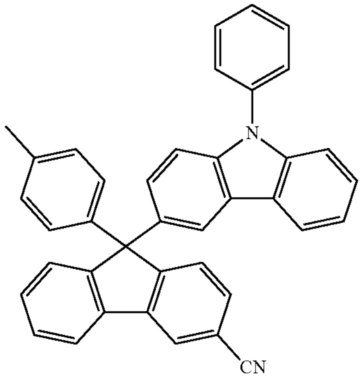
H55
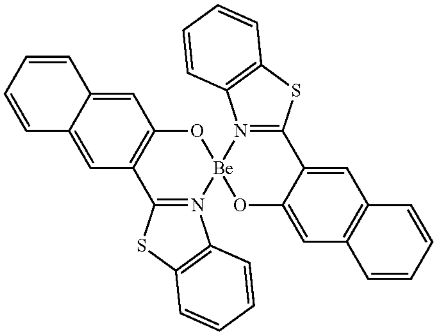
H56
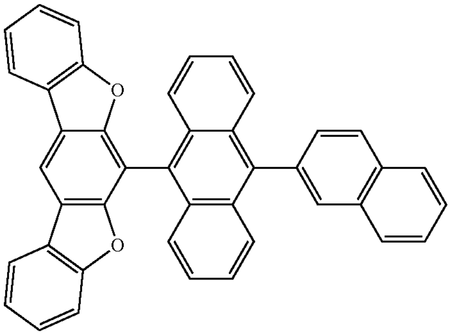
H57
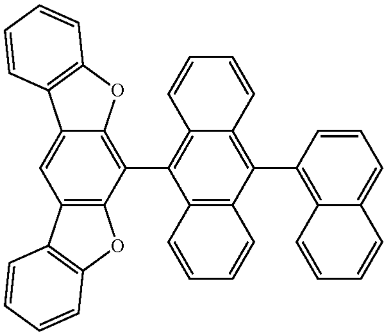
-continued
H58
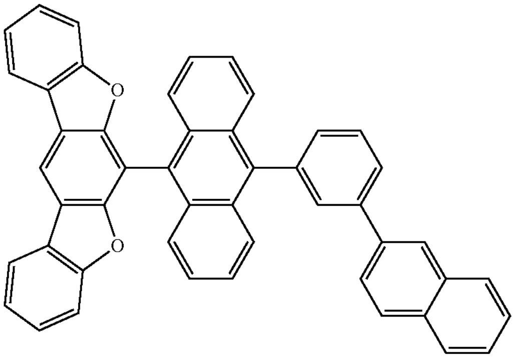
H59
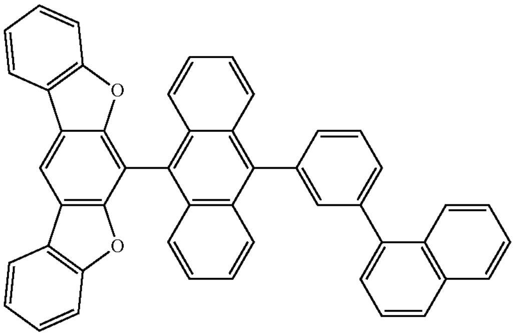
H60
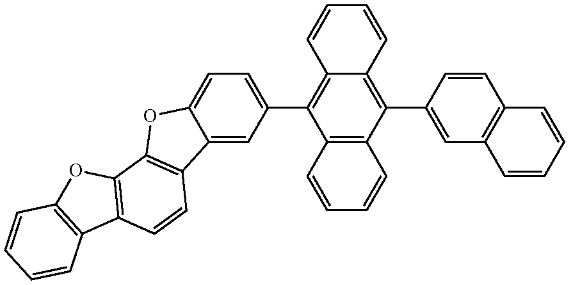
H61
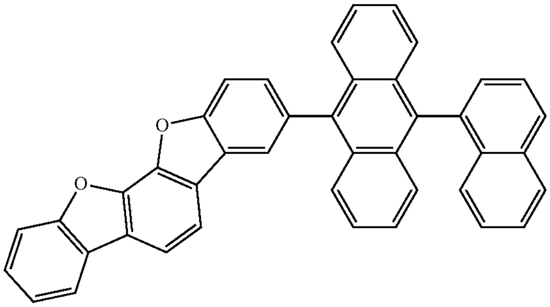

-continued
H62
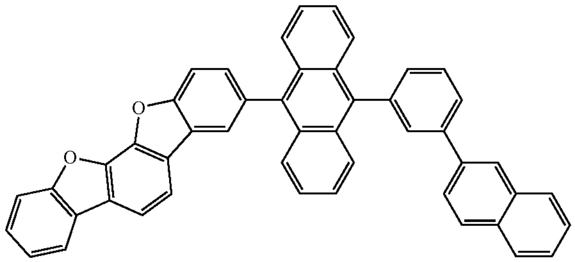
H63
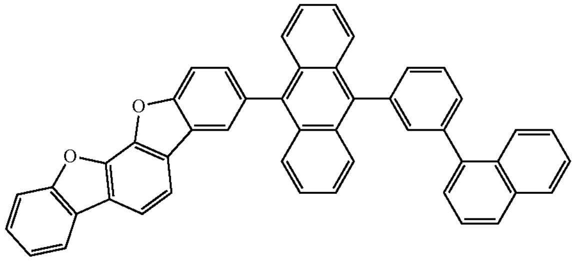
H64
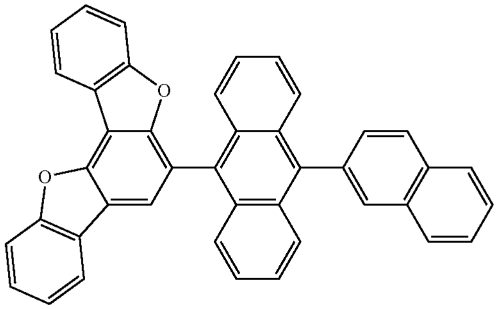
H65
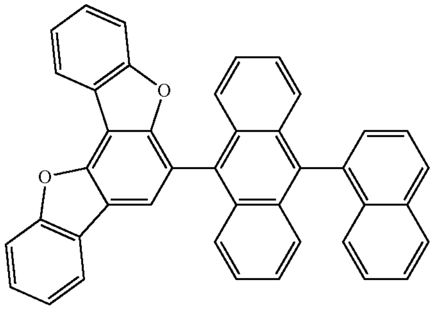
H66
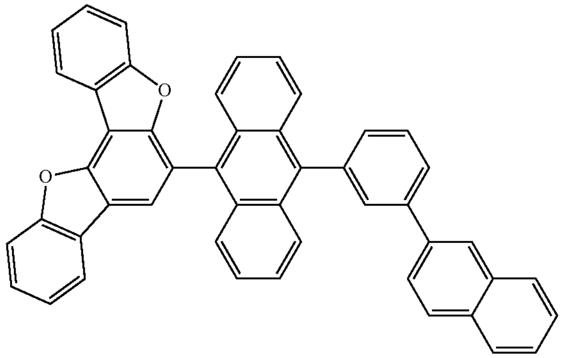
-continued
H67
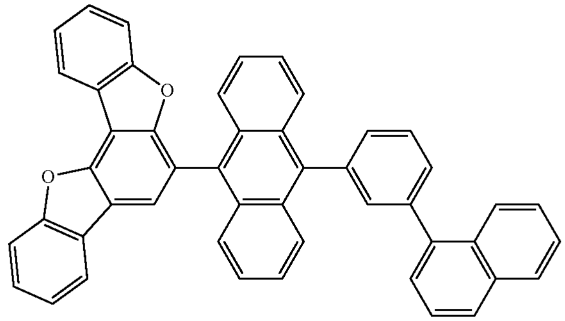
H68
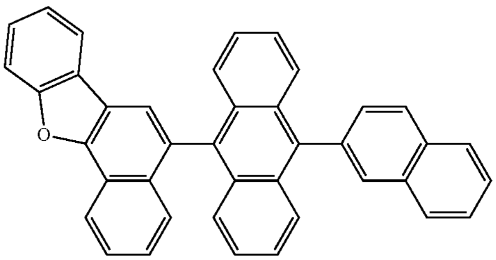
H69
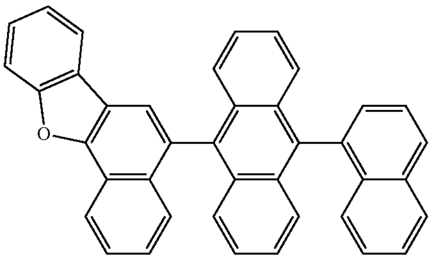
H70
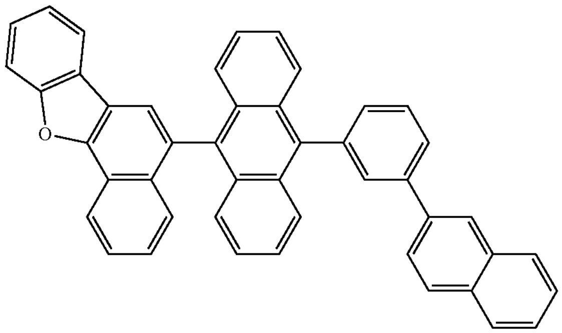
H71
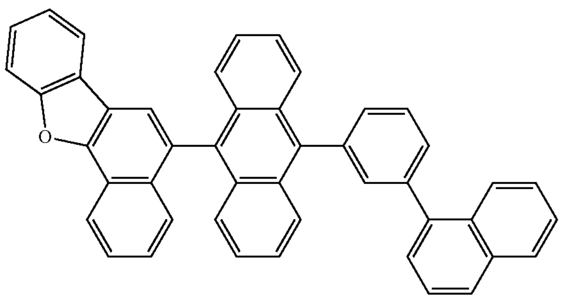

-continued
H72
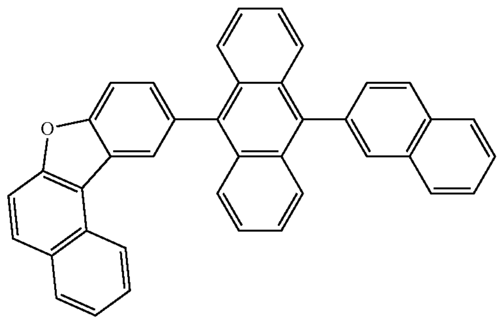
H73
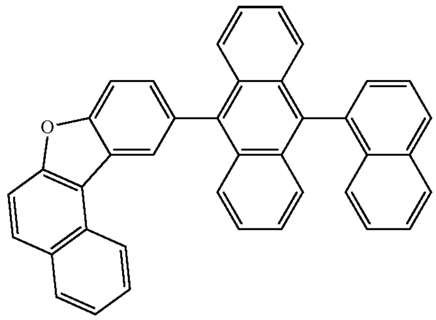
H74
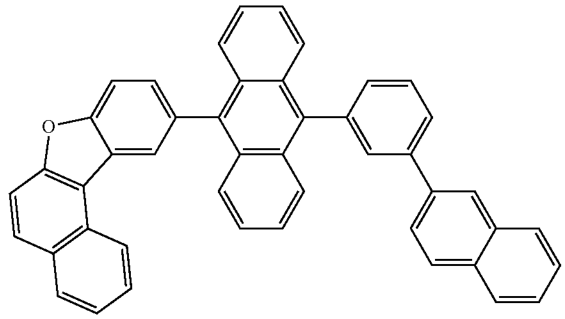
H75
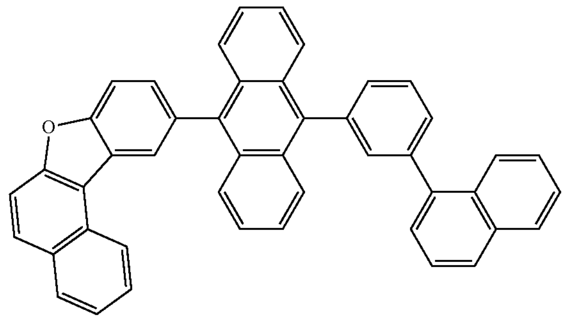
H76
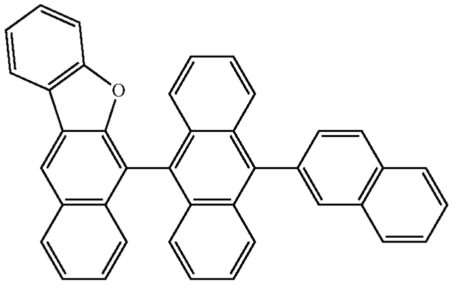
-continued
H77
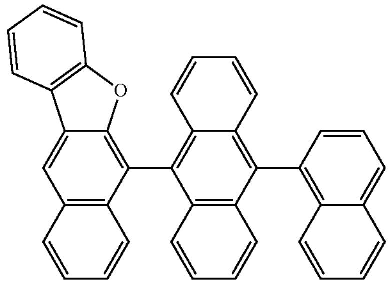
H78
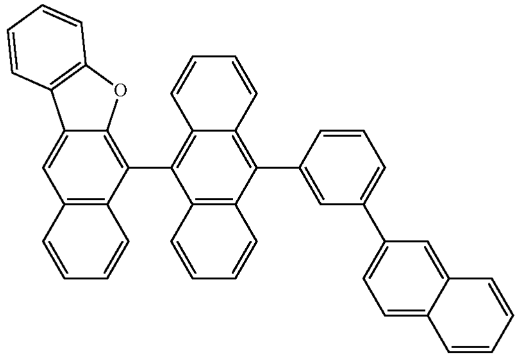
H79
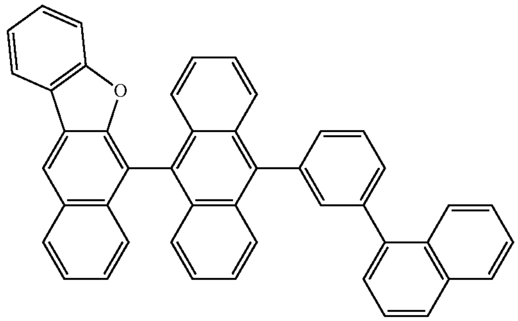
H80
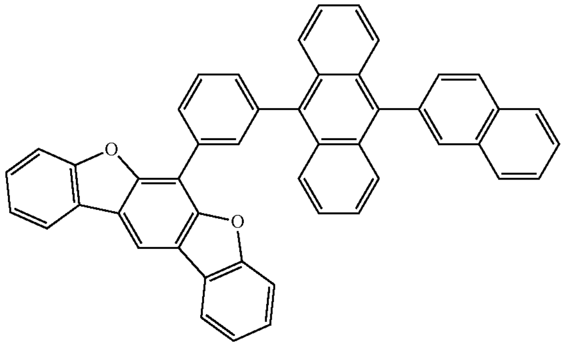

-continued
H81
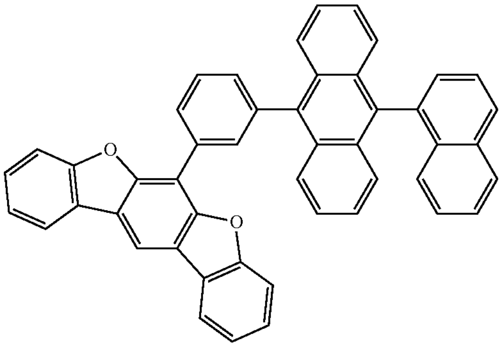
H82
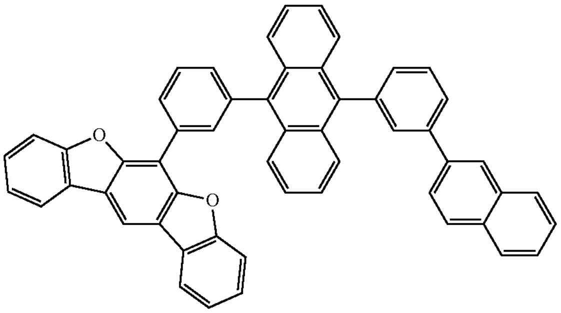
H83
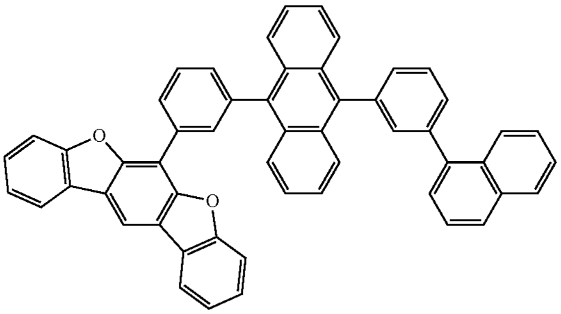
H84
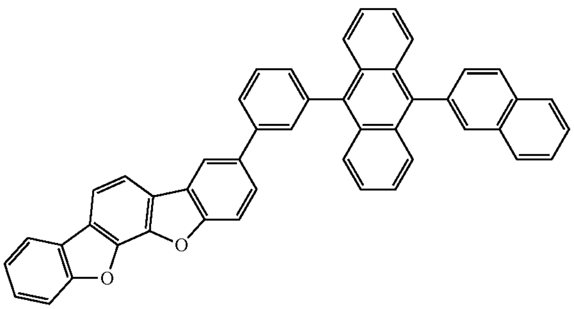
-continued
H85
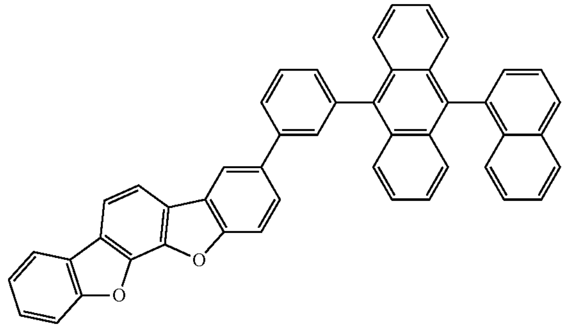
H86
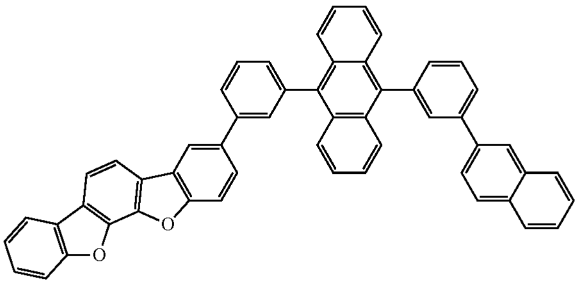
H87
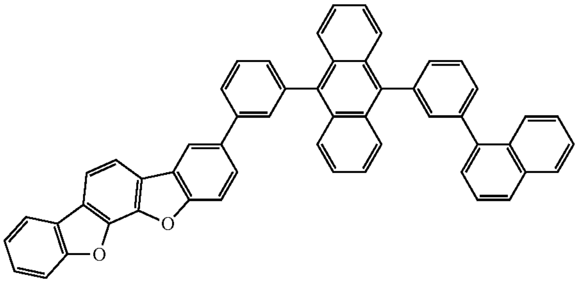
H88
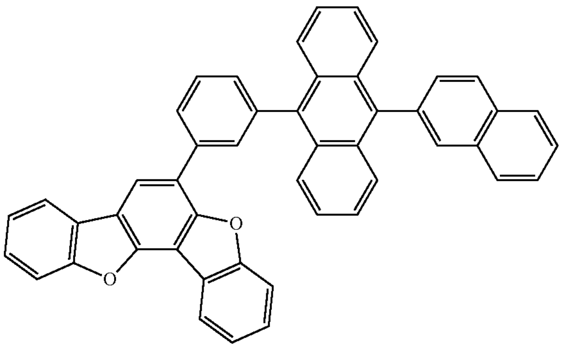

-continued
H89
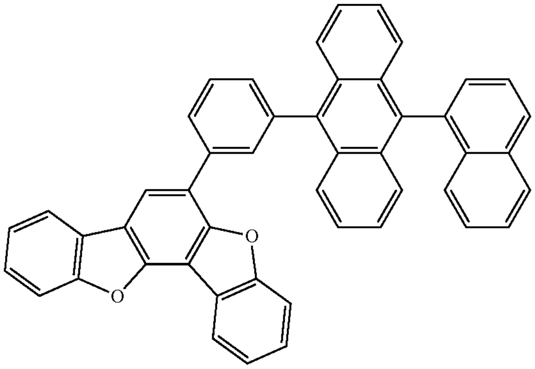
H90
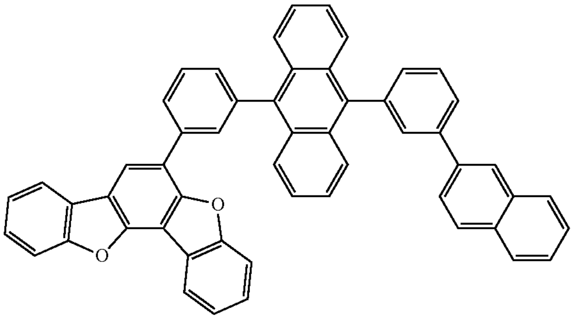
H91
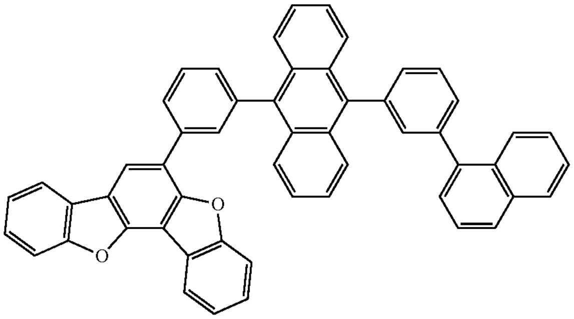
H92
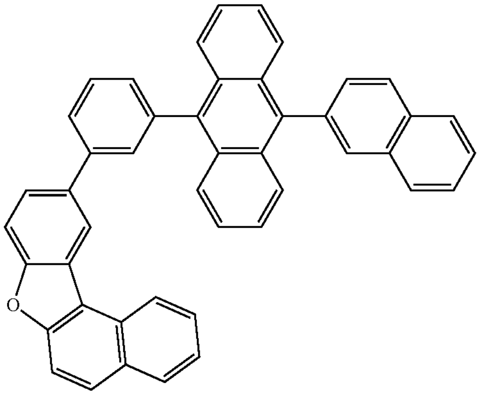
-continued
H93
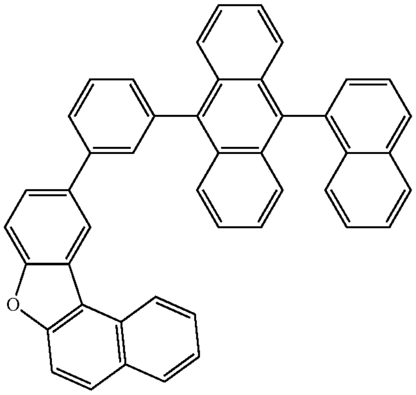
H94
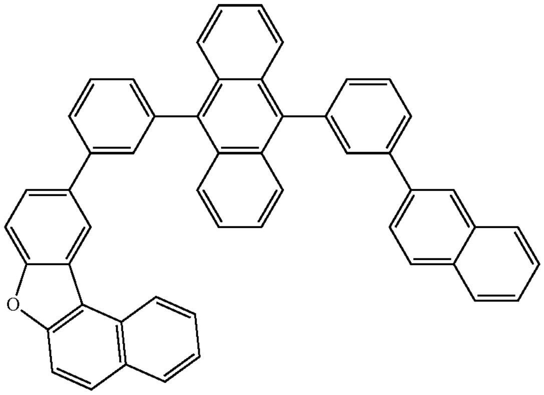
H95
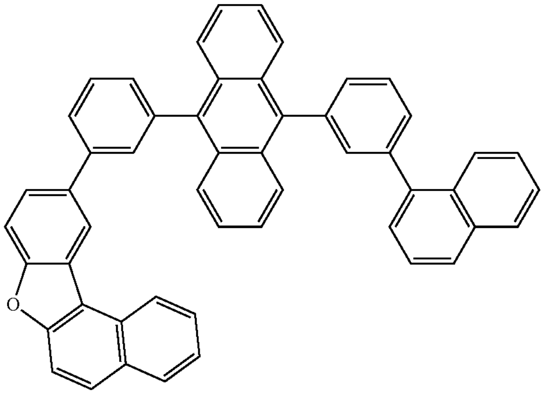
H96
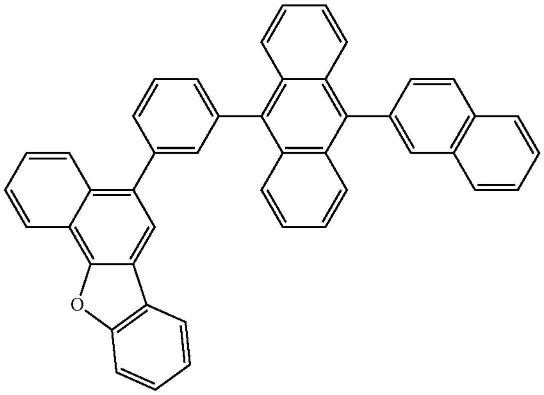

-continued
H97
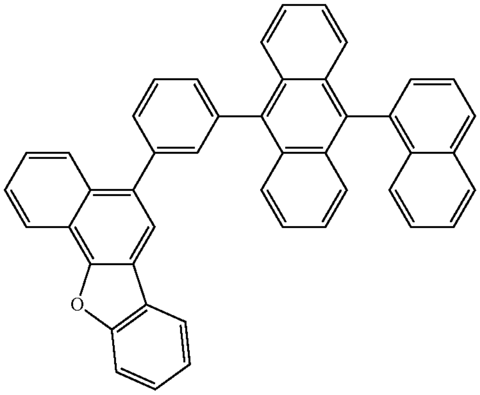
H98
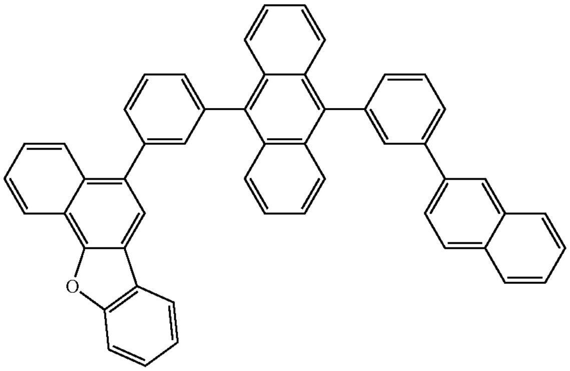
H99
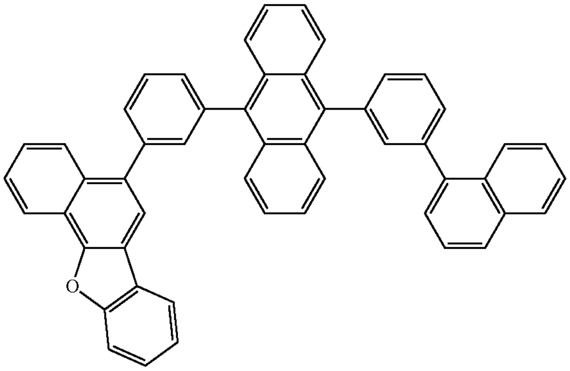
H100
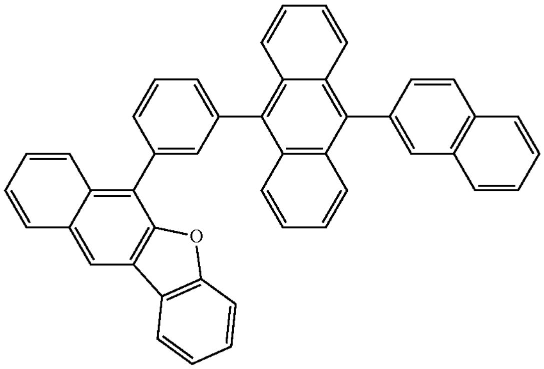
-continued
H101
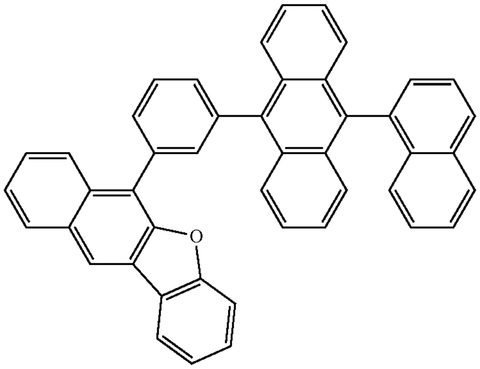
H102
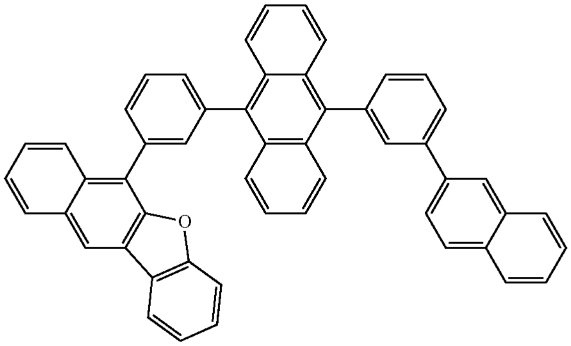
H103
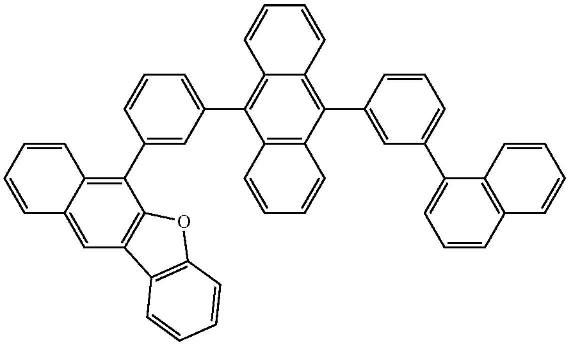
H104
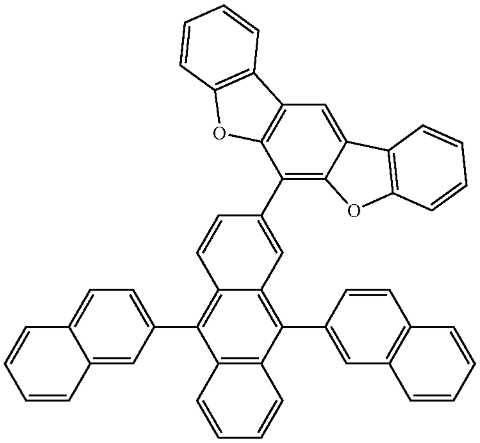

-continued
H105
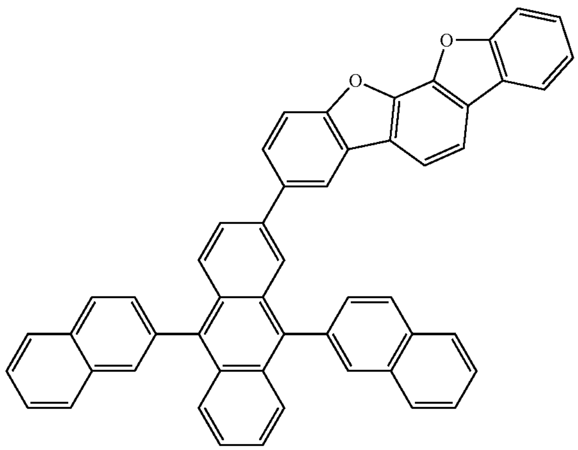
H106
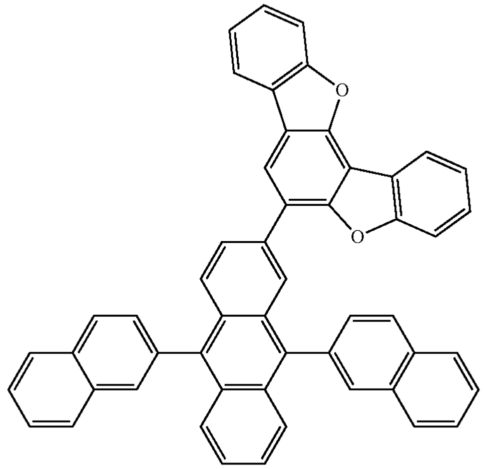
H107
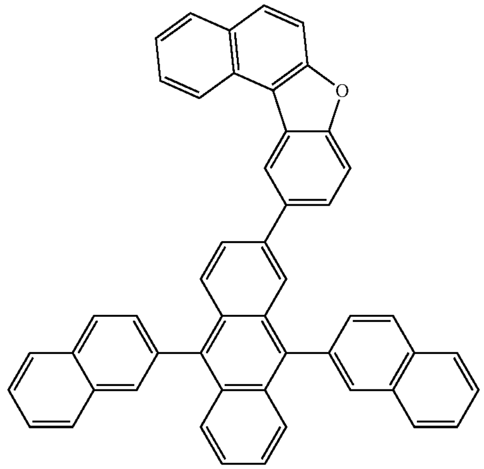
-continued
H108
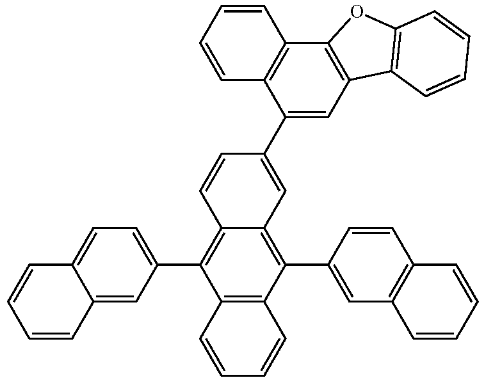
H109
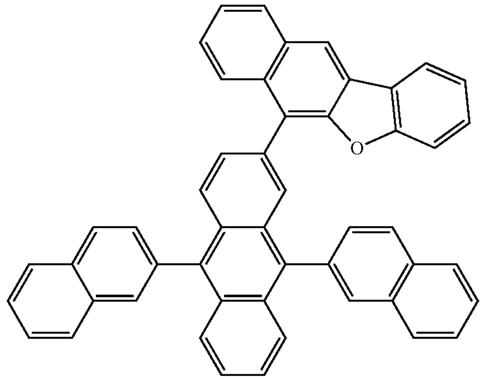
H110
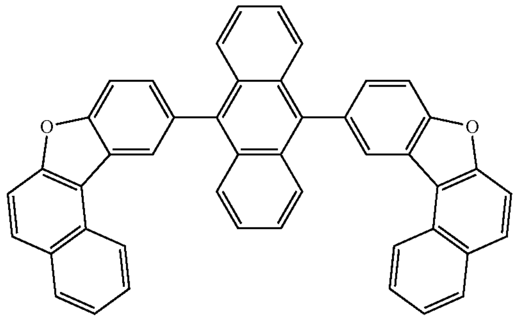
H111
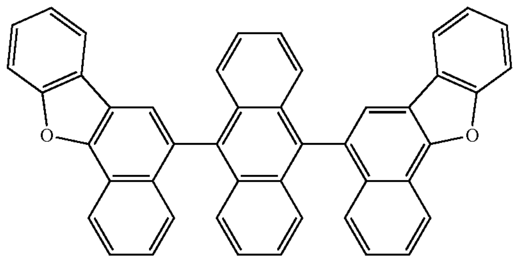

-continued
H112
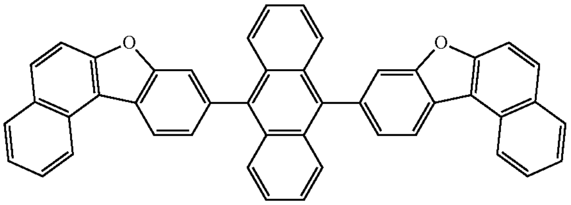
H113
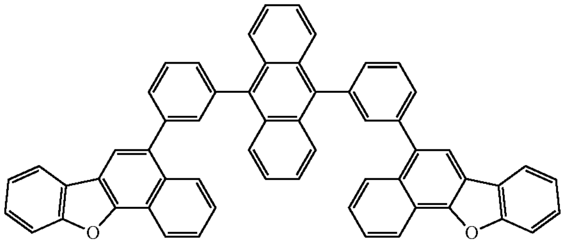
H114
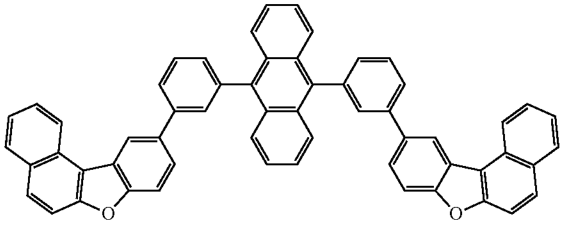
H115
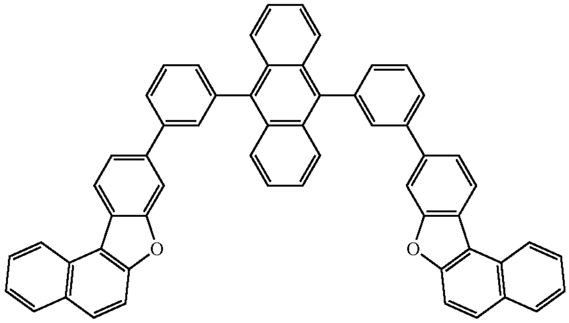
H116
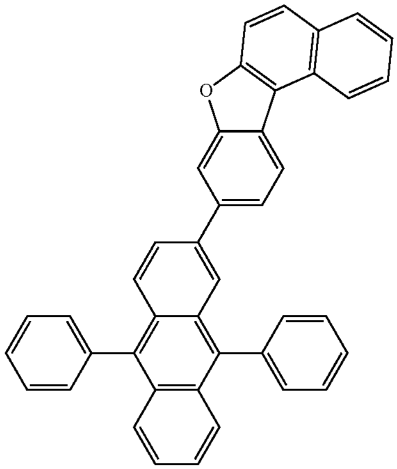
-continued
H117
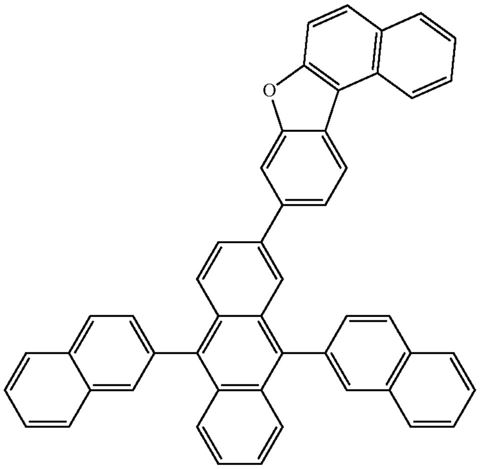
H118
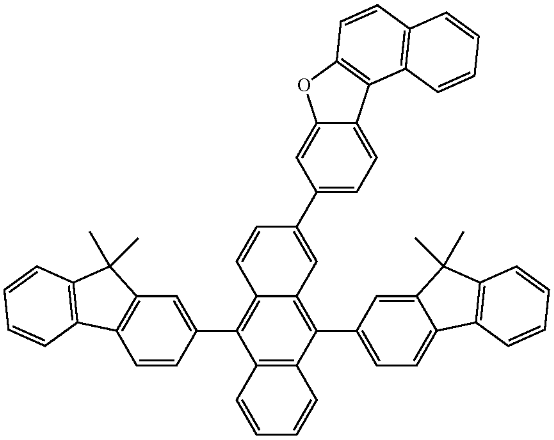
H119
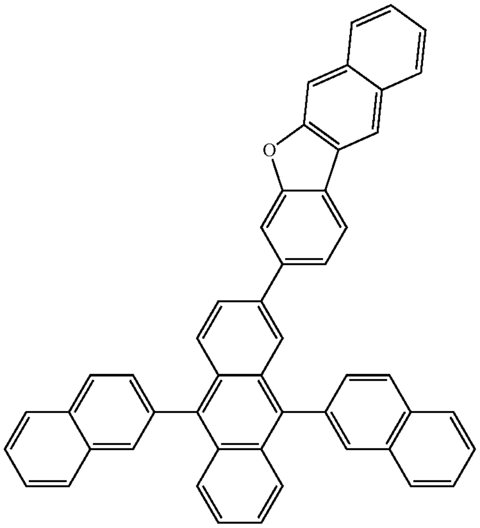

-continued

H120

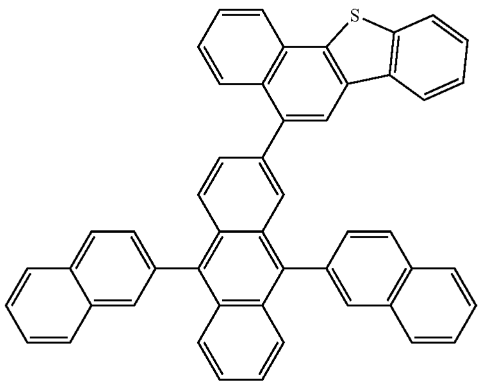

H121

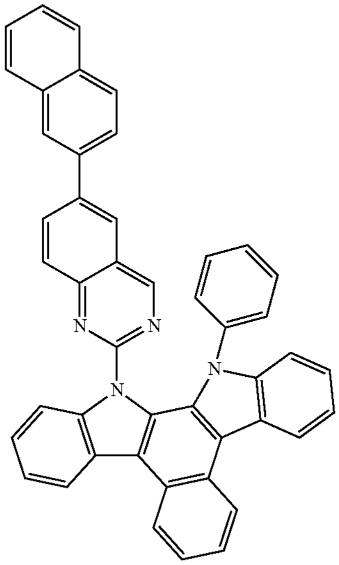

H122

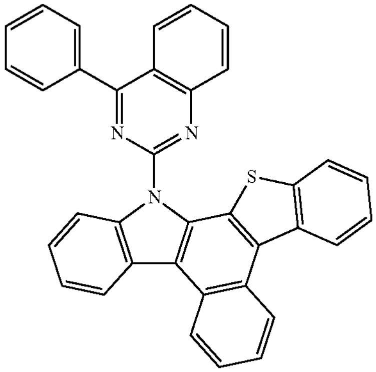

-continued

H123

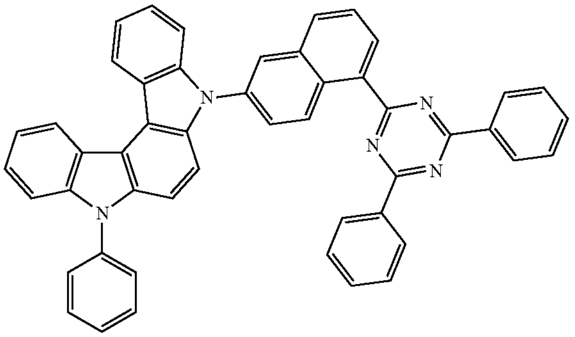

H124

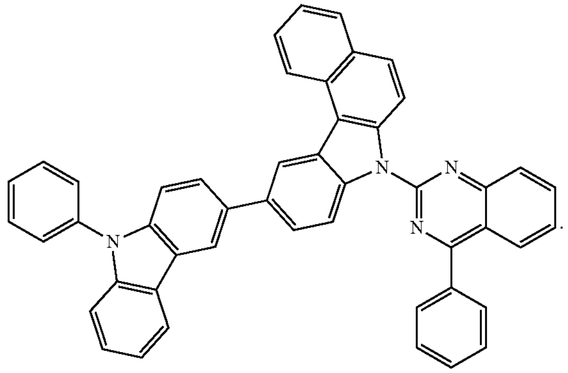

Phosphorescent Dopant

The phosphorescent dopant may include at least one transition metal as a central metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In an embodiment, the phosphorescent dopant may include an organometallic compound represented by Formula 401:

Formula 401

$$M(L_{401})_{xc1}(L_{402})_{xc2}$$

Formula 402

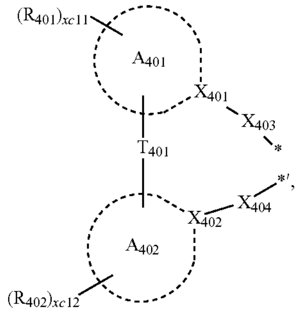

wherein, in Formulae 401 and 402,

M may be a transition metal (for example, iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, wherein, when xc1 is 2 or more, two or more of $L_{401}$(s) may be identical to or different from each other, $L_{402}$ may be an organic ligand, and xc2 may be 0, 1, 2, 3, or 4, wherein, when xc2 is 2 or more, two or more of $L_{402}$(s) may be identical to or different from each other, $X_{401}$ and $X_{402}$ may each independently be nitrogen or carbon, ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—*', *—S—*', *—C(═O)—*', *—N($Q_{411}$)-*', *—C($Q_{411}$)($Q_{412}$)*', *—C($Q_{411}$)═C($Q_{412}$)-*', *—C($Q_{411}$)═*', or *═C($Q_{411}$)═*', $X_{403}$ and $X_{404}$ may each independently be a chemical bond (for example, a covalent bond or a coordination bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ are the same as described in connection with $Q_1$, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(═O)($Q_{401}$), —S(═O)$_2$($Q_{401}$), or —P(═O)($Q_{401}$)($Q_{402}$), $Q_{401}$ to $Q_{403}$ may each independently be the same as described in connection with $Q_1$, xc11 and xc12 may each independently be an integer from 0 to 10, and and *' in Formula 402 each indicate a binding site to M in Formula 401.

In an embodiment, in Formula 402, i) $X_{401}$ may be nitrogen, and $X_{402}$ may be carbon, or ii) each of $X_{401}$ and $X_{402}$ may be nitrogen.

In one or more embodiments, when xc1 in Formula 402 is 2 or more, two ring $A_{401}$(s) in two or more of $L_{401}$(s) may be optionally linked to each other via $T_{402}$, which is a linking group, and/or two ring $A_{402}$(s) may be optionally linked to each other via $T_{403}$, which is a linking group (see Compounds PD1 to PD4 and PD7). $T_{402}$ and $T_{403}$ may each independently be the same as described in connection with $T_{401}$.

$L_{402}$ in Formula 401 may be an organic ligand. In an embodiment, $L_{402}$ may include a halogen group, a diketone group (for example, an acetylacetonate group), a carboxylic acid group (for example, a picolinate group), —C(═O), an isonitrile group, a —CN group, a phosphorus group (for example, a phosphine group, a phosphite group, etc.), or any combination thereof.

The phosphorescent dopant may include, for example, one of Compounds PD1 to PD39 and Dopant-2, or any combination thereof:

PD1

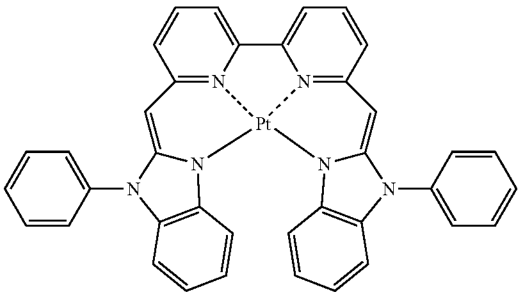

PD2

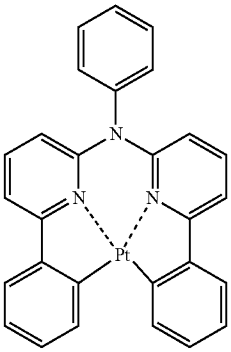

PD3

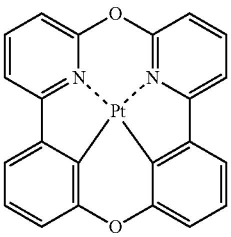

PD4

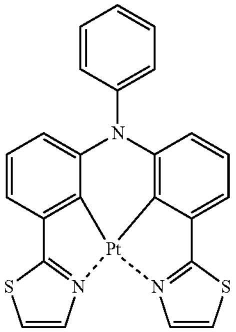

PD5

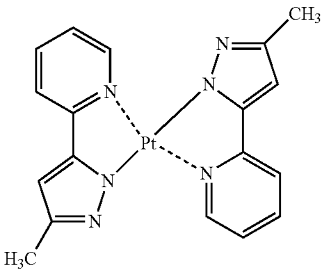

-continued
PD6
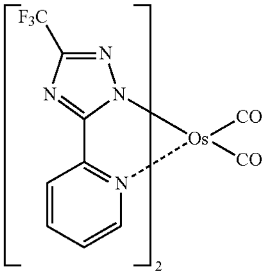
PD7
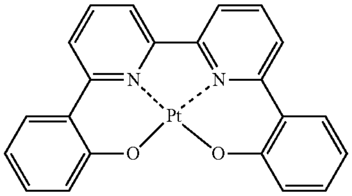
PD8
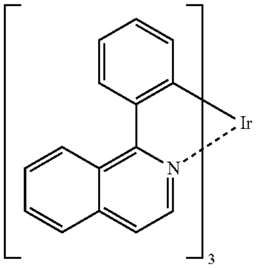
PD9
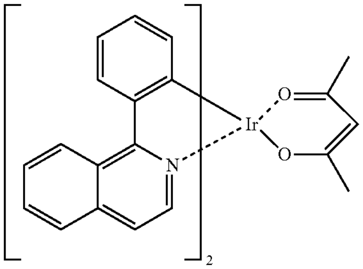
PD10
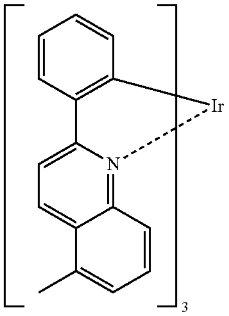
-continued
PD11
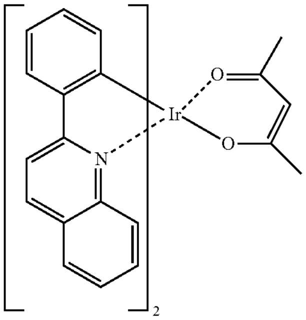
PD12
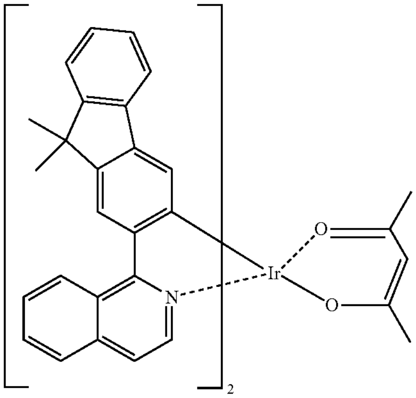
PD13
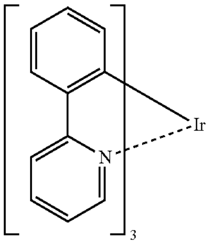
PD14
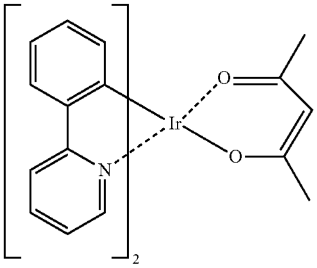
PD15
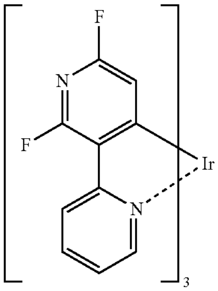

-continued
PD16
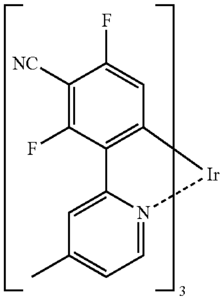
PD17
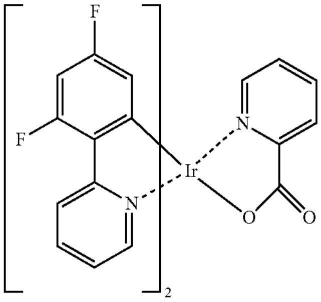
PD18
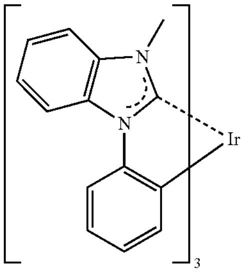
PD19
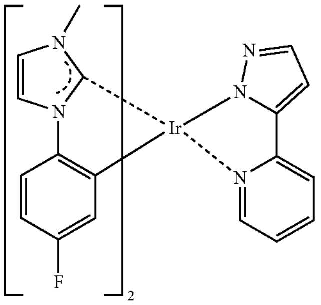
PD20
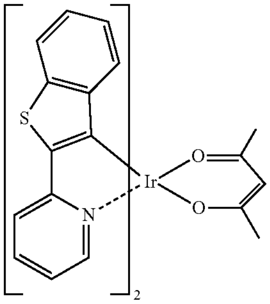
-continued
PD21
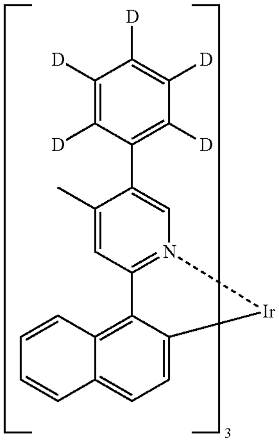
PD22
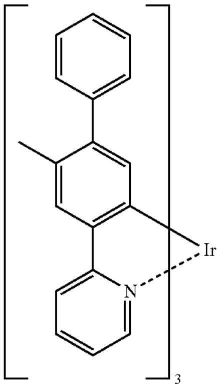
PD23
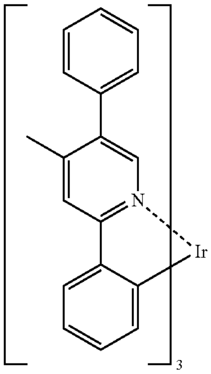
PD24
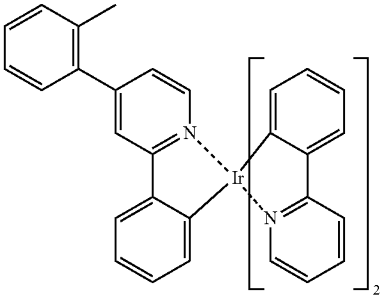

-continued
PD25
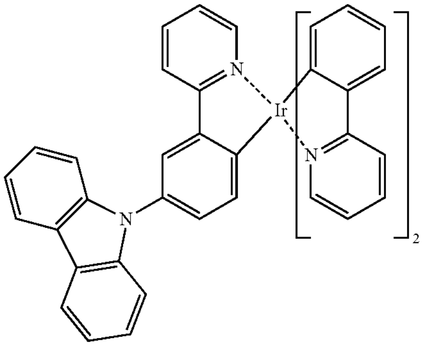
PD26
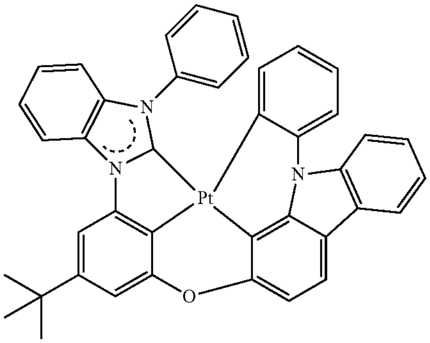
PD27
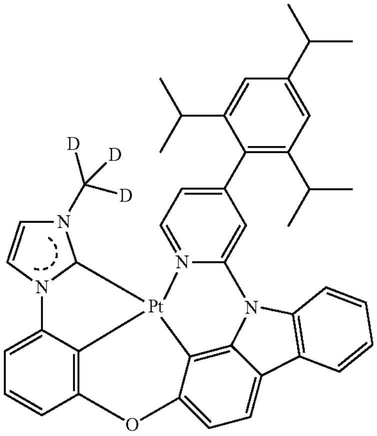
PD28
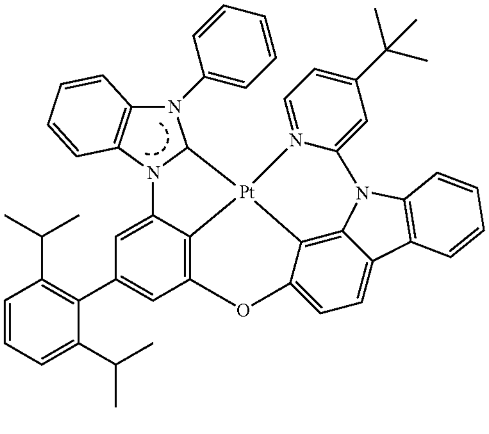
-continued
PD29
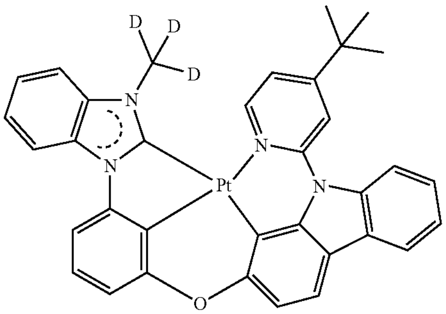
PD30
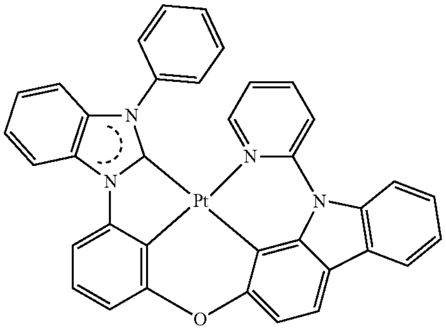
PD31
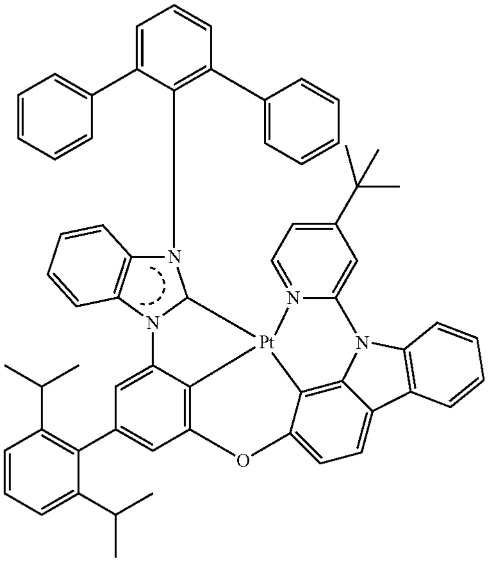

-continued
PD32
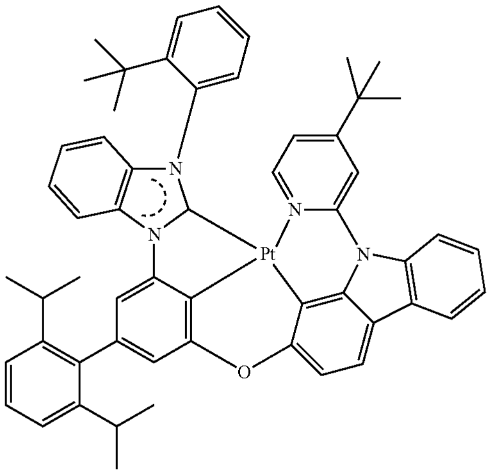
PD33
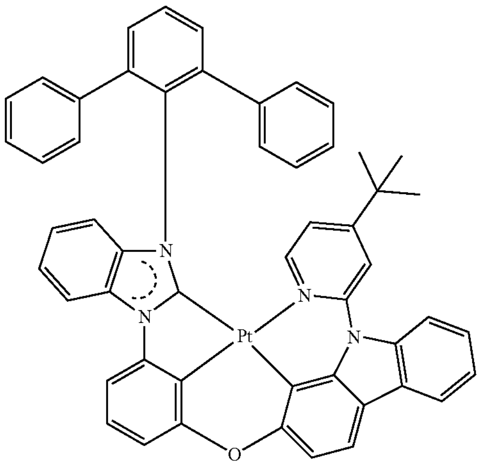
PD34
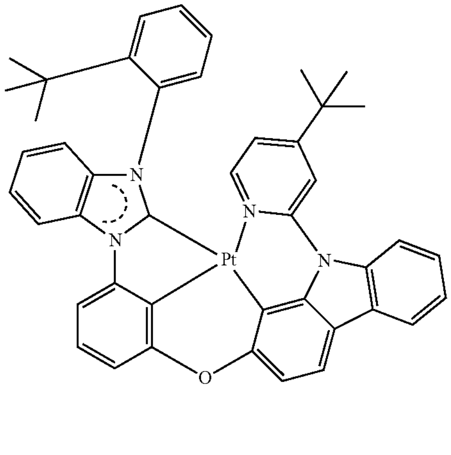
-continued
PD35
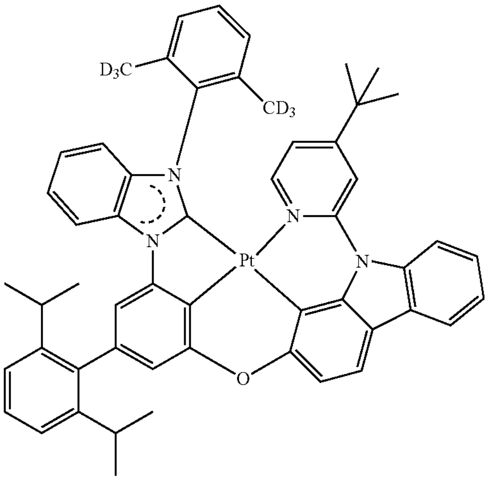
PD36
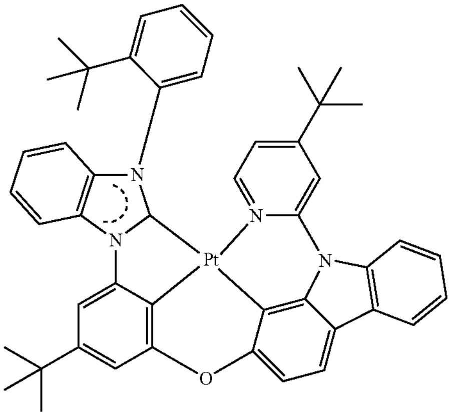
PD37
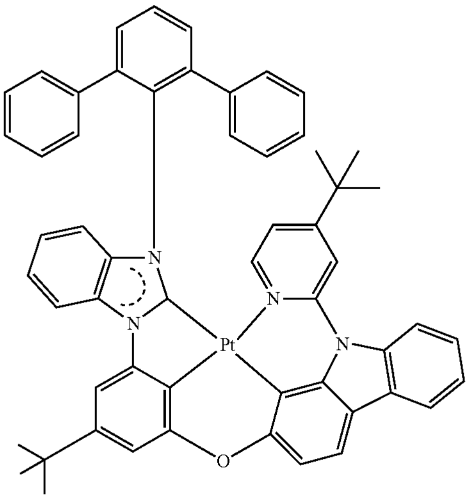

-continued

PD38

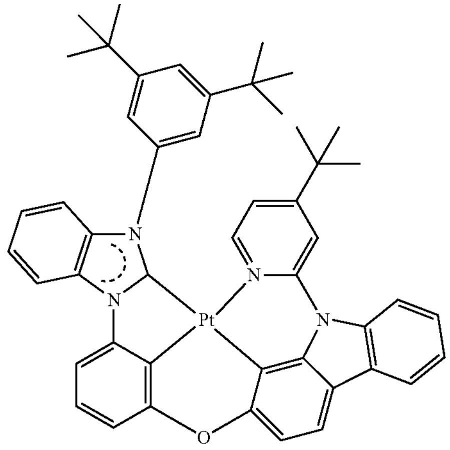

PD39

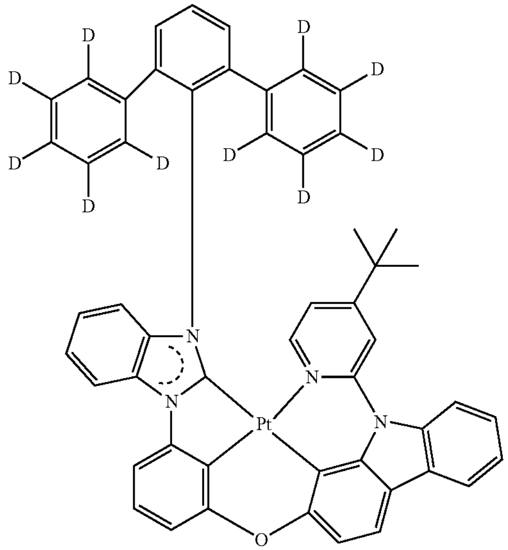

Dopant-2

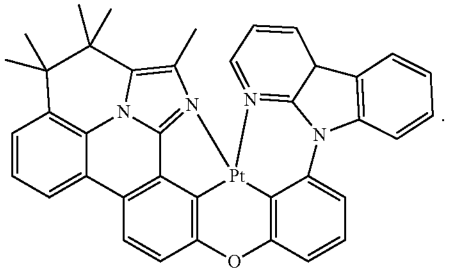

Fluorescent Dopant

The fluorescent dopant may include an amine group-containing compound, a styryl group-containing compound, or any combination thereof.

In an embodiment, the fluorescent dopant may include a compound represented by Formula 501:

Formula 501

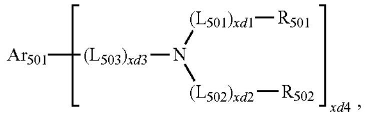

wherein, in Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In an embodiment, $Ar_{501}$ in Formula 501 may be a condensed cyclic group (for example, an anthracene group, a chrysene group, or a pyrene group) in which three or more monocyclic groups are condensed together.

In one or more embodiments, xd4 in Formula 501 may be 2.

In an embodiment, the fluorescent dopant may include: one of Compounds FD1 to FD36; DPVBi; DPAVBi; or any combination thereof:

FD1

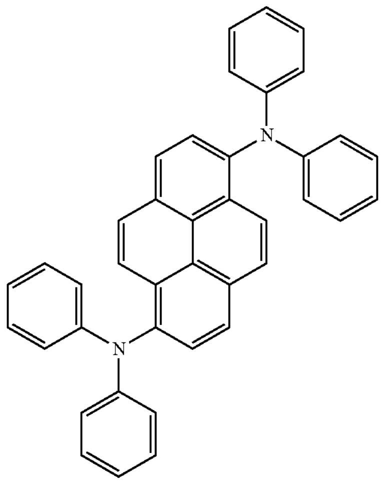

FD2

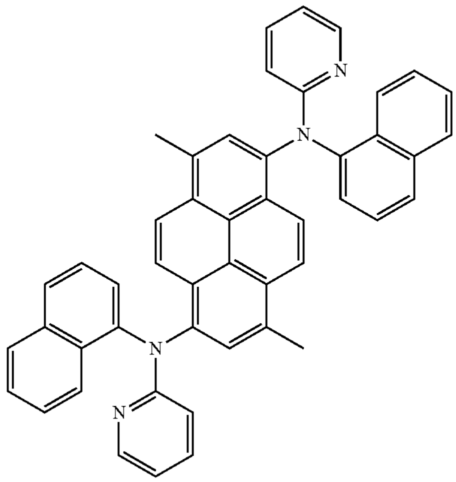

-continued
FD3
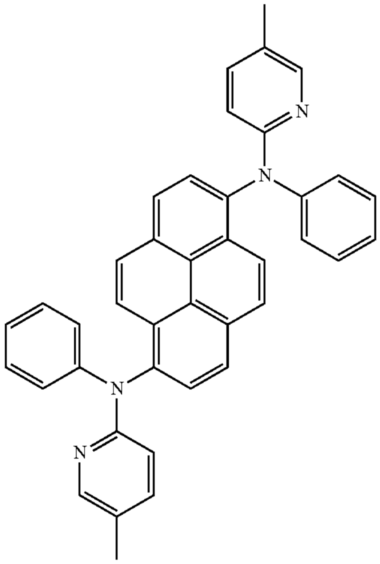
FD4
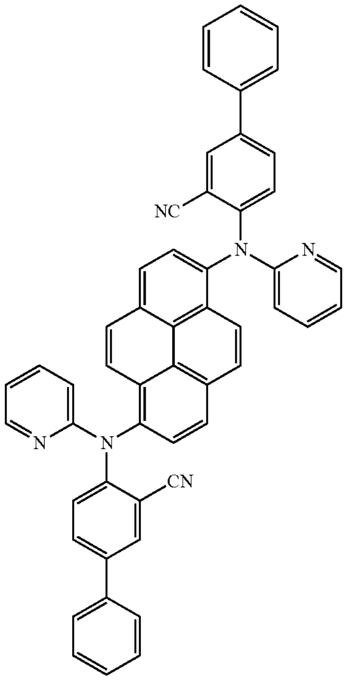
-continued
FD5
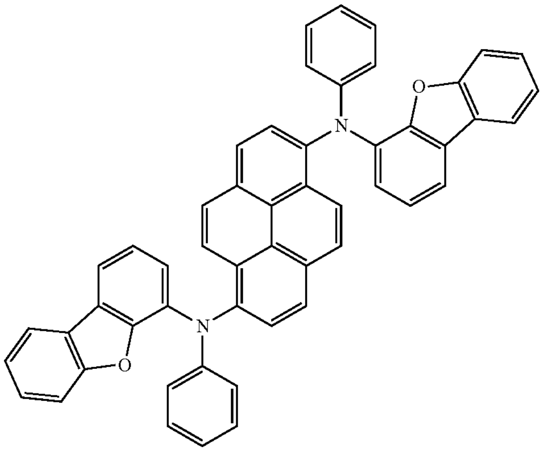
FD6
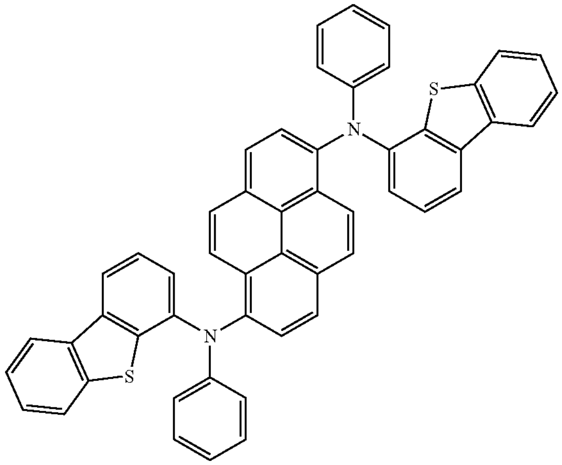
FD7
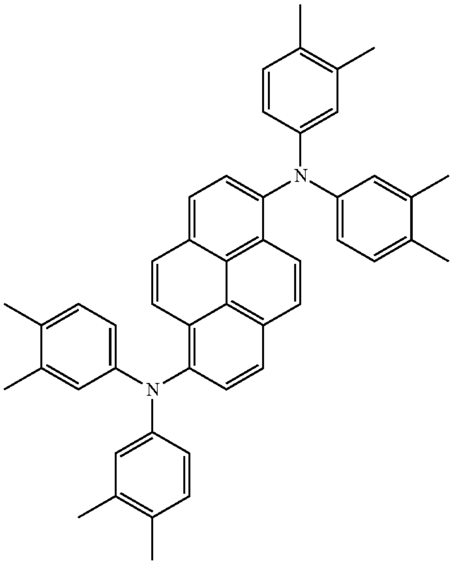

-continued
FD8
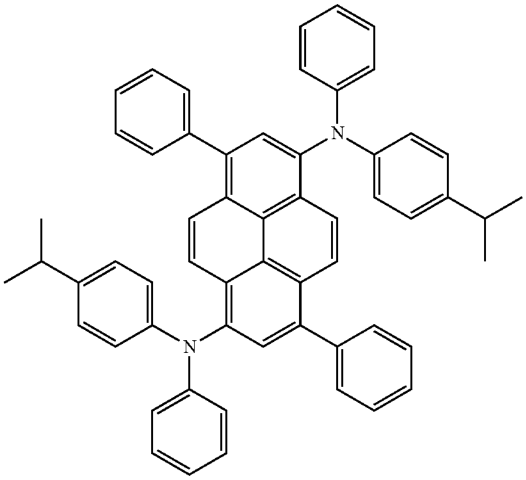
FD9
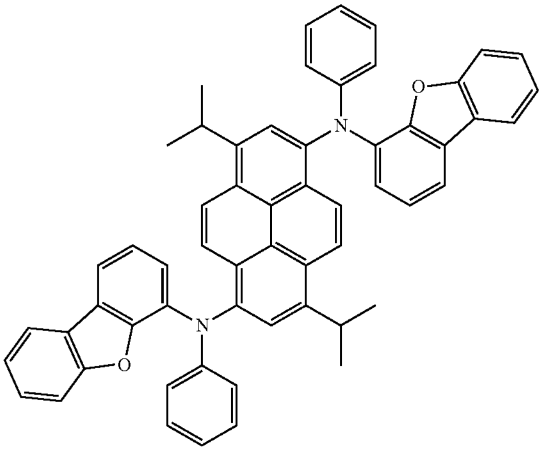
FD10
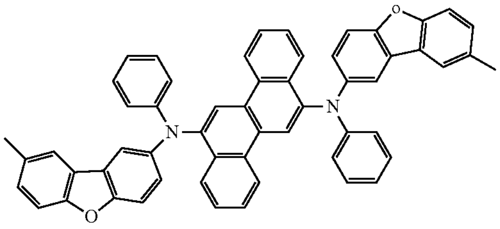
FD11
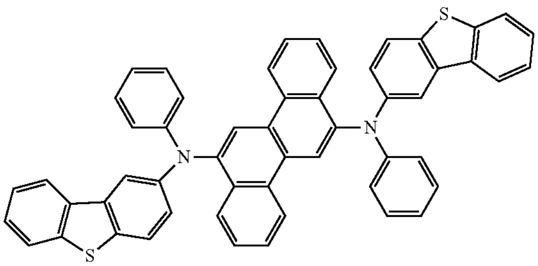
-continued
FD12
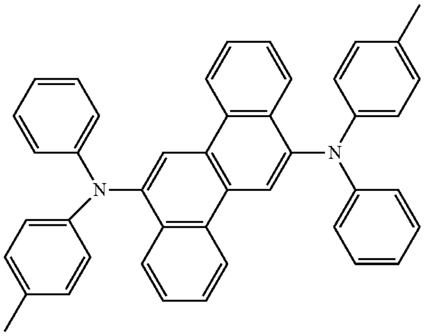
FD13
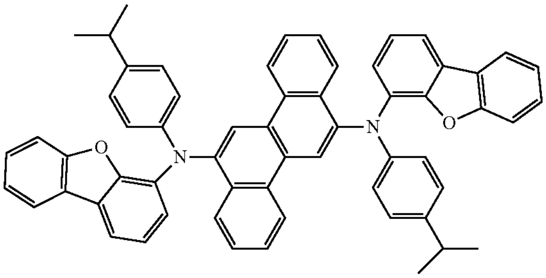
FD14
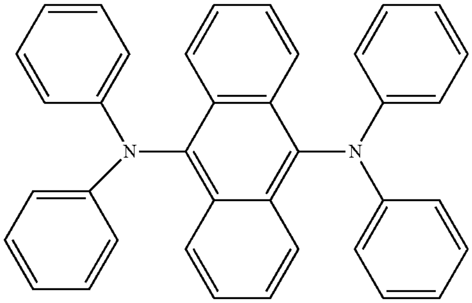
FD15
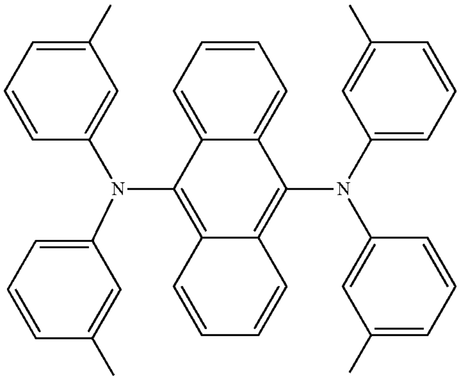

-continued
FD16
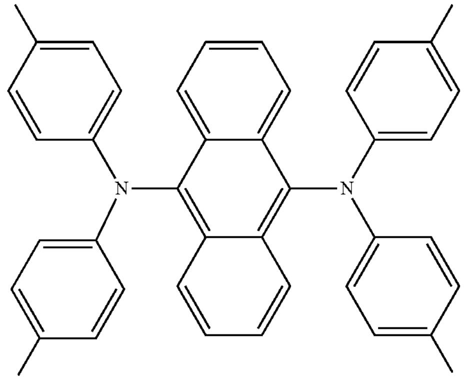
FD17
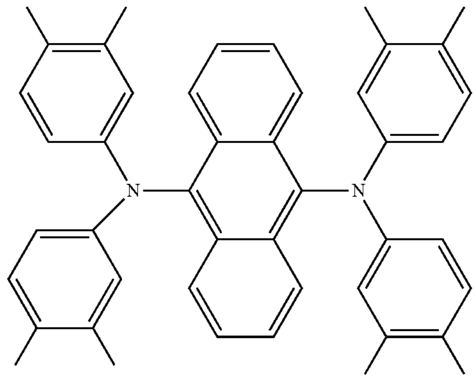
FD18
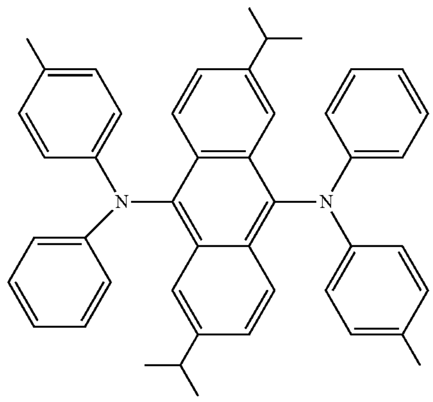
-continued
FD19
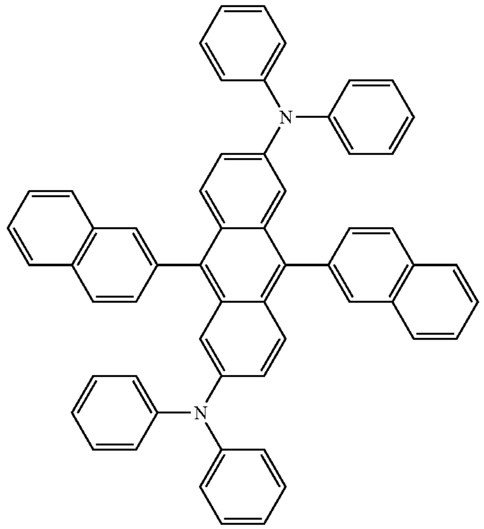
FD20
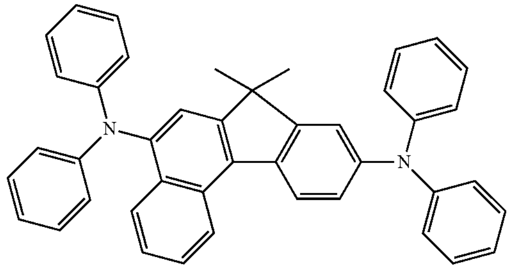
FD21
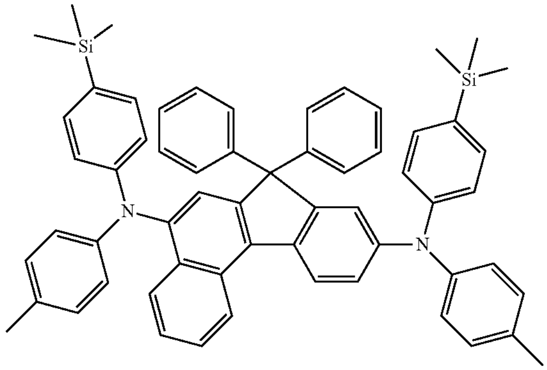
FD22
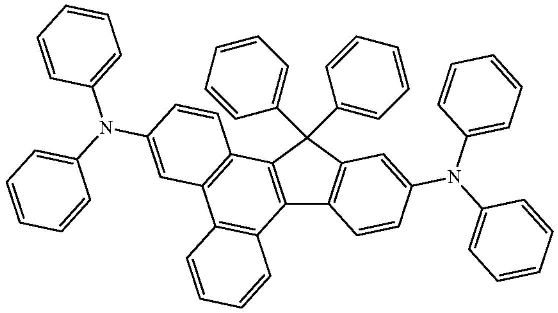

-continued
FD23
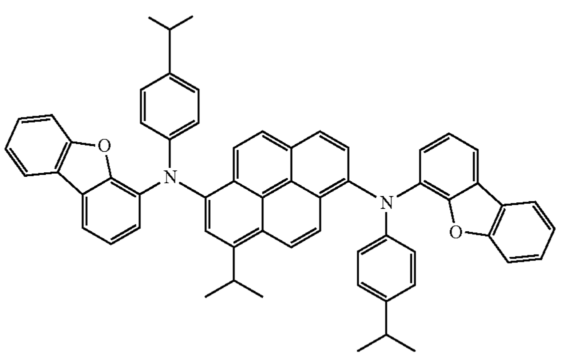
FD24
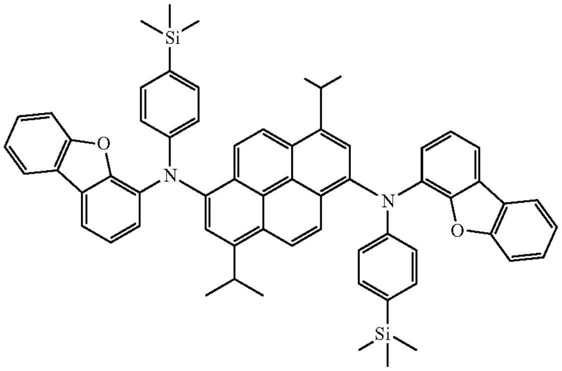
FD25
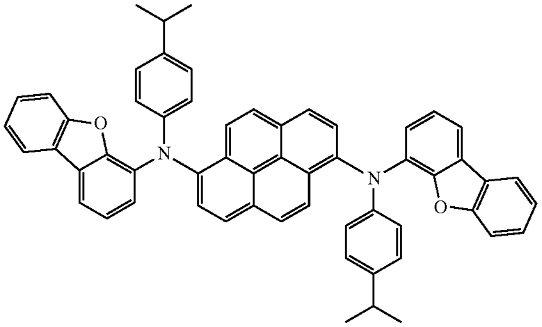
FD26
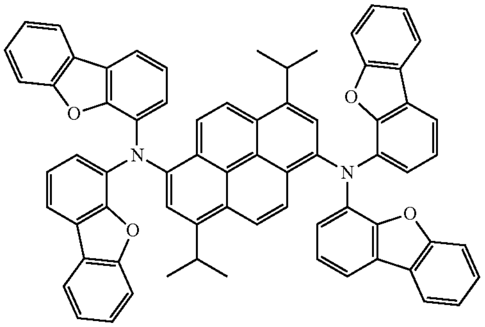
-continued
FD27
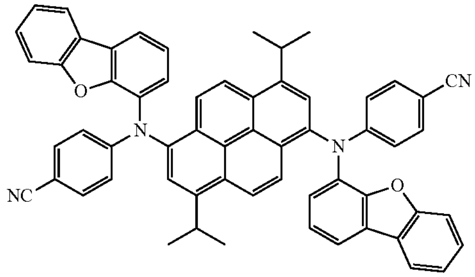
FD28
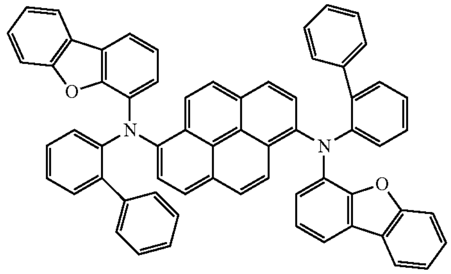
FD29
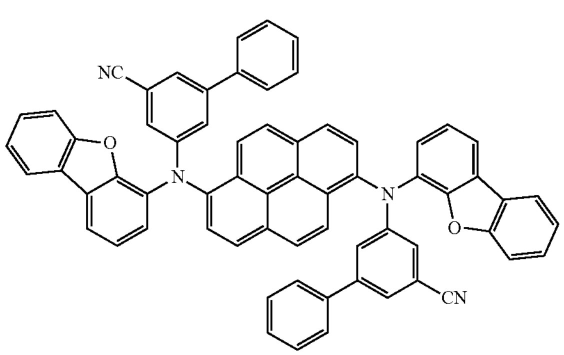
FD30
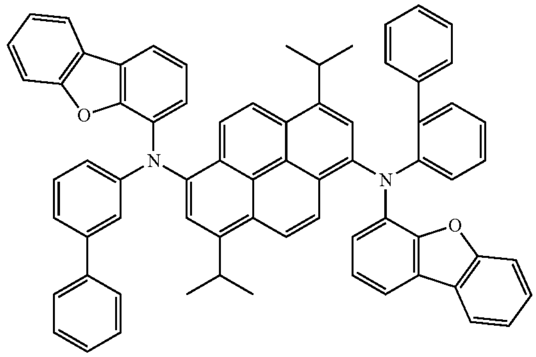
FD31
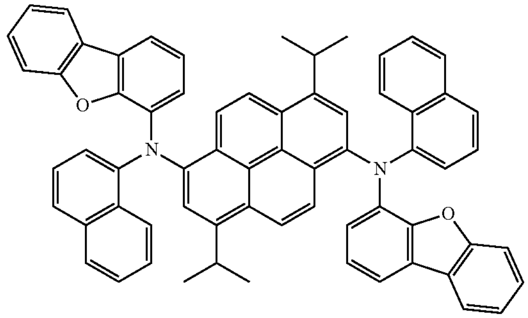

-continued

FD32

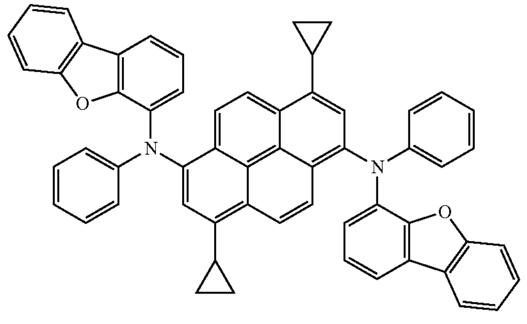

FD33

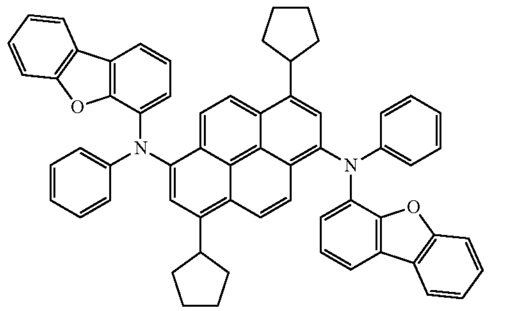

FD34

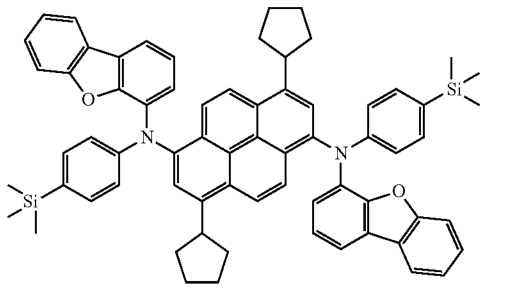

FD35

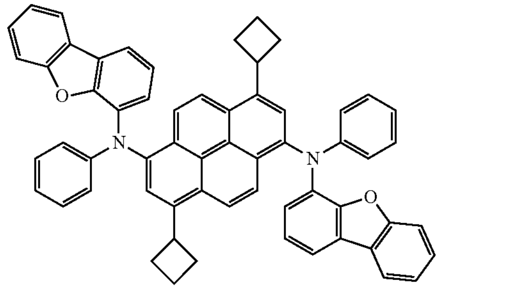

FD36

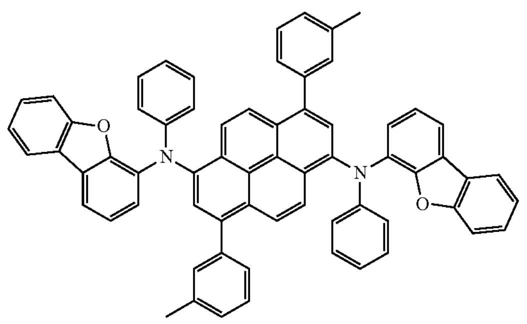

-continued

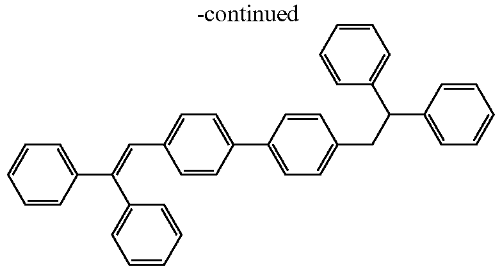

DPVBi

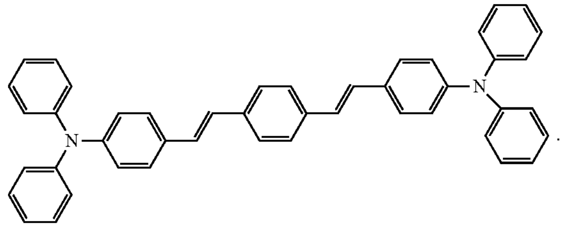

DPAVBi

Delayed Fluorescence Material

The emission layer may include a delayed fluorescence material.

In the present specification, the delayed fluorescence material may be selected from compounds capable of emitting delayed fluorescent light based on a delayed fluorescence emission mechanism.

The delayed fluorescence material included in the emission layer may act as a host or a dopant depending on the type (kind) of other materials included in the emission layer.

In an embodiment, a difference between a triplet energy level in electron volt (eV) of the delayed fluorescence material and a singlet energy level in electron volt (eV) of the delayed fluorescence material may be greater than or equal to 0 eV and less than or equal to 0.5 eV. When the difference between the triplet energy level in electron volt (eV) of the delayed fluorescence material and the singlet energy level in electron volt (eV) of the delayed fluorescence material satisfies the above-described range, up-conversion from the triplet state to the singlet state of the delayed fluorescence materials may effectively occur, and thus, the luminescence efficiency of the light-emitting device 10 may be improved.

In an embodiment, the delayed fluorescence material may include i) a material including at least one electron donor (for example, a π electron-rich $C_3$-$C_{60}$ cyclic group, such as a carbazole group) and at least one electron acceptor (for example, a sulfoxide group, a cyano group, and/or a π electron-deficient nitrogen-containing $C_1$-$C_{60}$ cyclic group), and/or ii) a material including a $C_8$-$C_{60}$ polycyclic group in which two or more cyclic groups are condensed while sharing boron (B).

Examples of the delayed fluorescence material may include at least one of Compounds DF1 to DF9 and Dopant-1:

DF1
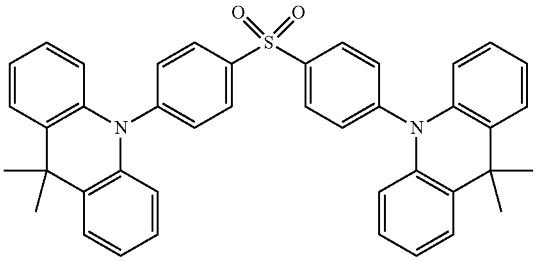
(DMAC-DPS)
DF2
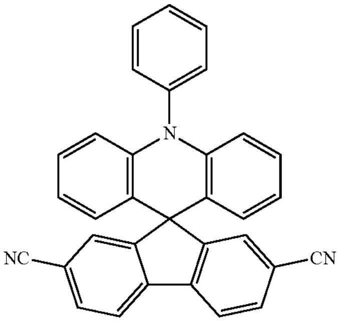
(ACRFLCN)
DF3
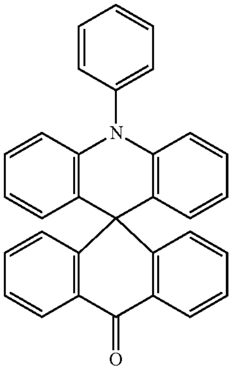
(ACRSA)
DF4
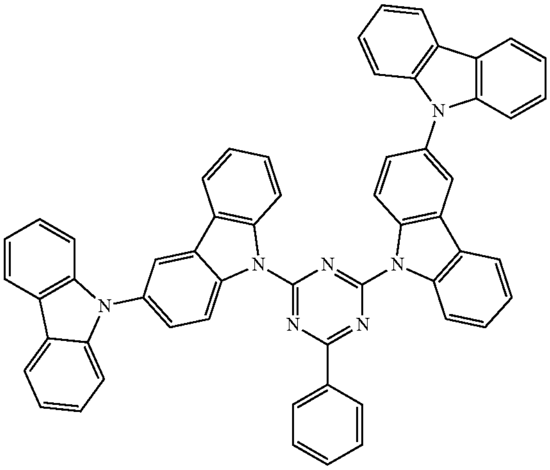
(CC2TA)
-continued
DF5
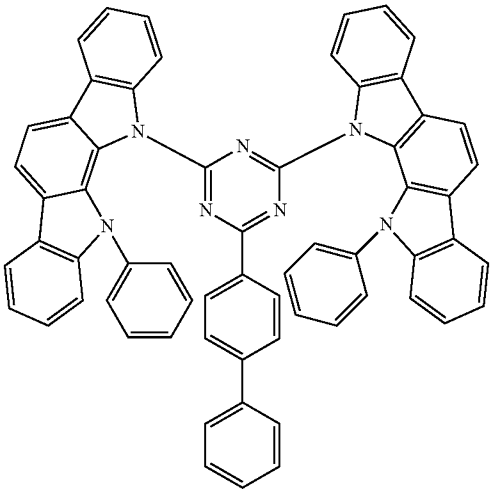
(PIC-TRZ)
DF6
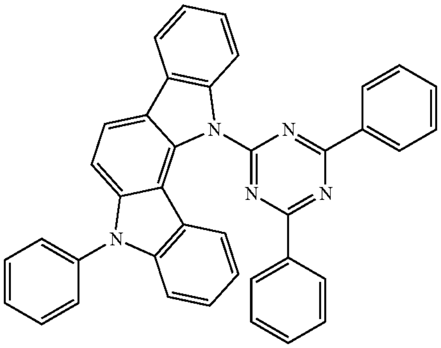
(PIC-TRZ2)
DF7
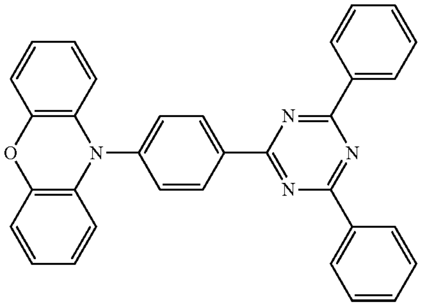
(PXZ-TRZ)
DF8
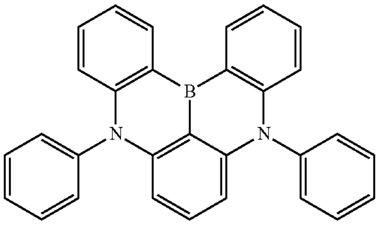
(DABNA-1)

-continued

DF9

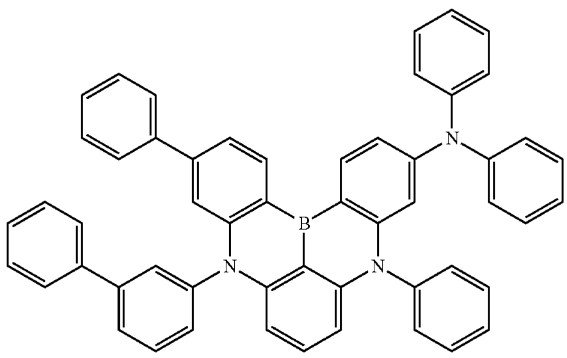

(DABNA-2)

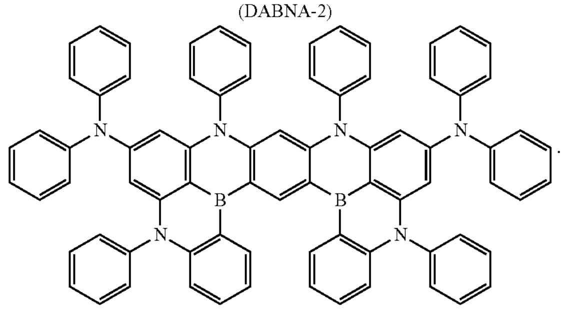

Dopant-1

Quantum Dot

The emission layer may include a quantum dot.

In the present specification, a quantum dot refers to a crystal of a semiconductor compound, and may include any material capable of emitting light of various suitable emission wavelengths according to the size of the crystal.

A diameter of the quantum dot may be, for example, in a range of about 1 nm to about 10 nm.

The quantum dot may be synthesized by a wet chemical process, a metal organic (e.g., organometallic) chemical vapor deposition process, a molecular beam epitaxy process, or any suitable process similar thereto.

According to the wet chemical process, a precursor material is mixed with an organic solvent to grow a quantum dot particle crystal. When the crystal grows, the organic solvent naturally acts as a dispersant coordinated on the surface of the quantum dot crystal and controls the growth of the crystal so that the growth of quantum dot particles can be controlled through a process which is more easily performed than vapor deposition methods, such as metal organic chemical vapor deposition (MOCVD) and/or molecular beam epitaxy (MBE), and which is a low cost process.

The quantum dot may include: a Group II-VI semiconductor compound; a Group III-V semiconductor compound; a Group III-VI semiconductor compound; a Group I-III-VI semiconductor compound; a Group IV-VI semiconductor compound; a Group IV element or compound; or any combination thereof.

Examples of the Group II-VI semiconductor compound may include: a binary compound, such as CdSe, CdTe, ZnS, ZnSe, ZnTe, ZnO, HgS, HgSe, HgTe, MgSe, and/or MgS; a ternary compound, such as CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and/or MgZnS; a quaternary compound, such as CdZnSeS, CdZnSeTe, CdZnSTe, CdHgSeS, CdHgSeTe, CdHgSTe, HgZnSeS, HgZnSeTe, and/or HgZnSTe; or any combination thereof.

Examples of the Group III-V semiconductor compound may include: a binary compound, such as GaN, GaP, GaAs, GaSb, AlN, AlP, AlAs, AlSb, InN, InP, InAs, and/or InSb; a ternary compound, such as GaNP, GaNAs, GaNSb, GaPAs, GaPSb, AlNP, AlNAs, AlNSb, AlPAs, AlPSb, InGaP, InNP, InAlP, InNAs, InNSb, InPAs, and/or InPSb; a quaternary compound, such as GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, and/or InAlPSb; or any combination thereof. Meanwhile, the Group III-V semiconductor compound may further include a Group II element. Examples of the Group III-V semiconductor compound further including the Group II element may include InZnP, InGaZnP, InAlZnP, and/or the like.

Examples of the Group III-VI semiconductor compound may include: a binary compound, such as GaS, GaSe, $Ga_2Se_3$, GaTe, InS, InSe, $In_2S_3$, $In_2Se_3$, and/or InTe; a ternary compound, such as $InGaS_3$ and/or $InGaSe_3$; or any combination thereof.

Examples of the Group I-III-VI semiconductor compound may include: a ternary compound, such as AgInS, $AgInS_2$, CuInS, $CuInS_2$, $CuGaO_2$, $AgGaO_2$, and/or $AgAlO_2$; or any combination thereof.

Examples of the Group IV-VI semiconductor compound may include: a binary compound, such as SnS, SnSe, SnTe, PbS, PbSe, and/or PbTe; a ternary compound, such as SnSeS, SnSeTe, SnSTe, PbSeS, PbSeTe, PbSTe, SnPbS, SnPbSe, and/or SnPbTe; a quaternary compound, such as SnPbSSe, SnPbSeTe, and/or SnPbSTe; or any combination thereof.

The Group IV element or compound may include: a single element compound, such as Si and/or Ge; a binary compound, such as SiC and/or SiGe; or any combination thereof.

Each element included in a multi-element compound such as the binary compound, the ternary compound, and/or the quaternary compound may be present at a uniform concentration or non-uniform concentration in a particle.

In an embodiment, the quantum dot may have a single structure in which the concentration of each element in the quantum dot is uniform, or a core-shell dual structure. In an embodiment, in the dual core-shell structure, the material included in the core and the material included in the shell may be different from each other.

The shell of the quantum dot may act as a protective layer to prevent or reduce chemical degeneration of the core to maintain semiconductor characteristics and/or as a charging layer to impart electrophoretic characteristics to the quantum dot.

The shell may be a single layer or a multi-layer. An interface between the core and the shell may have a concentration gradient in which the concentration of an element existing in the shell decreases toward the center of the core.

Examples of the shell of the quantum dot may be an oxide of metal, metalloid, or non-metal, a semiconductor compound, and any combination thereof.

Examples of the oxide of metal, metalloid, or non-metal may include: a binary compound, such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO; a ternary compound, such as $MgAl_2O_4$, $CoFe_2O_4$, $NiFe_2O_4$, and/or $CoMn_2O_4$; or any combination thereof. Examples of the semiconductor compound may include, as described herein, Group II-VI semiconductor compounds; Group III-V semiconductor compounds; Group III-VI semiconductor compounds; Group I-III-VI semiconductor compounds; Group IV-VI semiconductor compounds; or any combination thereof. In an embodiment, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, or any combination thereof.

A full width at half maximum (FWHM) of an emission wavelength spectrum of the quantum dot may be about 45 nm or less, for example, about 40 nm or less, for example, about 30 nm or less, and within these ranges, color purity or color gamut may be increased. In addition, because light emitted through the quantum dot is emitted in all directions, a wide viewing angle may be improved.

In addition, the quantum dot may be a spherical particle, a pyramidal particle, a multi-arm particle, a cubic nanoparticle, a nanotube particle, a nanowire particle, a nanofiber particle, or a nanoplate particle.

Because the energy band gap may be adjusted by controlling the size of the quantum dot, light having various suitable wavelength bands may be obtained from the quantum dot emission layer. Accordingly, by utilizing quantum dots of different sizes, a light-emitting device that emits light of various suitable wavelengths may be implemented. In one or more embodiments, the size of the quantum dot may be selected to emit red, green and/or blue light. In addition, the size of the quantum dot may be configured to emit white light by combining light of various suitable colors.

Electron Transport Region in Interlayer 130

The electron transport region may have i) a single-layered structure consisting of a single layer consisting of a single material, ii) a single-layered structure consisting of a single layer including a plurality of different materials, or iii) a multi-layered structure having a plurality of layers including a plurality of different materials.

The electron transport region may include a buffer layer, a hole blocking layer, an electron control layer, an electron transport layer, an electron injection layer, or any combination thereof.

In an embodiment, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein, for each structure, constituting layers are sequentially stacked from an emission layer in the respective stated order.

The electron transport region (for example, the buffer layer, the hole blocking layer, the electron control layer, or the electron transport layer in the electron transport region) may include a metal-free compound including at least one π electron-deficient nitrogen-containing $C_1$-$C_{60}$ cyclic group.

In an embodiment, the electron transport region may include a compound represented by Formula 601:

$$[Ar_{601}]_{xe11}\text{-}[(L_{601})_{xe1}\text{-}R_{601}]_{xe21} \quad \text{Formula 601}$$

wherein, in Formula 601, $Ar_{601}$ and $L_{601}$ may each independently be a $C_3$-$C_{60}$ carbocyclic group unsubstituted or substituted with at least one $R_{10a}$ or a $C_1$-$C_6$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{601}$)($Q_{602}$)($Q_{603}$), —C(=O)($Q_{601}$), —S(=O)$_2$($Q_{601}$), or —P(=O)($Q_{601}$)($Q_{602}$), $Q_{601}$ to $Q_{603}$ may each independently be the same as described in connection with $Q_1$, xe21 may be 1, 2, 3, 4, or 5, and at least one of $Ar_{601}$, $L_{601}$, or $R_{601}$ may each independently be a π electron-deficient nitrogen-containing $C_1$-$C_{60}$ cyclic group unsubstituted or substituted with at least one $R_{10a}$.

In an embodiment, when xe11 in Formula 601 is 2 or more, two or more of $Ar_{601}$(s) may be linked to each other via a single bond.

In one or more embodiments, $Ar_{601}$ in Formula 601 may be a substituted or unsubstituted anthracene group.

In one or more embodiments, the electron transport region may include a compound represented by Formula 601-1:

Formula 601-1

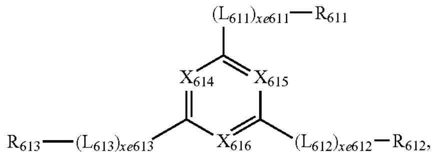

wherein, in Formula 601-1, $X_{614}$ may be N or C($R_{614}$), $X_{615}$ may be N or C($R_{615}$), $X_{616}$ may be N or C($R_{616}$), and at least one of $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

In an embodiment, in Formulae 601 and 601-1, xe1 and xe611 to xe613 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), $Alq_3$, BAlq, TAZ, NTAZ, TSPO1, TPBI, or any combination thereof:

-continued
ET1
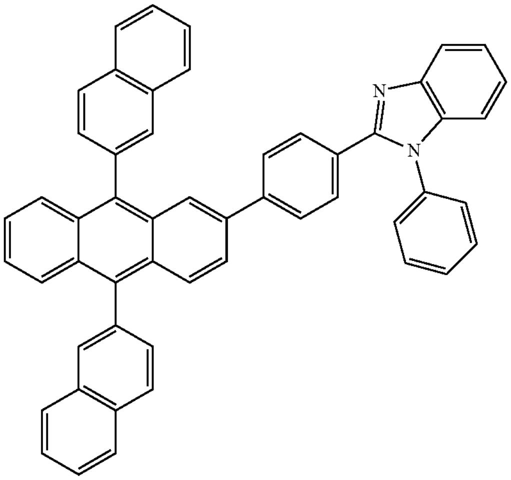
ET2
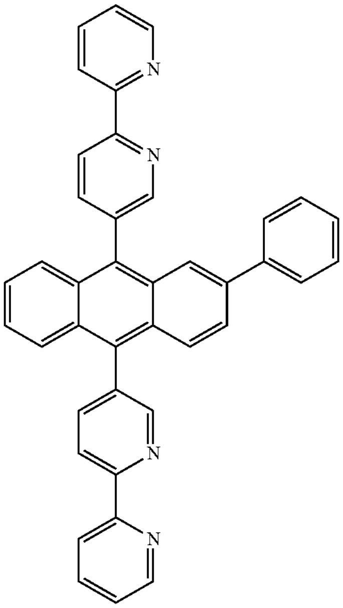
ET3
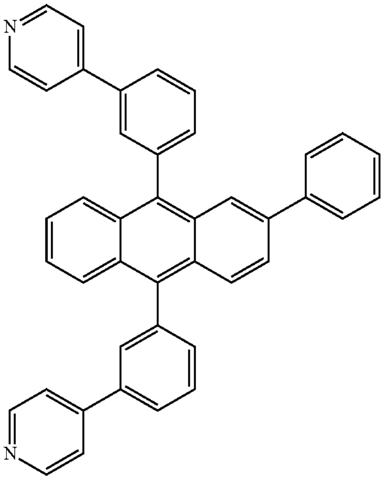
ET4
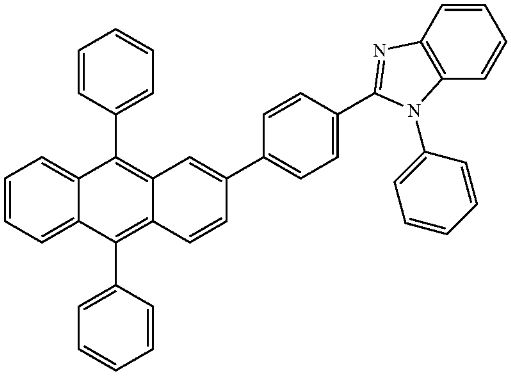
ET5
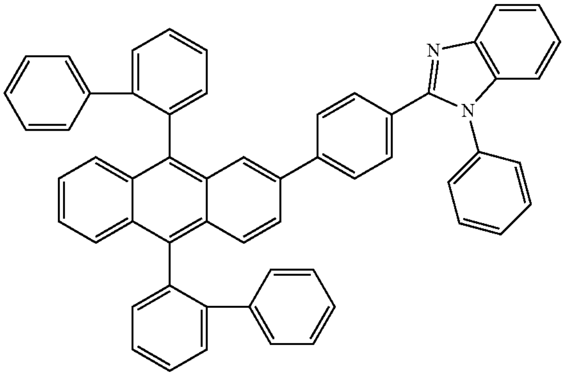
ET6
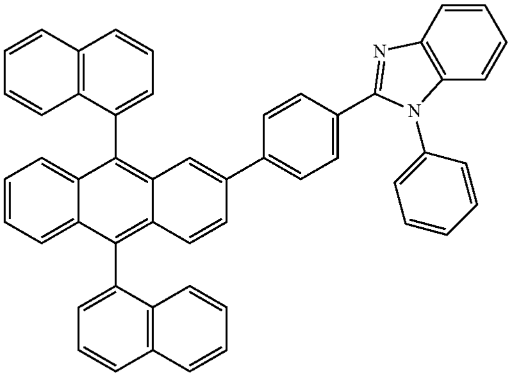
ET7
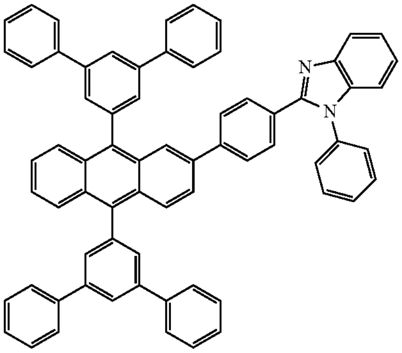

-continued
ET8
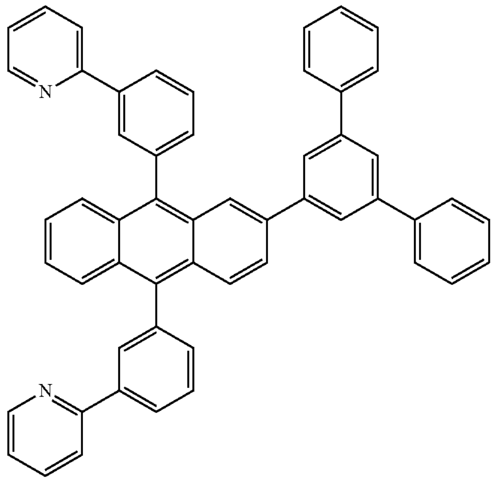
ET9
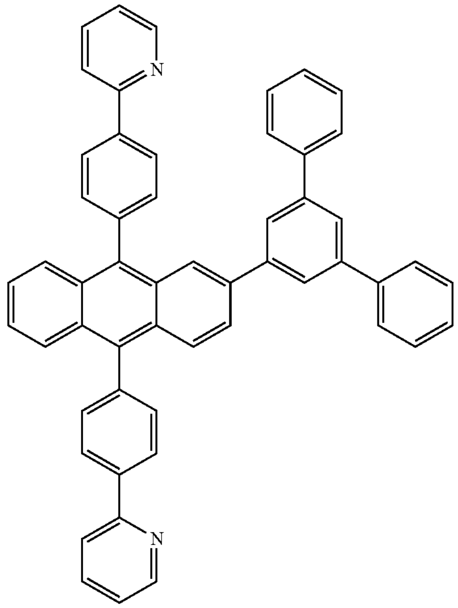
-continued
ET10
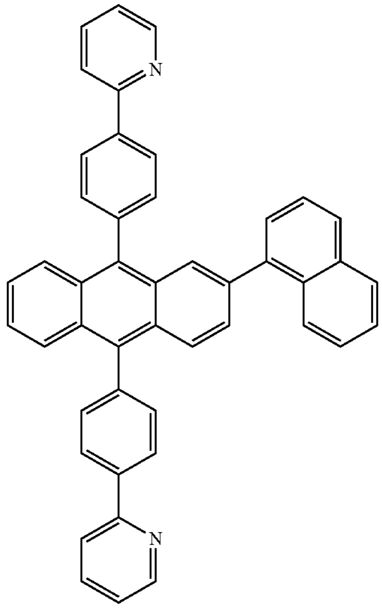
ET11
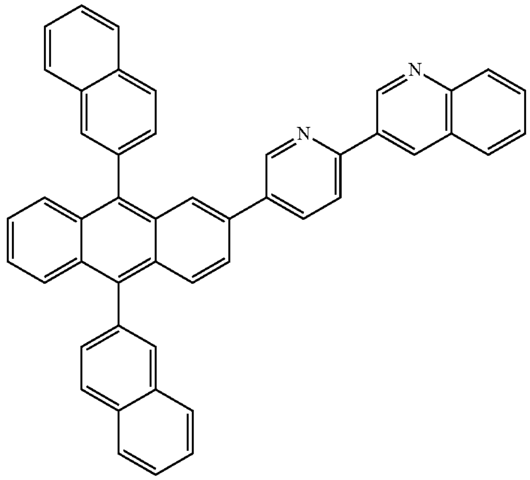
ET12
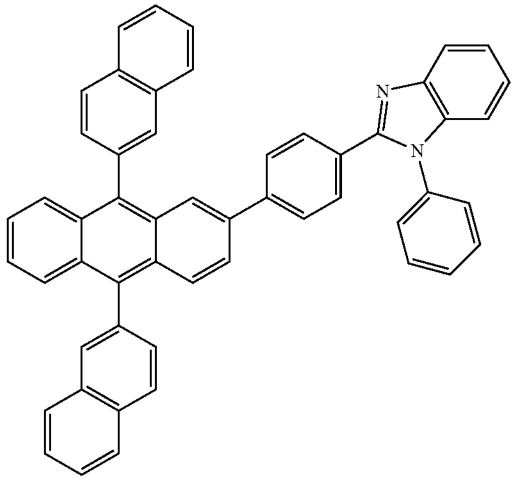

-continued
ET13
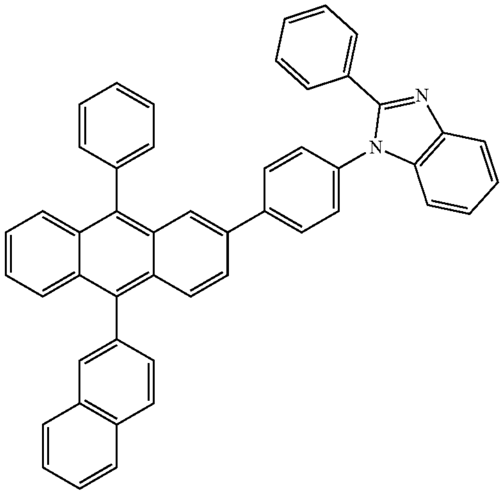
ET14
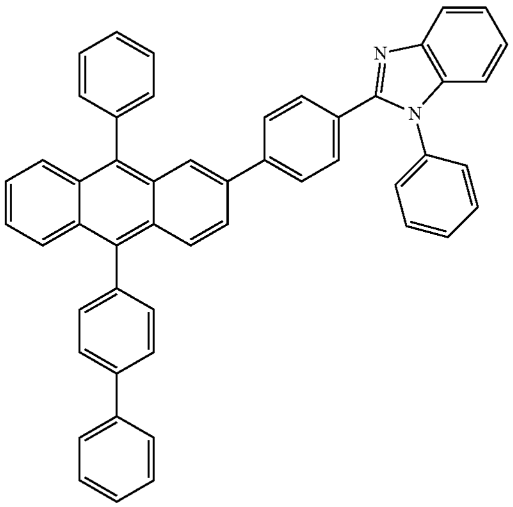
ET15
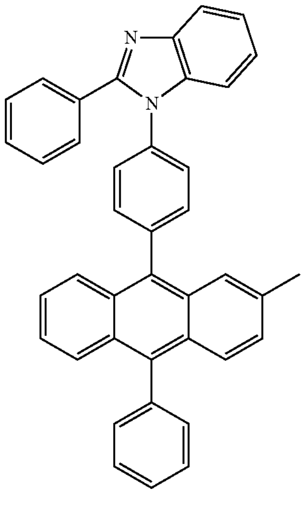
-continued
ET16
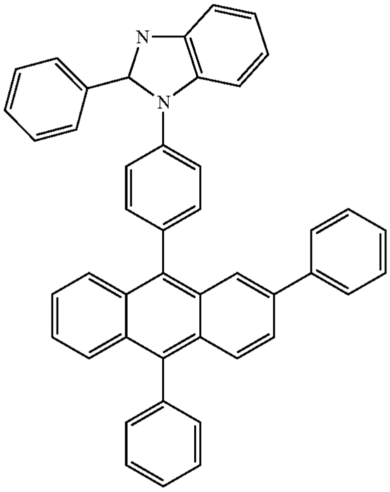
ET17
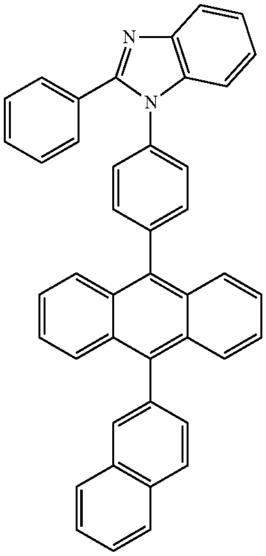
ET18
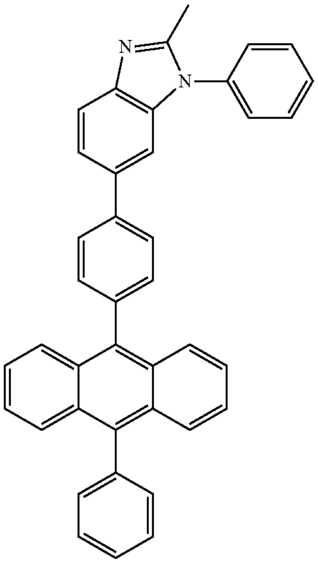

-continued
ET19
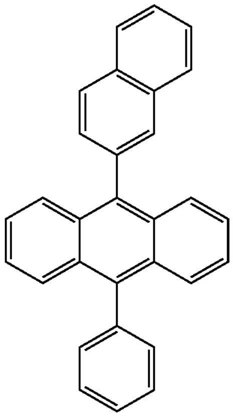
ET20
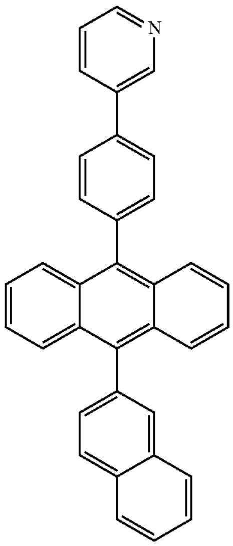
ET21
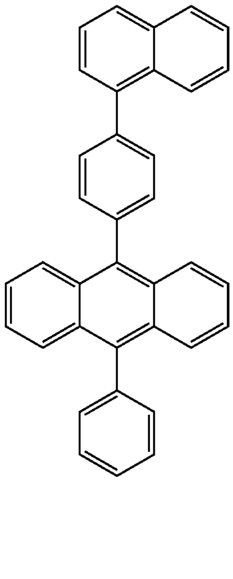
-continued
ET22
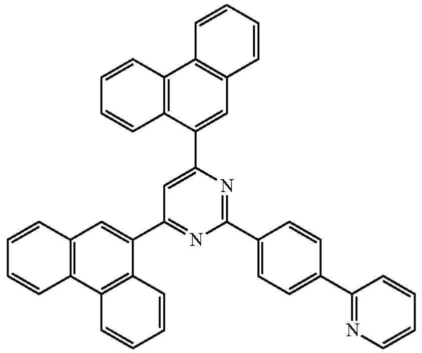
ET23
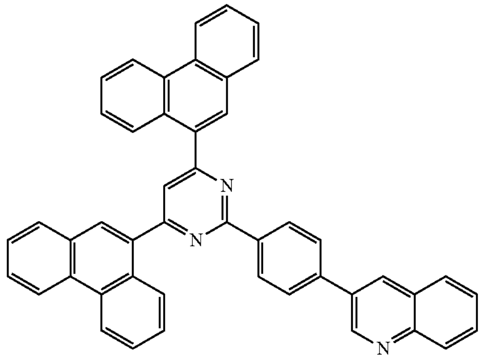
ET24
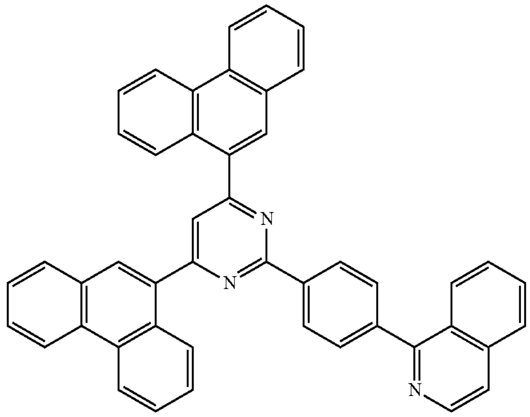
ET25
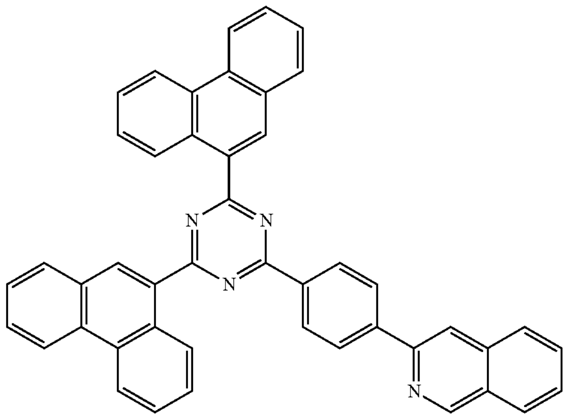

-continued
ET26
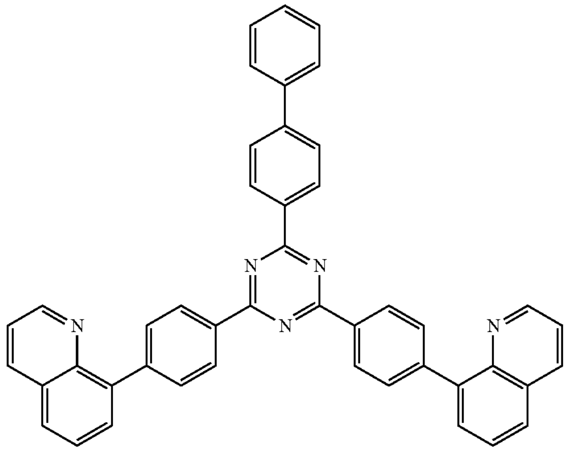
ET27
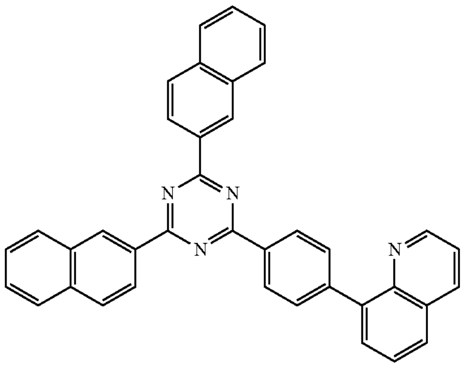
ET28
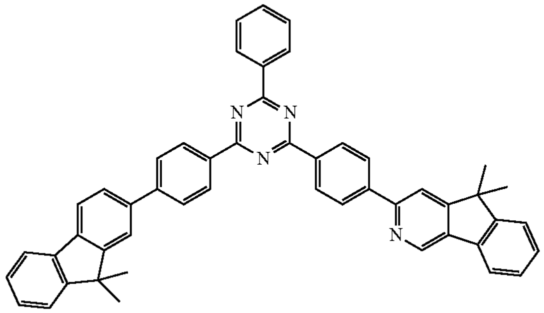
-continued
ET29
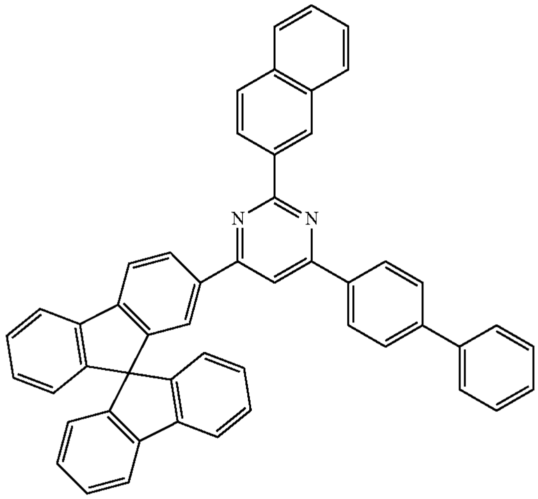
ET30
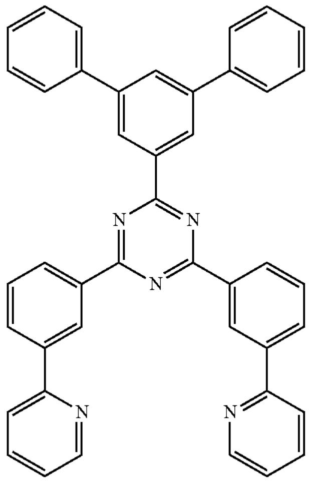
ET31
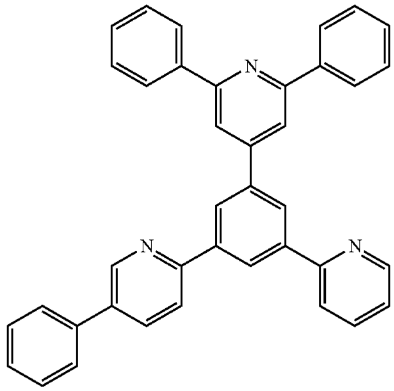

-continued
ET32
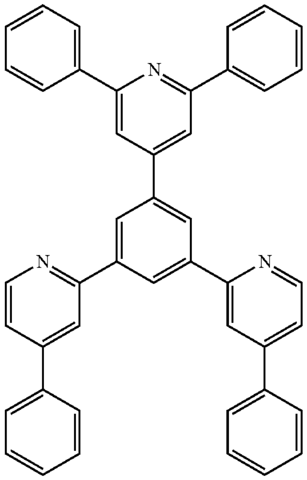
ET33
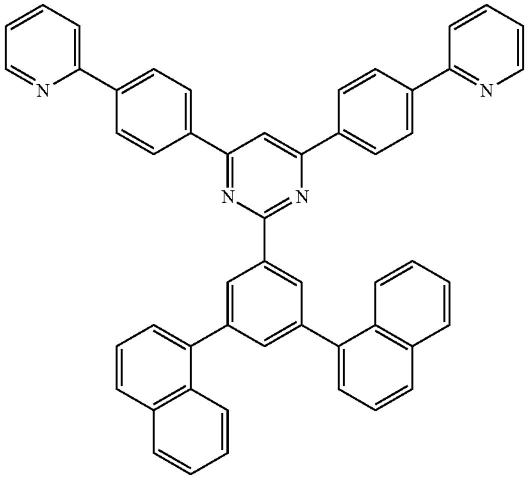
ET34
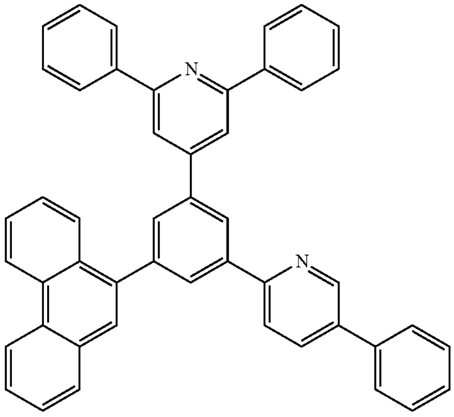
-continued
ET35
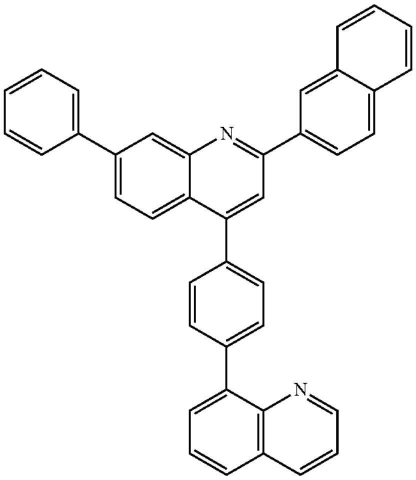
ET36
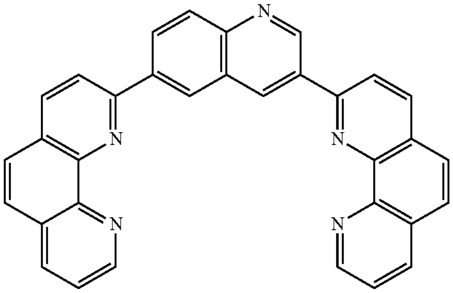
ET37
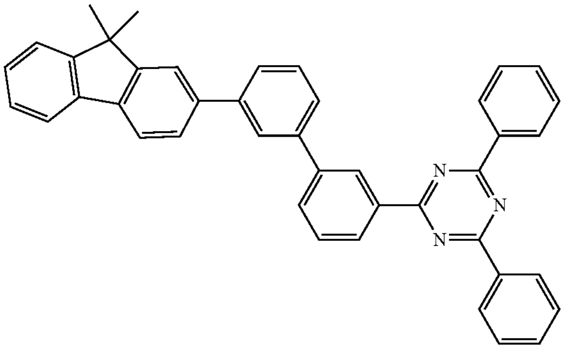
ET38
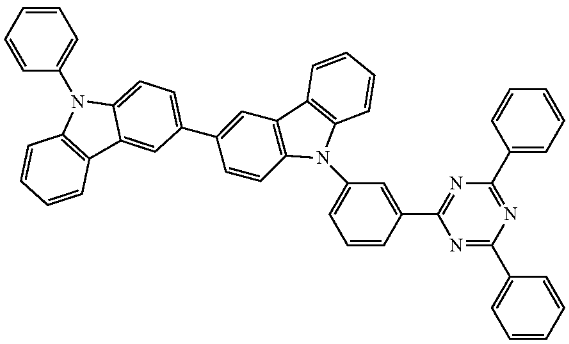

-continued
ET39
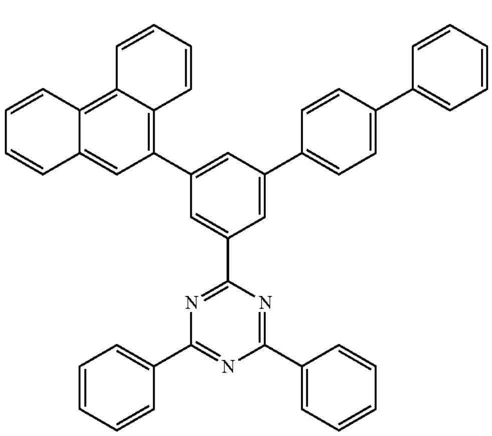
ET40
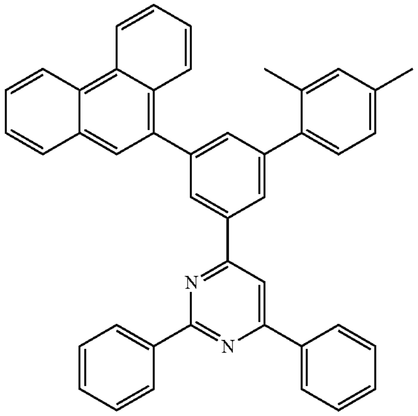
ET41
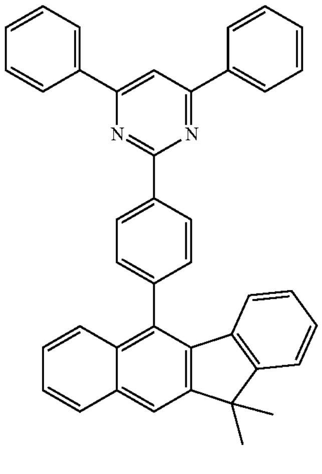
-continued
ET42
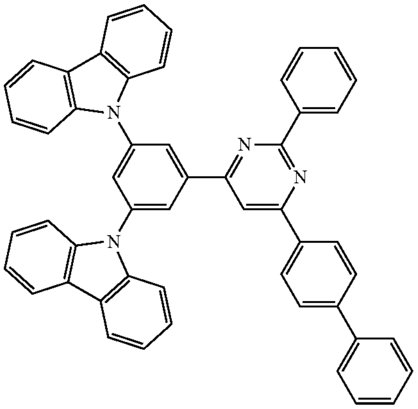
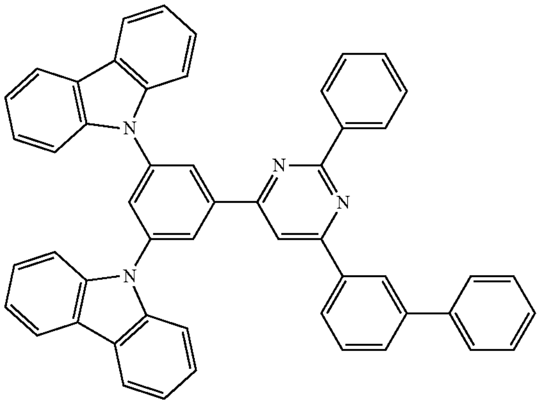
ET44
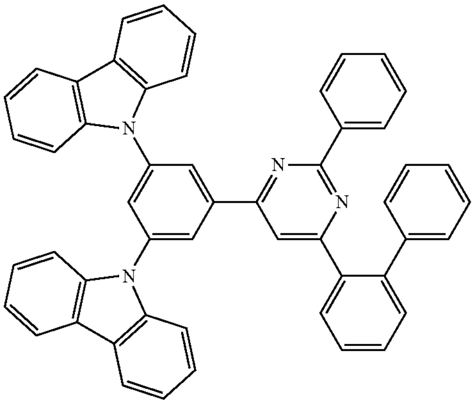
ET45
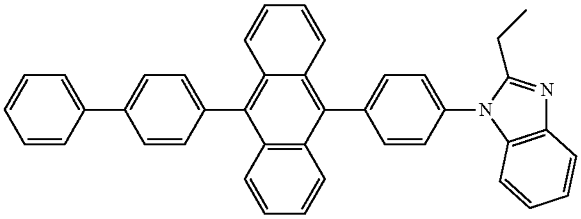

-continued

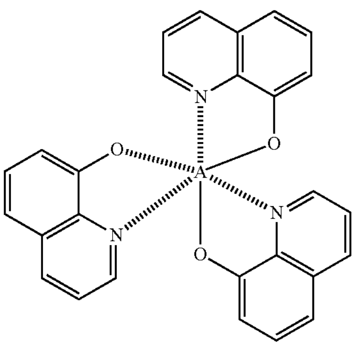

Alq3

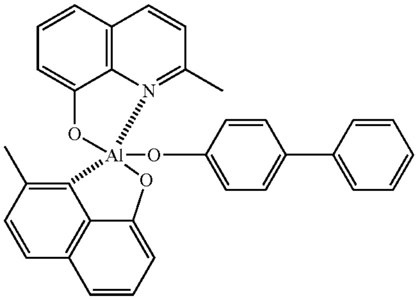

Balq

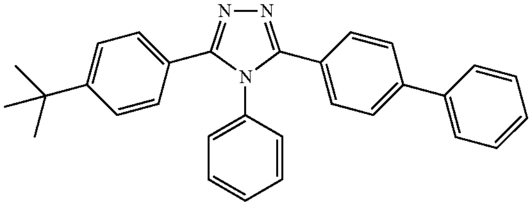

TAZ

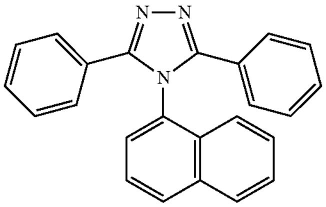

NTAZ

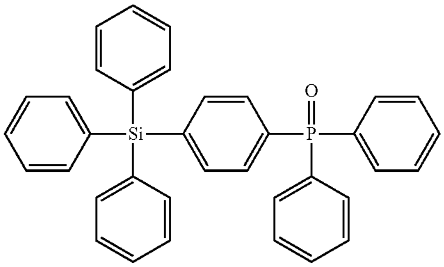

TSPO1

-continued

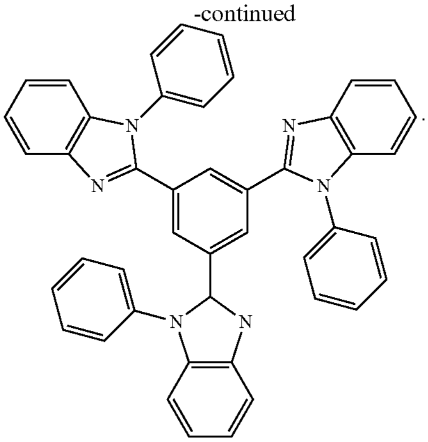

TPBI

A thickness of the electron transport region may be from about 100 Å to about 5,000 Å, for example, about 160 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be from about 20 Å to about 1,000 Å, for example, about 30 Å to about 300 Å, and a thickness of the electron transport layer may be from about 100 Å to about 1,000 Å, for example, about 150 Å to about 500 Å. When the thicknesses of the buffer layer, the hole blocking layer, the electron control layer, and/or the electron transport layer are within the ranges described above, satisfactory electron transporting characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a Li ion, a Na ion, a K ion, a Rb ion, or a Cs ion, and a metal ion of the alkaline earth metal complex may be a Be ion, a Mg ion, a Ca ion, a Sr ion, or a Ba ion. Each ligand coordinated with the metal ion of the alkali metal complex and the alkaline earth metal complex may independently be hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

In an embodiment, the metal-containing material may include a Li complex. The Li complex may include, for example, Compound ET-D1 (LiQ) or ET-D2:

ET-D1

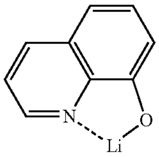

-continued

ET-D2

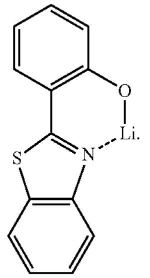

The electron transport region may include an electron injection layer that facilitates injection of electrons from the second electrode 150. The electron injection layer may directly contact the second electrode 150.

The electron injection layer may have i) a single-layered structure consisting of a single layer consisting of a single material, ii) a single-layered structure consisting of a single layer including a plurality of different materials, or iii) a multi-layered structure having a plurality of layers including a plurality of different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs, or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may include oxides, halides (for example, fluorides, chlorides, bromides, and/or iodides), and/or tellurides of the alkali metal, the alkaline earth metal, and the rare earth metal, or any combination thereof.

The alkali metal-containing compound may include alkali metal oxides (such as $Li_2O$, $Cs_2O$, and/or $K_2O$), alkali metal halides (such as LiF, NaF, CsF, KF, LiI, NaI, CsI, and/or KI), or any combination thereof. The alkaline earth metal-containing compound may include an alkaline earth metal compound, such as BaO, SrO, CaO, $Ba_xSr_{1-x}O$ (x is a real number satisfying the condition of $0<x<1$), $Ba_xCa_{1-x}O$ (x is a real number satisfying the condition of $0<x<1$), and/or the like. The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In one or more embodiments, the rare earth metal-containing compound may include lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, and $Lu_2Te_3$.

The alkali metal complex, the alkaline earth-metal complex, and the rare earth metal complex may include i) one of ions of the alkali metal, the alkaline earth metal, and the rare earth metal and ii), as a ligand bonded to the metal ion, for example, hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenyl benzimidazole, hydroxyphenylbenzothiazole, bipyridine, phenanthroline, cyclopentadiene, or any combination thereof.

The electron injection layer may include (e.g., consist of) an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In one or more embodiments, the electron injection layer may further include an organic material (for example, a compound represented by Formula 601).

In an embodiment, the electron injection layer may include (e.g., consist of) i) an alkali metal-containing compound (for example, an alkali metal halide), or ii) a) an alkali metal-containing compound (for example, an alkali metal halide); and b) an alkali metal, an alkaline earth metal, a rare earth metal, or any combination thereof. In an embodiment, the electron injection layer may be a KI:Yb co-deposited layer, an RbI:Yb co-deposited layer, and/or the like.

When the electron injection layer further includes an organic material, the alkali metal, the alkaline earth metal, the rare earth metal, the alkali metal-containing compound, the alkaline earth metal-containing compound, the rare earth metal-containing compound, the alkali metal complex, the alkaline earth-metal complex, the rare earth metal complex, or any combination thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the ranges described above, satisfactory electron injection characteristics may be obtained without a substantial increase in driving voltage.

Second Electrode 150

The second electrode 150 may be located on the interlayer 130 as described above. The second electrode 150 may be a cathode, which is an electron injection electrode, and as the material for forming the second electrode 150, a metal, an alloy, an electrically conductive compound, or any combination thereof, each having a low work function, may be utilized.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure or a multi-layered structure including a plurality of layers.

Capping Layer

A first capping layer may be located outside the first electrode 110 (e.g., on the side opposite to the side facing the second electrode 150), and/or a second capping layer may be located outside the second electrode 150 (e.g., on the side opposite to the side facing the first electrode 110). In some embodiments, the light-emitting device 10 may have a structure in which the first capping layer, the first electrode 110, the interlayer 130, and the second electrode 150 are sequentially stacked in the stated order, a structure in which the first electrode 110, the interlayer 130, the second electrode 150, and the second capping layer are sequentially stacked in the stated order, or a structure in which the first capping layer, the first electrode 110, the interlayer 130, the second electrode 150, and the second capping layer are sequentially stacked in the stated order.

Light generated in the emission layer of the interlayer 130 of the light-emitting device 10 may be extracted (e.g., emitted) toward the outside through the first electrode 110, which is a semi-transmissive electrode or a transmissive electrode, and the first capping layer. Or, light generated in the emission layer of the interlayer 130 of the light-emitting device 10 may be extracted (e.g., emitted) toward the outside through the second electrode 150, which is a semi-transmissive electrode or a transmissive electrode, and the second capping layer.

The first capping layer and the second capping layer may improve external luminescence efficiency based on the principle of constructive interference.

Accordingly, the light extraction efficiency of the light-emitting device 10 is increased, so that the luminescence efficiency of the light-emitting device 10 may be improved.

Each of the first capping layer and the second capping layer may include a material having a refractive index of 1.6 or more (at 589 nm).

Each of the first capping layer and the second capping layer may include the first compound represented by Formula 1.

The first capping layer and the second capping layer may each independently be an organic capping layer including an organic material, an inorganic capping layer including an inorganic material, or an organic-inorganic composite capping layer including an organic material and an inorganic material.

At least one of the first capping layer and the second capping layer may each independently include one or more of carbocyclic compounds, heterocyclic compounds, amine group-containing compounds, porphyrin derivatives, phthalocyanine derivatives, naphthalocyanine derivatives, alkali metal complexes, alkaline earth metal complexes, or any combination thereof. The carbocyclic compound, the heterocyclic compound, and/or the amine group-containing compound may optionally be substituted with a substituent including O, N, S, Se, Si, F, Cl, Br, I, or any combination thereof. In an embodiment, at least one of the first capping layer and the second capping layer may each independently include an amine group-containing compound.

In an embodiment, at least one of the first capping layer and the second capping layer may each independently include a compound represented by Formula 201, a compound represented by Formula 202, or any combination thereof.

In one or more embodiments, at least one of the first capping layer and the second capping layer may each independently include one of Compounds HT28 to HT33, Compounds CP1 to CP6, β-NPB, P4, or any combination thereof:

CP1

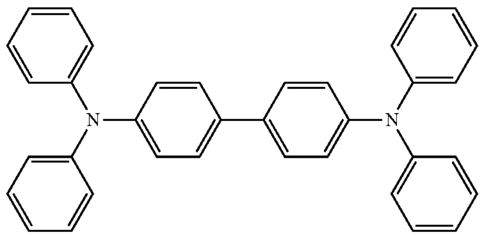

-continued

CP2

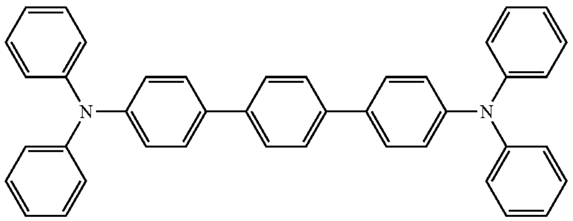

CP3

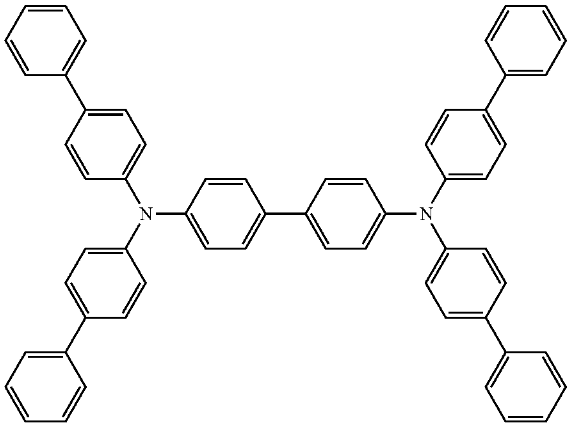

CP4

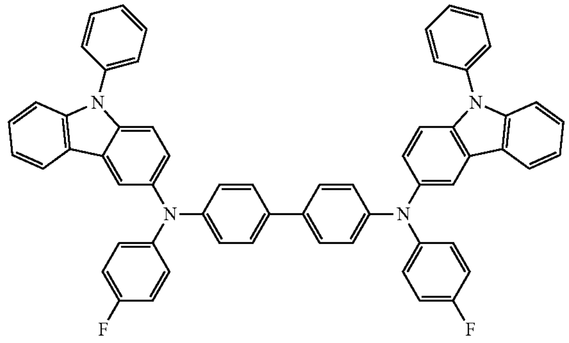

CP5

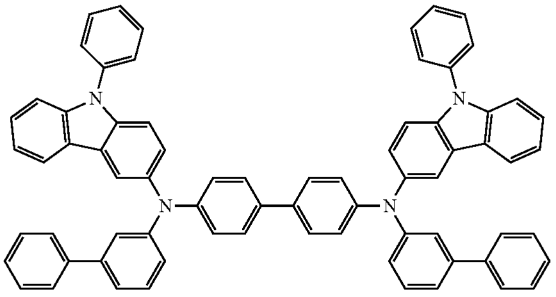

-continued

CP6

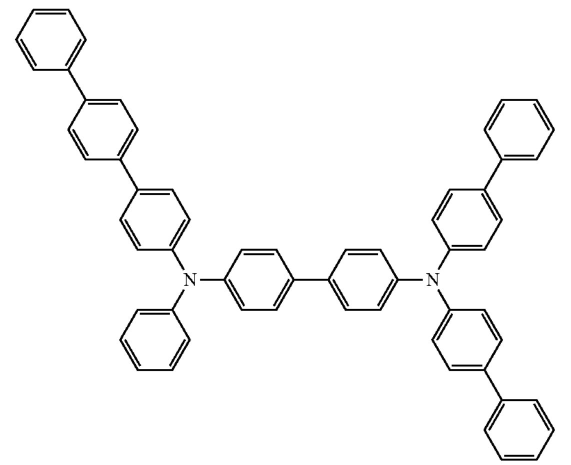

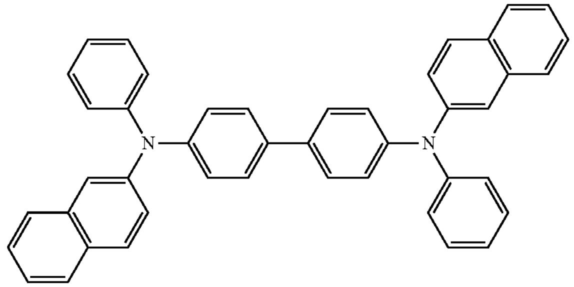

β-NPB

P4

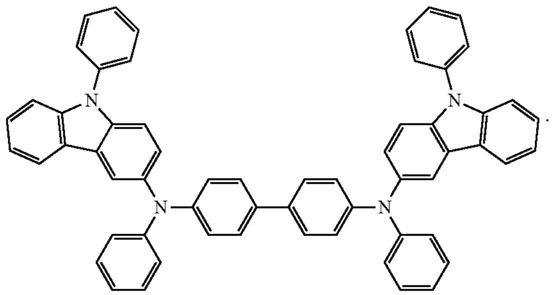

Electronic Apparatus

The light-emitting device may be included in various suitable electronic apparatuses. In an embodiment, the electronic apparatus including the light-emitting device may be a light-emitting apparatus, an authentication apparatus, and/or the like.

The electronic apparatus (for example, a light-emitting apparatus) may further include, in addition to the light-emitting device, i) a color filter, ii) a color conversion layer, or iii) a color filter and a color conversion layer. The color filter and/or the color conversion layer may be located in at least one traveling direction of light emitted from the light-emitting device. In an embodiment, the light emitted from the light-emitting device may be blue light or white light. The light-emitting device is the same as described above. In an embodiment, the color conversion layer may include quantum dots. The quantum dot may be, for example, a quantum dot as described herein.

The electronic apparatus may include a first substrate. The first substrate may include a plurality of sub-pixel areas, the color filter may include a plurality of color filter areas respectively corresponding to the plurality of sub-pixel areas, and the color conversion layer may include a plurality of color conversion areas respectively corresponding to the plurality of sub-pixel areas.

A pixel-defining film may be located between the plurality of sub-pixel areas to define each sub-pixel area.

The color filter may further include a plurality of color filter areas and light-shielding patterns located between the plurality of color filter areas, and the color conversion layer may further include a plurality of color conversion areas and light-shielding patterns located between the plurality of color conversion areas.

The plurality of color filter areas (or the plurality of color conversion areas) may include a first area emitting first-color light, a second area emitting second-color light, and/or a third area emitting third-color light, wherein the first-color light, the second-color light, and/or the third-color light may have different maximum emission wavelengths from one another. In an embodiment, the first-color light may be red light, the second-color light may be green light, and the third-color light may be blue light. In an embodiment, the plurality of color filter areas (or the plurality of color conversion areas) may include quantum dots. In some embodiments, the first area may include a red quantum dot, the second area may include a green quantum dot, and the third area may not include a quantum dot. The quantum dot is the same as described in the present specification. The first area, the second area, and/or the third area may each further include a scatterer.

In an embodiment, the light-emitting device may emit first light, the first area may absorb the first light to emit first first-color light, the second area may absorb the first light to emit second first-color light, and the third area may absorb the first light to emit third first-color light. In this regard, the first first-color light, the second first-color light, and the third first-color light may have different maximum emission wavelengths from one another. For example, the first light may be blue light, the first first-color light may be red light, the second first-color light may be green light, and the third first-color light may be blue light.

The electronic apparatus may further include a thin-film transistor in addition to the light-emitting device as described above. The thin-film transistor may include a source electrode, a drain electrode, and an activation layer, wherein the source electrode or the drain electrode may be electrically connected to one of the first electrode or the second electrode of the light-emitting device.

The thin-film transistor may further include a gate electrode, a gate insulating film, and/or the like.

The activation layer may include crystalline silicon, amorphous silicon, an organic semiconductor, an oxide semiconductor, and/or the like.

The electronic apparatus may further include a sealing portion (e.g., a sealing layer) for sealing the light-emitting device 10. The sealing portion may be located between the color conversion layer and/or color filter and the light-emitting device. The sealing portion allows light from the light-emitting device to be extracted to the outside, and concurrently or simultaneously prevents or substantially prevents ambient air and moisture from penetrating into the light-emitting device. The sealing portion may be a sealing substrate including a transparent glass substrate or a plastic substrate. The sealing portion may be a thin-film encapsulation layer including at least one layer of an organic layer and/or an inorganic layer. When the sealing portion is a thin film encapsulation layer, the electronic apparatus may be flexible.

Various suitable functional layers may be additionally located on the sealing portion, in addition to the color filter and/or the color conversion layer, according to the application or utilization of the electronic apparatus. Examples of the functional layers may include a touch screen layer, a polarizing layer, and/or the like. The touch screen layer may be a pressure-sensitive touch screen layer, a capacitive touch screen layer, or an infrared touch screen layer. The authentication apparatus may be, for example, a biometric authentication apparatus that authenticates an individual by utilizing biometric information of a living body (for example, fingertips, pupils, etc.).

The authentication apparatus may further include, in addition to the light-emitting device as described above, a biometric information collector.

The electronic apparatus may be applied to various suitable displays, light sources, lighting apparatuses, personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram displays, ultrasonic diagnostic devices, and/or endoscope displays), fish finders, various suitable measuring instruments, meters (for example, meters for a vehicle, an aircraft, and/or a vessel), projectors, and/or the like.

Figure 2:
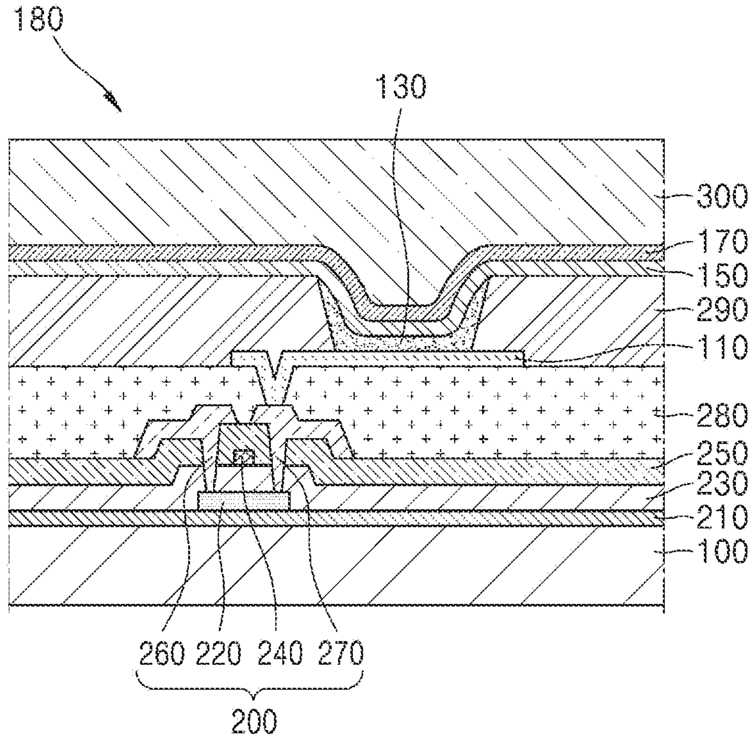
FIG. 2 is a schematic cross-sectional view of an electronic apparatus according to an embodiment.
Figure 3:
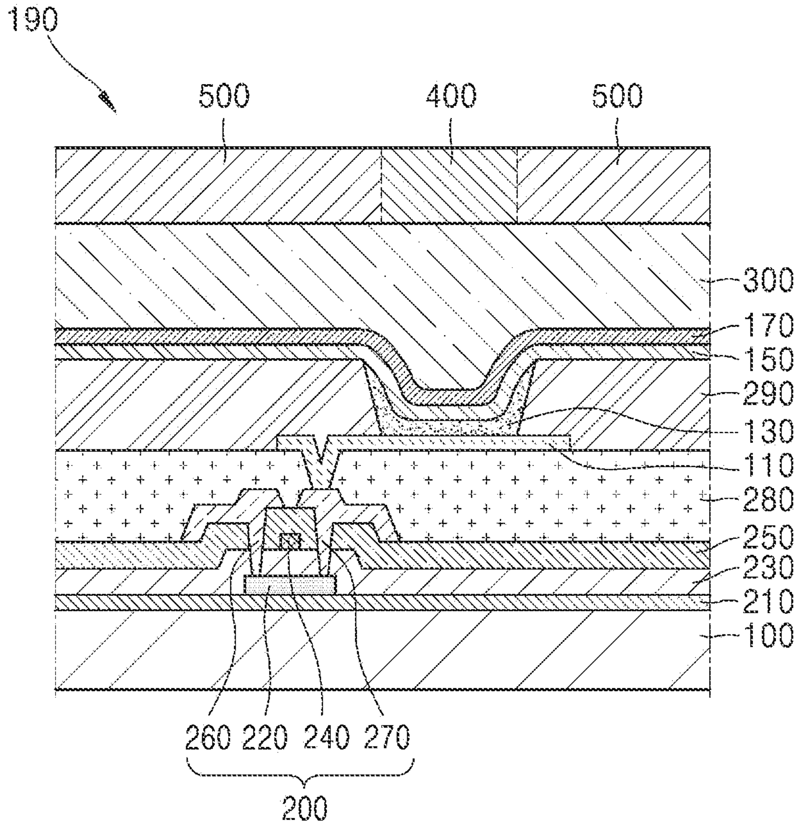
FIG. 3 is a schematic cross-sectional view of an electronic apparatus according to an embodiment.

Description of FIGS. 2 and 3

FIG. 2 is a schematic cross-sectional view of a light-emitting apparatus according to an embodiment of the present disclosure.

The light-emitting apparatus of FIG. 2 includes a substrate 100, a thin-film transistor (TFT), a light-emitting device, and an encapsulation portion 300 that seals the light-emitting device.

The substrate 100 may be a flexible substrate, a glass substrate, or a metal substrate. A buffer layer 210 may be located on the substrate 100. The buffer layer 210 may prevent or reduce penetration of impurities through the substrate 100 and may provide a flat surface on the substrate 100.

A TFT may be located on the buffer layer 210. The TFT may include an activation layer 220, a gate electrode 240, a source electrode 260, and a drain electrode 270.

The activation layer 220 may include an inorganic semiconductor such as silicon and/or polysilicon, an organic semiconductor, and/or an oxide semiconductor, and may include a source region, a drain region, and a channel region.

A gate insulating film 230 for insulating the activation layer 220 from the gate electrode 240 may be located on the activation layer 220, and the gate electrode 240 may be located on the gate insulating film 230.

An interlayer insulating film 250 may be located on the gate electrode 240.

The interlayer insulating film 250 may be located between the gate electrode 240 and the source electrode 260 to insulate the gate electrode 240 from the source electrode 260 and between the gate electrode 240 and the drain electrode 270 to insulate the gate electrode 240 from the drain electrode 270.

The source electrode 260 and the drain electrode 270 may be located on the interlayer insulating film 250. The interlayer insulating film 250 and the gate insulating film 230 may be formed to expose the source region and the drain region of the activation layer 220, and the source electrode 260 and the drain electrode 270 may be in contact with the exposed portions of the source region and the drain region of the activation layer 220.

The TFT is electrically connected to a light-emitting device to drive the light-emitting device, and is covered by a passivation layer 280. The passivation layer 280 may include an inorganic insulating film, an organic insulating film, or any combination thereof. A light-emitting device is provided on the passivation layer 280. The light-emitting device may include the first electrode 110, the interlayer 130, and the second electrode 150.

The first electrode 110 may be located on the passivation layer 280. The passivation layer 280 may not completely cover the drain electrode 270 and may expose a portion of the drain electrode 270, and the first electrode 110 may be connected to the exposed portion of the drain electrode 270.

A pixel-defining layer 290 including an insulating material may be located on the first electrode 110. The pixel-defining layer 290 may expose a region of the first electrode 110, and an interlayer 130 may be formed in the exposed region of the first electrode 110. The pixel defining layer 290 may be a polyimide or polyacrylic organic film. In an embodiment, at least some layers of the interlayer 130 may extend beyond the upper portion of the pixel defining layer 290 to be located in the form of a common layer.

The second electrode 150 may be located on the interlayer 130, and a capping layer 170 may be additionally formed on the second electrode 150. The capping layer 170 may be formed to cover the second electrode 150.

The encapsulation portion 300 may be located on the capping layer 170. The encapsulation portion 300 may be located on the light-emitting device to protect the light-emitting device from moisture and/or oxygen. The encapsulation portion 300 may include: an inorganic film including silicon nitride (SiNx), silicon oxide (SiOx), indium tin oxide, indium zinc oxide, or any combination thereof; an organic film including polyethylene terephthalate, polyethylene naphthalate, polycarbonate, polyimide, polyethylene sulfonate, polyoxymethylene, polyarylate, hexamethyldisiloxane, an acrylic resin (for example, polymethyl methacrylate, polyacrylic acid, and/or the like), an epoxy-based resin (for example, aliphatic glycidyl ether (AGE), and/or the like), or any combination thereof; or any combination of the inorganic film and the organic film.

FIG. 3 is a schematic cross-sectional view of a light-emitting apparatus according to an embodiment of the present disclosure.

The light-emitting apparatus of FIG. 3 is the same as the light-emitting apparatus of FIG. 2, except that a light-shielding pattern 500 and a functional region 400 are additionally located on the encapsulation portion 300. The functional region 400 may be i) a color filter area, ii) a color conversion area, or iii) a combination of the color filter area and the color conversion area. In an embodiment, the light-emitting device included in the light-emitting apparatus of FIG. 3 may be a tandem light-emitting device.

Manufacture Method

The layers constituting the hole transport region, the emission layer, and the layers constituting the electron transport region may be formed in a certain region by utilizing one or more suitable methods such as vacuum deposition, spin coating, casting, Langmuir-Blodgett (LB) deposition, ink-jet printing, laser printing, and/or laser-induced thermal imaging.

When the layers constituting the hole transport region, the emission layer, and the layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec, depending on a material to be included in the layer to be formed and the structure of the layer to be formed.

DEFINITION OF TERMS

The term "$C_3$-$C_{60}$ carbocyclic group" as used herein refers to a cyclic group consisting of only carbon atoms as ring-forming atoms and having three to sixty carbon atoms, and the term "$C_1$-$C_{60}$ heterocyclic group" as used herein refers to a cyclic group that has, in addition to one to sixty carbon atoms, a heteroatom as a ring-forming atom.

The $C_3$-$C_{60}$ carbocyclic group and the $C_1$-$C_{60}$ heterocyclic group may each be a monocyclic group consisting of one ring or a polycyclic group in which two or more rings are condensed with each other. In an embodiment, the $C_1$-$C_{60}$ heterocyclic group has 3 to 61 ring-forming atoms.

The "cyclic group" as used herein may include the $C_3$-$C_{60}$ carbocyclic group and the $C_1$-$C_{60}$ heterocyclic group.

The term "π electron-rich $C_3$-$C_{60}$ cyclic group" as used herein refers to a cyclic group that has three to sixty carbon atoms and does not include *—N=*' as a ring-forming moiety, and the term "π electron-deficient nitrogen-containing $C_1$-$C_{60}$ cyclic group" as used herein refers to a heterocyclic group that has one to sixty carbon atoms and also includes *—N=*' as a ring-forming moiety.

In an embodiment, the $C_3$-$C_{60}$ carbocyclic group may be i) group T1 or ii) a condensed cyclic group in which two or more groups T1 are condensed with each other (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be i) group T2, ii) a condensed cyclic group in which two or more groups T2 are condensed with each other, or iii) a condensed cyclic group in which at least one group T2 and at least one group T1 are condensed with each other (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), the π electron-rich $C_3$-$C_{60}$ cyclic group may be i) group T1, ii) a condensed cyclic group in which two or more groups T1 are condensed with each other, iii) group T3, iv) a condensed cyclic group in which two or more groups T3 are condensed with each other, or v) a condensed cyclic group in which at least one group T3 and at least one group T1 are condensed with each other (for example, the $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonaphthothiophene group, a benzonaphthosilole group, a benzofurodibenzofuran group, a benzofurodibenzothiophene group, a benzothienodibenzothiophene group, etc.), the π electron-deficient nitrogen-containing $C_1$-$C_{60}$ cyclic group may be i) group T4, ii) a condensed cyclic group in which two or more groups T4 are condensed with each other, iii) a condensed cyclic group in which at least one group T4 and at least one group T1 are condensed with each other, iv) a condensed cyclic group in which at least one group T4 and at least one group T3 are condensed with each other, or v) a condensed cyclic group in which at least one group T4, at least one group T1, and at least one group T3 are condensed with one another (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, etc.), group T1 may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or a bicyclo[2.2.1]heptane) group, a norbornene group, a bicyclo[1.1.1]pentane group, a bicyclo[2.1.1]hexane group, a bicyclo[2.2.2]octane group, or a benzene group, group T2 may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, group T3 may be a furan group, a thiophene group, a 1H-pyrrole group, a silole group, or a borole group, and group T4 may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "the cyclic group," "the $C_3$-$C_{60}$ carbocyclic group," "the $C_1$-$C_{60}$ heterocyclic group," "the Tr electron-rich $C_3$-$C_{60}$ cyclic group," or "the π electron-deficient nitrogen-containing $C_1$-$C_{60}$ cyclic group" as used herein each refer to a group connected (e.g., condensed) to a cyclic group, a monovalent group, or a polyvalent group (for example, a divalent group, a trivalent group, a tetravalent group, etc.) depending on the structure of a formula for which the corresponding term is used. In an embodiment, the "benzene group" may be a benzo group, a phenyl group, a phenylene group, and/or the like, which may be easily understood by one of ordinary skill in the art according to the structure of a formula including the "benzene group."

Examples of the monovalent $C_3$-$C_{60}$ carbocyclic group and the monovalent $C_1$-$C_6$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, and examples of the divalent $C_3$-$C_{60}$ carbocyclic group and the divalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group" as used herein refers to a linear or branched aliphatic hydrocarbon monovalent group that has one to sixty carbon atoms, and examples thereof may include a methyl group, an ethyl group, an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group. The term "$C_1$-$C_{60}$ alkylene group" as used herein refers to a divalent group having the same structure as the $C_1$-$C_6$ alkyl group.

The term "$C_2$-$C_{60}$ alkenyl group" as used herein refers to a monovalent hydrocarbon group having at least one carbon-carbon double bond at a main chain (e.g., in the middle) or at a terminal end (e.g., the terminus) of the $C_2$-$C_{60}$ alkyl group, and examples thereof may include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a monovalent hydrocarbon group having at least one carbon-carbon triple bond at a main chain (e.g., in the middle) or at a terminal end (e.g., the terminus) of the $C_2$-$C_{60}$ alkyl group, and examples thereof may include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by $—OA_{101}$ (wherein $A_{101}$ is the $C_1$-$C_{60}$ alkyl group), and examples thereof may include a methoxy group, an ethoxy group, and an isopropyloxy group.

The term "$C_3$-$C_{10}$ cycloalkyl group" as used herein refers to a monovalent saturated hydrocarbon cyclic group having three to ten carbon atoms, and examples thereof may include a cyclopropyl group, a cyclobutyl group, a cyclopentyl group, a cyclohexyl group, a cycloheptyl group, a cyclooctyl group, an adamantanyl group, a norbornanyl group (or bicyclo[2.2.1]heptyl group), a bicyclo[1.1.1]pentyl group, a bicyclo[2.1.1]hexyl group, and a bicyclo[2.2.2]octyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent cyclic group that further includes, in addition to one to ten carbon atoms, at least one heteroatom as a ring-forming atom, and examples thereof may include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent cyclic group that has three to ten carbon atoms and at least one carbon-carbon double bond in the ring thereof and no aromaticity, and examples thereof may include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent cyclic group that has, in addition to one to ten carbon atoms, at least one heteroatom as a ring-forming atom, and at least one double bond in the cyclic structure thereof. Examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having six to sixty carbon atoms, and the term "$C_6$-$C_{60}$ arylene group" as used herein refers to a divalent group having a carbocyclic aromatic system having six to sixty carbon atoms. Examples of the $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, a fluorenyl group, and an ovalenyl group. When the $C_6$-$C_{60}$ aryl group and the $C_6$-$C_{60}$ arylene group each include two or more rings, the two or more rings may be condensed with each other.

The term "$C_1$-$C_{60}$ heteroaryl group" as used herein refers to a monovalent group having a heterocyclic aromatic system that has, in addition to one to sixty carbon atoms, at least one heteroatom as a ring-forming atom. The term "$C_1$-$C_{60}$ heteroarylene group" as used herein refers to a divalent group having a heterocyclic aromatic system that has, in addition to one to sixty carbon atoms, at least one heteroatom as a ring-forming atom. Examples of the $C_1$-$C_6$ heteroaryl group may include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, a carbazolyl group, a dibenzofuranyl group, a dibenzothiofuranyl group, and a naphthyridinyl group. When the $C_1$-$C_6$ heteroaryl group and the $C_1$-$C_{60}$ heteroarylene group each include two or more rings, the two or more rings may be condensed with each other.

The term "monovalent non-aromatic condensed polycyclic group" as used herein refers to a monovalent group having two or more rings condensed with each other, only carbon atoms (for example, having eight to sixty carbon atoms) as ring-forming atoms, and no aromaticity in its entire molecular structure (e.g., the entire molecular structure is not aromatic). Examples of the monovalent non-aromatic condensed polycyclic group may include an indenyl group, a fluorenyl group, a spiro-bifluorenyl group, a benzofluorenyl group, an indenophenanthrenyl group, an adamantyl group, and an indenoanthracenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed with each other, at least one heteroatom other than carbon atoms (for example, having one to sixty carbon atoms), as a ring-forming atom, and no aromaticity in its entire molecular structure (e.g., the entire molecular structure is not aromatic). Examples of the monovalent non-aromatic condensed heteropolycyclic group may include a pyrrolyl group, a thiophenyl group, a furanyl group, an indolyl group, a benzoindolyl group, a naphtho indolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzoxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl group, an azaadamantyl group, and a benzothienodibenzothiophenyl group. The term "divalent non-aromatic condensed heteropolycyclic group" as used herein refers to a divalent group having the same structure as the monovalent non-aromatic condensed heteropolycyclic group.

The term "$C_6$-$C_{60}$ aryloxy group" as used herein refers to a monovalent group represented by $—OA_{102}$ (wherein $A_{102}$ may be a $C_6$-$C_{60}$ aryl group), and the term "$C_6$-$C_{60}$ arylthio group" as used herein refers to a monovalent group represented by $—SA_{103}$ (wherein $A_{103}$ may be a $C_6$-$C_{60}$ aryl group).

The term "$C_7$-$C_{60}$ aryl alkyl group" used herein refers to a monovalent group represented by $-A_{104}A_{105}$ (wherein $A_{104}$ may be a $C_1$-$C_{54}$ alkylene group, and $A_{105}$ may be a $C_6$-$C_{59}$ aryl group), and the term $C_2$-$C_{60}$ heteroaryl alkyl group" used herein refers to a monovalent group represented by $-A_{106}A_{107}$ (wherein $A_{106}$ may be a $C_1$-$C_{59}$ alkylene group, and $A_{107}$ may be a $C_1$-$C_{59}$ heteroaryl group).

The term "$R_{10a}$" as used herein refers to:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, $—Si(Q_{11})(Q_{12})(Q_{13})$, $—N(Q_{11})(Q_{12})$, $—B(Q_{11})(Q_{12})$, $—C(=O)(Q_{11})$, $—S(=O)_2(Q_{11})$, $—P(=O)(Q_{11})(Q_{12})$, or any combination thereof;

a $C_3$-$C_{60}$ carbocyclic group, a $C_1$-$C_6$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), —P(=O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$).

$Q_1$ to $Q_3$, $Q_{11}$ to $Q_{13}$, $Q_{21}$ to $Q_{23}$, and $Q_{31}$ to $Q_{33}$ as used herein may each independently be: hydrogen; deuterium; —F; —Cl; —Br; —I; a hydroxyl group; a cyano group; a nitro group; a $C_1$-$C_6$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein refers to any atom other than a carbon atom. Examples of the heteroatom include O, S, N, P, Si, B, Ge, Se, or any combination thereof.

The term "transition metal" as used herein includes hafnium (Hf), tantalum (Ta), tungsten (W), rhenium (Re), osmium (Os), iridium (Ir), platinum (Pt), gold (Au), and/or the like.

The term "Ph" as used herein refers to a phenyl group, the term "Me" as used herein refers to a methyl group, the term "Et" as used herein refers to an ethyl group, the term "ter-Bu," "$^t$Bu," or "Bu$^t$" as used herein refers to a tert-butyl group, and the term "OMe" as used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group". In other words, the "terphenyl group" is a substituted phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula or moiety.

Hereinafter, compounds according to embodiments and light-emitting devices according to embodiments will be described in more detail with reference to the following Synthesis Examples and Examples. The wording "B was utilized instead of A" used in describing Synthesis Examples refers to that an identical molar equivalent of B was utilized in place of A.

EXAMPLE

Example 1

As an anode, a glass substrate (product of Corning Inc.) with a 15 Ω/cm$^2$ (1,200 Å) ITO electrode formed thereon was cut to a size of 50 mm×50 mm×0.5 mm, sonicated with isopropyl alcohol and pure water each for 10 minutes, and then cleaned by exposure to ultraviolet rays and ozone for 10 minutes. Then, the resultant structure was mounted on a vacuum deposition apparatus.

m-MTDATA was deposited on the anode to form a hole injection layer having a thickness of 40 Å, and then, NPB was deposited on the hole injection layer to form a hole transport layer having a thickness of 10 Å.

Compound 1-1 (first compound, host), Compound 2-1 (second compound, host), and Dopant-1 (dopant) were co-deposited at a weight ratio of 50:50:1 on the hole transport layer to form an emission layer having a thickness of 300 Å.

Subsequently, ETL1 was deposited on the emission layer to form an electron transport layer having a thickness of 300 Å, and then, Al was deposited on the electron transport layer to form a cathode having a thickness of 1,200 Å, thereby completing the manufacture of an organic light-emitting device having the structure of ITO (1,200 Å)/m-MTDATA (40 Å)/NPB (10 Å)/Compound 1-1 (first compound, host)+Compound 2-1 (second compound, host)+Dopant-1 (50:50:1) (300 Å)/ETL1 (300 Å)/Al (1,200 Å).

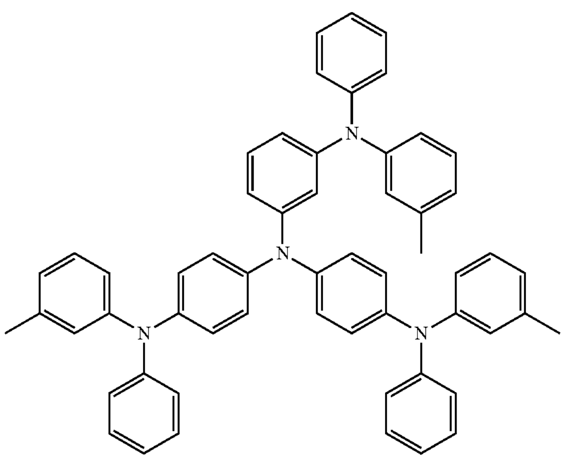

m-MTDATA

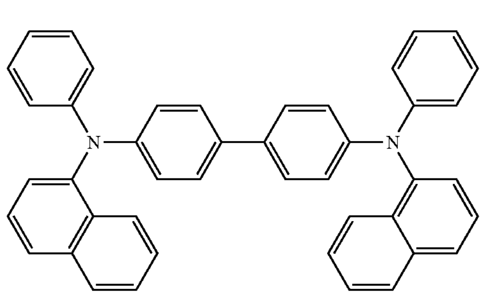

NPB

-continued

ET1

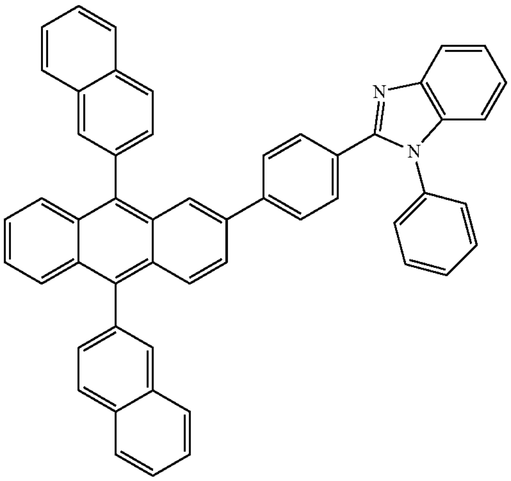

1-1

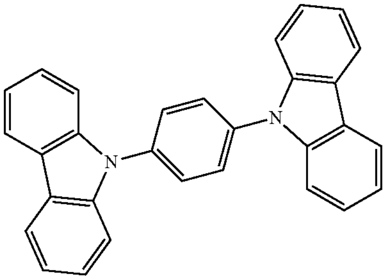

2-1

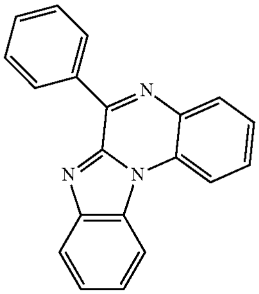

-continued

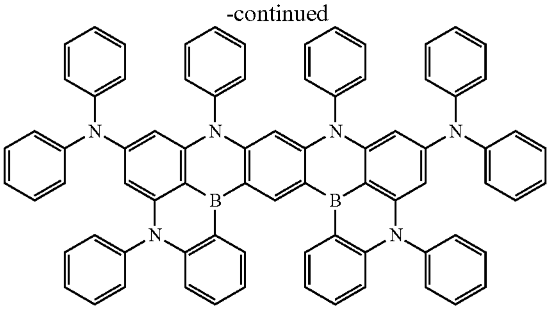

Dopant-1

Examples 2 to 12 and Comparative Examples 1 to 6

Organic light-emitting devices were manufactured in the same manner as in Example 1, except that, in an emission layer, the compounds shown in Table 1 were respectively utilized instead of Compound 1-1 as a first compound, Compound 2-1 as a second compound, and Dopant-1 as a dopant.

Evaluation Example 2

Each of the luminescence efficiency (Cd/A) at the current density of 10 mA/$cm^2$ and lifespan of the organic light-emitting devices manufactured in Examples 1 to 12 and Comparative Examples 1 to 6 was measured utilizing Keithley MU236 and luminance meter SR3, respectively, and results thereof are shown in Table 1.

TABLE 1

| No. | Emission layer First compound (host) | Second compound (host) | Dopant | Luminescence efficiency (cd/A) | Lifespan ($T_{90}$) |
|---|---|---|---|---|---|
| Example 1 | 1-1 | 2-1 | Dopant-1 | 20.4 | 34.2 |
| Example 2 | 1-5 | 2-1 | Dopant-1 | 22.1 | 35.8 |
| Example 3 | 1-19 | 2-2 | Dopant-1 | 24.2 | 32.6 |
| Example 4 | 1-20 | 2-4 | Dopant-1 | 21.8 | 34.8 |
| Example 5 | 1-22 | 2-7 | Dopant-1 | 23.8 | 39.8 |
| Example 6 | 1-1 | 2-1 | Dopant-2 | 21.1 | 35.8 |
| Example 7 | 1-5 | 2-1 | Dopant-2 | 23.5 | 36.4 |
| Example 8 | 1-19 | 2-2 | Dopant-2 | 24.5 | 33.9 |
| Example 9 | 1-20 | 2-4 | Dopant-2 | 22.5 | 37.0 |
| Example 10 | 1-22 | 2-7 | Dopant-2 | 26.6 | 42.2 |
| Example 11 | 1-19 | ET host | Dopant-1 | 22.1 | 21.4 |
| Example 12 | 1-19 | ET host | Dopant-2 | 20.1 | 24.5 |
| Comparative Example 1 | 1-4 | — | Dopant-1 | 16.1 | 8.2 |

TABLE 1-continued
| No. | Emission layer: First compound (host) | Emission layer: Second compound (host) | Dopant | Luminescence efficiency (cd/A) | Lifespan ($T_{90}$) |
|---|---|---|---|---|---|
| Comparative Example 2 | 1-18 | — | Dopant-1 | 20.1 | 15.4 |
| Comparative Example 3 | — | 2-1 | Dopant-1 | 13.4 | 13.5 |
| Comparative Example 4 | 1-4 | — | Dopant-2 | 21.2 | 17.2 |
| Comparative Example 5 | 1-18 | — | Dopant-2 | 11.1 | 15.3 |
| Comparative Example 6 | — | 2-1 | Dopant-2 | 10.1 | 11.2 |
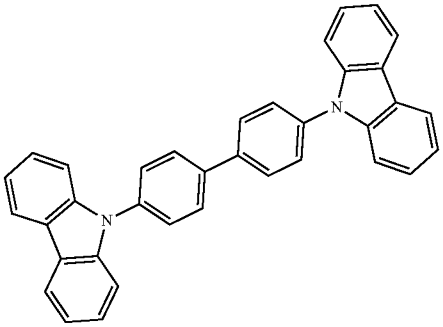
1-4
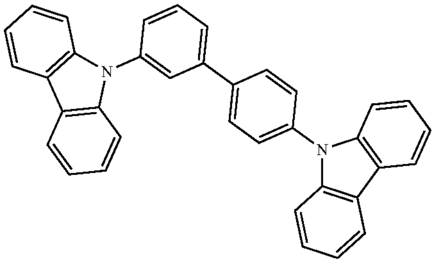
1-5
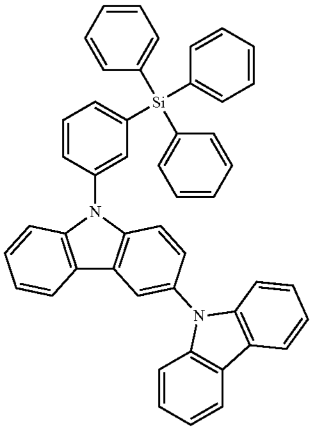
1-18

TABLE 1-continued
| | Emission layer | | | | |
|---|---|---|---|---|---|
| No. | First compound (host) | Second compound (host) | Dopant | Luminescence efficiency (cd/A) | Lifespan ($T_{90}$) |
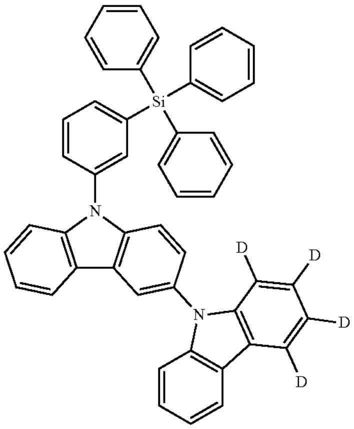
1-19
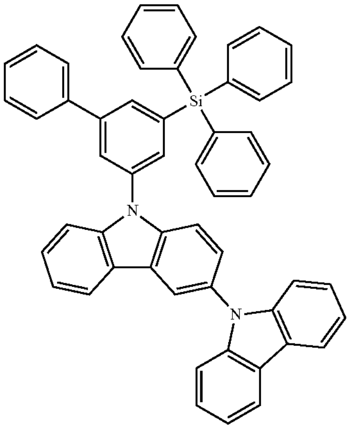
1-20
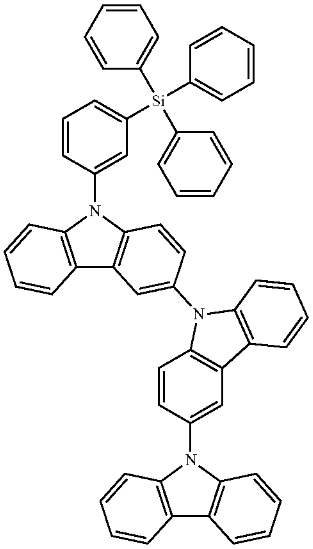
1-22

TABLE 1-continued
| | Emission layer | | | | |
|---|---|---|---|---|---|
| No. | First compound (host) | Second compound (host) | Dopant | Luminescence efficiency (cd/A) | Lifespan ($T_{90}$) |
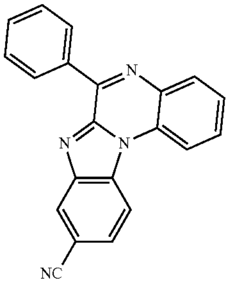
2-2
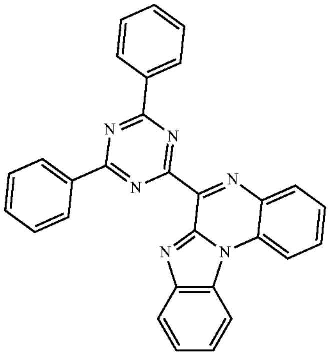
2-4
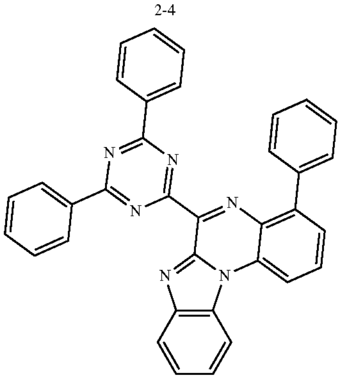
2-7
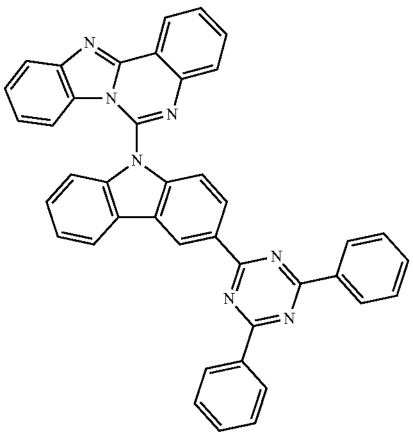
ET host TABLE 1-continued

| No. | Emission layer First compound (host) | Second compound (host) | Dopant | Luminescence efficiency (cd/A) | Lifespan ($T_{90}$) |
|---|---|---|---|---|---|

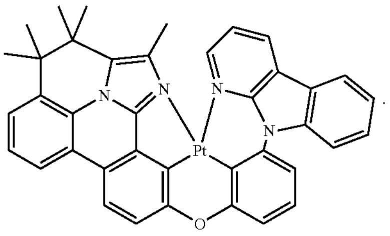

Dopant-2

Referring to Table 1, it is confirmed that the organic light-emitting devices of Examples 1 to 12, which each concurrently or simultaneously include a first compound and a second compound, have improved luminescence efficiency and improved lifespan, as compared with the organic light-emitting devices of Comparative Examples 1 to 6, which include only the first compound or the second compound.

Because the light-emitting device includes the first compound represented by Formula 1 and the second compound represented by Formula 2, suitable (e.g., excellent) luminescence efficiency and suitable (e.g., excellent) luminescence lifespan may be obtained. Accordingly, a high-quality electronic apparatus may be manufactured utilizing the light-emitting device.

Expressions such as "at least one of," when preceding a list of elements, modify the entire list of elements and do not modify the individual elements of the list. Further, the use of "may" when describing embodiments of the inventive concept refers to "one or more embodiments of the inventive concept."

As used herein, the terms "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein.

Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims, and equivalents thereof.

What is claimed is:

1. A light-emitting device comprising:

a first electrode;

a second electrode facing the first electrode;

an interlayer between the first electrode and the second electrode and comprising an emission layer;

a first compound represented by Formula 1; and a second compound represented by Formula 2:

Formula 1

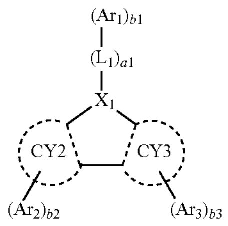

Formula 2

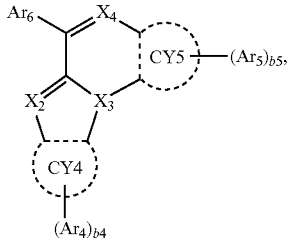

and wherein, in Formulae 1 and 2, $X_1$ is N, B, P(=O), or P(=S), $X_2$ is N, B, P(=O), or P(=S), $X_3$ is N, B, P(=O), or P(=S), $X_4$ is N, B, P(=O), or P(=S), $L_1$ is a single bond, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$, a1 is an integer from 0 to 3, ring CY2 to ring CY5 are each independently a $C_3$-$C_{60}$ carbocyclic group or a $C_1$-$C_{60}$ heterocyclic group, $Ar_1$ to $Ar_6$ are each independently selected from hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, —Si($Q_1$)($Q_2$)($Q_3$), —N($Q_1$)($Q_2$), —B($Q_1$)($Q_2$), —C(═O)($Q_1$), —S(═O)$_2$($Q_1$), and —P(═O)($Q_1$)($Q_2$), b1 to b5 are each an integer from 0 to 10, and $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —Si($Q_{11}$)($Q_{12}$)($Q_{13}$), —N($Q_{11}$)($Q_{12}$), —B($Q_{11}$)($Q_{12}$), —C(═O)($Q_{11}$), —S(═O)$_2$($Q_{11}$), —P(═O)($Q_{11}$)($Q_{12}$), or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-Coo arylthio group, a $C_7$-Coo aryl alkyl group, a $C_2$-$C_{60}$ heteroaryl alkyl group, —Si($Q_{21}$)($Q_{22}$)($Q_{23}$), —N($Q_{21}$)($Q_{22}$), —B($Q_{21}$)($Q_{22}$), —C(═O)($Q_{21}$), —S(═O)$_2$($Q_{21}$), —P(═O)($Q_{21}$)($Q_{22}$), or any combination thereof; or —Si($Q_{31}$)($Q_{32}$)($Q_{33}$), —N($Q_{31}$)($Q_{32}$), —B($Q_{31}$)($Q_{32}$), —C(═O)($Q_{31}$), —S(═O)$_2$($Q_{31}$), or —P(═O)($Q_{31}$)($Q_{32}$), and wherein $Q_1$ to $Q_3$, $Q_{11}$ to $Q_{13}$, $Q_{21}$ to $Q_{23}$, and $Q_{31}$ to $Q_{33}$ are each independently hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

2. The light-emitting device of claim 1, wherein the emission layer comprises the first compound and the second compound.

3. The light-emitting device of claim 2, wherein each of the first compound and the second compound is a host.

4. The light-emitting device of claim 2, wherein the first compound and the second compound are different from each other.

5. The light-emitting device of claim 2, wherein the emission layer further comprises a dopant.

6. The light-emitting device of claim 5, wherein the dopant comprises a phosphorescent dopant, a delayed fluorescence material, or any combination thereof.

7. The light-emitting device of claim 1, wherein the emission layer is to emit blue light.

8. The light-emitting device of claim 1, wherein a ratio of an amount of the first compound to an amount of the second compound is in a range of 1:0.1 to 1:10.

9. The light-emitting device of claim 1, wherein, in Formulae 1 and 2, $X_1$ is N, P(═O), or P(═S), $X_2$ is N, P(═O), or P(═S), $X_3$ is N, P(═O), or P(═S), and $X_4$ is N, P(═O), or P(═S).

10. The light-emitting device of claim 1, wherein, in Formula 1, $L_1$ is:

a single bond; or a benzene group or a carbazole group, each unsubstituted or substituted with at least one $R_{10a}$.

11. The light-emitting device of claim 1, wherein, in Formulae 1 and 2, ring CY2 to ring CY5 are each independently a benzene group, a naphthalene group, a carbazole group, a dibenzofuran group, a fluorene group, a dibenzothiophene group, or a dibenzosilole group, each unsubstituted or substituted with at least one $R_{10a}$.

12. The light-emitting device of claim 1, wherein, in Formula 1, ring CY2 is a group represented by one of Formulae CY2-1 to CY2-5:

CY2-1

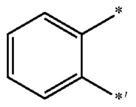

CY2-2

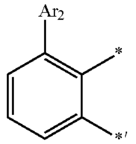

CY2-3

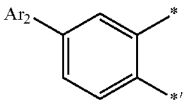

CY2-4

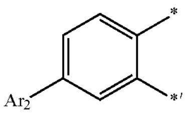

CY2-5

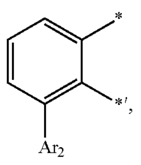

, and wherein, in Formulae CY2-1 to CY2-5, $Ar_2$ is the same as described in connection with Formula 1,

* indicates a binding site to $X_1$ in Formula 1, and

*' indicates a binding site to an element included in ring CY3 in Formula 1.

13. The light-emitting device of claim 1, wherein, in Formula 1, ring CY3 is a group represented by one of Formulae CY3-1 to CY3-5:

CY3-1

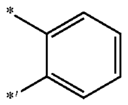

CY3-2

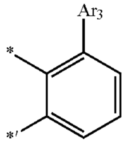

CY3-3

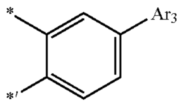

CY3-4

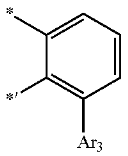

CY3-5

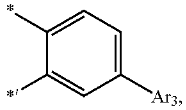

, and wherein, in Formulae CY3-1 to CY3-5, $Ar_3$ is the same as described in connection with Formula 1,

* indicates a binding site to $X_1$ in Formula 1, and

**' indicates a binding site to an element included in ring CY2 in Formula 1.

14. The light-emitting device of claim 1, wherein, in Formula 2, ring CY4 is a group represented by one of Formulae CY4-1 to CY4-5:

CY4-1

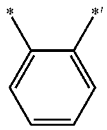

CY4-2

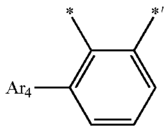

CY4-3

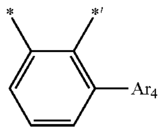

-continued

CY4-4

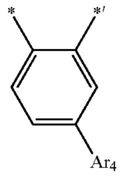

CY4-5

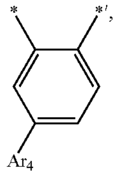

, and wherein, in Formulae CY4-1 to CY4-5, $Ar_4$ is the same as described in connection with Formula 1,

* indicates a binding site to $X_2$ in Formula 2, and

**' indicates a binding site to $X_3$ in Formula 2.

15. The light-emitting device of claim 1, wherein, in Formula 2, ring CY5 is a group represented by one of Formulae CY5-1 to CY5-5:

CY5-1

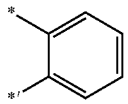

CY5-2

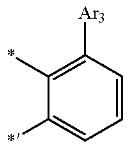

CY5-3

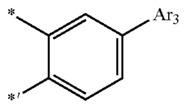

CY5-4

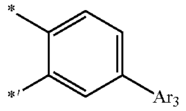

CY5-5

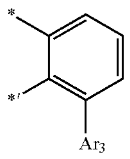

, and wherein, in Formulae CY5-1 to CY5-5, $Ar_3$ is the same as described in connection with Formula 1,

* indicates a binding site to $X_4$ in Formula 2, and

**' indicates a binding site to $X_3$ in Formula 2.

16. The light-emitting device of claim 1, wherein, in Formula 1, $Ar_1$ to $Ar_3$ are each independently:

hydrogen, deuterium, a group represented by —$Si(Q_1)(Q_2)(Q_3)$; or a group represented by one of Formulae 4-1 to 4-10:

4-1

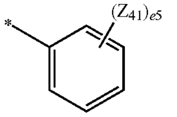

4-2

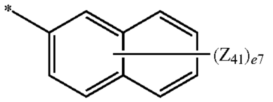

4-3

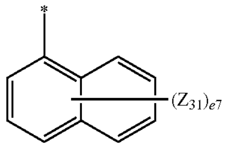

4-4

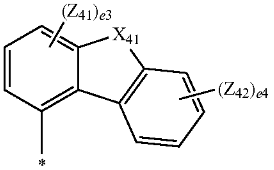

4-5

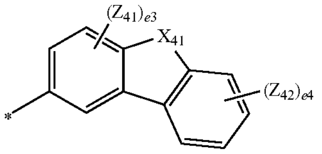

4-6

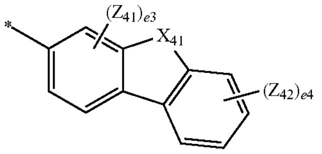

4-7

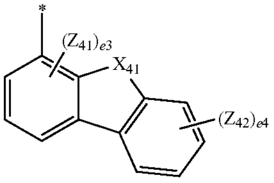

4-8

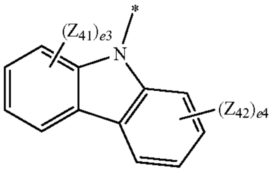

4-9

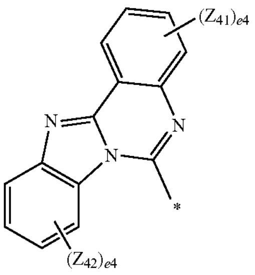

-continued 4-10

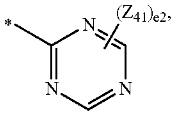

and wherein, in Formulae 4-1 to 4-10, $X_{41}$ is $C(R_{41a})(R_{41b})$, $Si(R_{41a})(R_{41b})$, $N(R_{41a})$, O, S, or Se, $Q_1$ to $Q_3$ are each independently the same as described in connection with Formula 1, $R_{41a}$, $R_{41b}$, $Z_{41}$, and $Z_{42}$ are each independently hydrogen or the same as described in connection with $R_{10a}$, e2 is an integer from 0 to 2, e3 is an integer from 0 to 3, e4 is an integer from 0 to 4, e5 is an integer from 0 to 5, e7 is an integer from 0 to 7, and

* indicates a binding site to a neighboring group.

17. The light-emitting device of claim 1, wherein, in Formula 2, $Ar_4$ to $Ar_6$ are each independently:

hydrogen, deuterium, a cyano group; or a group represented by one of Formulae 5-1 to 5-3:

5-1

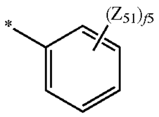

5-2

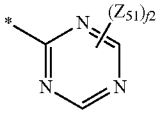

5-3

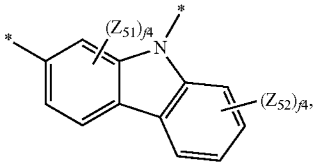

and wherein, in Formulae 5-1 to 5-3, $Z_{51}$ and $Z_{52}$ are each independently hydrogen or the same as described in connection with $R_{10a}$, f2 is an integer from 0 to 2, f4 is an integer from 0 to 4, f5 is an integer from 0 to 4, and

* indicates a binding site to a neighboring group.

18. An electronic apparatus comprising the light-emitting device of claim 1.

19. The electronic apparatus of claim 18, further comprising a thin-film transistor, wherein the thin-film transistor comprises a source electrode and a drain electrode, and the first electrode of the light-emitting device is electrically connected to the source electrode or the drain electrode of the thin-film transistor.

20. The electronic apparatus of claim 18, further comprising a color filter, a color conversion layer, a touch screen layer, a polarizing layer, or any combination thereof.

* * * * *